(12) United States Patent
Booth

(10) Patent No.: US 10,017,458 B2
(45) Date of Patent: Jul. 10, 2018

(54) THERAPEUTIC TETRAHYDRONAPHTHALENE COMPOUNDS

(71) Applicant: University of Florida Research Foundation, Inc., Gainesville, FL (US)

(72) Inventor: Raymond G. Booth, Boston, MA (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

(21) Appl. No.: 14/665,928

(22) Filed: Mar. 23, 2015

(65) Prior Publication Data
US 2015/0315127 A1 Nov. 5, 2015

Related U.S. Application Data

(62) Division of application No. 13/318,877, filed as application No. PCT/US2010/001333 on May 5, 2010, now Pat. No. 9,024,071.

(60) Provisional application No. 61/277,408, filed on Sep. 24, 2009, provisional application No. 61/241,384, filed on Sep. 10, 2009, provisional application No. 61/215,504, filed on May 5, 2009.

(51) Int. Cl.
| | | |
|---|---|---|
| C07C 211/42 | (2006.01) | |
| A61K 31/13 | (2006.01) | |
| C07C 217/74 | (2006.01) | |

(52) U.S. Cl.
CPC ............ *C07C 211/42* (2013.01); *A61K 31/13* (2013.01); *C07C 217/74* (2013.01); *C07C 2601/14* (2017.05); *C07C 2602/10* (2017.05)

(58) Field of Classification Search
None
See application file for complete search history.

(56) References Cited

U.S. PATENT DOCUMENTS

| 4,091,115 A | 5/1978 | Nedelec et al. | |
|---|---|---|---|
| 9,024,071 B2 * | 5/2015 | Booth .................... | A61K 31/13 |
| | | | 564/428 |

FOREIGN PATENT DOCUMENTS

| FR | 2353519 A1 | 12/1977 | | |
|---|---|---|---|---|
| JP | S5217455 A | 2/1977 | | |
| JP | H0517737 A | 1/1993 | | |
| JP | 2002533447 A | 10/2002 | | |
| JP | 2005343805 A | 12/2005 | | |
| WO | WO96/01107 | * 1/1996 | ........... | A61K 31/135 |
| WO | WO-200039105 A1 | 7/2000 | | |
| WO | WO-2007/081542 A2 | 7/2007 | | |
| WO | WO-2008/154044 A1 | 12/2008 | | |

(Continued)

OTHER PUBLICATIONS

Golub et al. Science (1999), vol. 286 531-537, p. 531.*

(Continued)

*Primary Examiner* — Clinton A Brooks
(74) *Attorney, Agent, or Firm* — Wolf, Greenfield & Sacks, P.C.

(57) ABSTRACT

The invention relates to protein binding interacting/binding compounds and methods of identifying and using them. The invention further relates to pharmaceutical compositions and methods for treating 5-HT2C and/or RSK disorders, including diseases and disorders mediated by CPCRs and/or RSKs.

13 Claims, 50 Drawing Sheets

Representative binding curves of (-)-*trans*-CAT and (+)-*trans*-CAT with wild type 5HT2A, 5HT2B, 5HT2C and Histamine H1 receptors transiently expressed in HEK 293 cells.

Binding of (-)-*trans*-CAT to wild type receptors of 5HT2A, 5HT2B, 5HT2C and Histamine H1

(56) References Cited

FOREIGN PATENT DOCUMENTS

WO   WO-2008/156707 A1   12/2008

OTHER PUBLICATIONS http://www.mayoclinic.org/diseases-conditions/hiv-aids/basics/treatment/con-20013732; downloaded (2016).*
Fukioka, Diabetes, Obesity and Metabolism 2015, 17: 1021-1032.*
Filip et al. Journal of Pharmacology and Experimental Therapeutics, 2004, 310(3), 1246-1254.*
Sonier et al. Biochemical and Biophysical Research Communications 343 (2006) 1053-1059.*
Ghoneim et al. Bioorganic and Medicinal Chemistry 2006, 14(19), 6640-6658.*
Ola M. Ghoneim et al., "Novel ligands for the human histamine H1 receptor: synthesis, pharmacology, and comparative molecular field analysis studies of 2-dimethylamin-5-(6)-phnyl-1,2,3,4-tetrahydronaphthalenes", Bioorganic & Medicinal Chemistry, Oct. 1, 2006, 14(19), pp. 6640-6658.
Neil E. Rowland et al., "Effect of (−)-trans-PAT, a novel 5-HT2C receptor agonist, on intake of palatable food in mice", Pharmacology Biochemistry and Behavior, Nov. 2008, 91(1), pp. 176-180.
Nader H. Moniri et al., "Ligand-directed functional heterogeneity of histamine H1 receptors: novel dual-function ligands selectively activate and block H1-mediated phospholipase C and adenylyl cyclase signaling", J. Pharmacol. Exp. Ther., Oct. 2004, 311(1), pp. 274-281.
JP Office Action dated Jun. 3, 2014 for JP Application 2012-509789.
Gutsche, C. David et al.; The Cyclodehydration of 2-(γ-Phenylpropyl)-cycloheptanone; Dept. of Chemistry, Washington University; vol. 79; pp. 4441-4448.
Chemical Abstracts; vol. 1940: 7283-7284.
Booth et al. J. Med. Chem. 1993, 36(17), 2542-51.
Extended European Search Report dated Dec. 10, 2013 for EP 10772381.9.
International Search Report and Written Opinion dated Jan. 27, 2011 for PCT/US2010/001333.
Jackson et al., The interaction of R(+)- or S(−)-2,2'-diamino-1,1'-binaphthalene with a Pd/silica catalyst in tetrahydrofuran. Enantiomer. Dec. 2000;5(6):567-70.

* cited by examiner

Representative binding curves of (-)-*trans*-CAT and (+)-*trans*-CAT with wild type 5HT2A, 5HT2B, 5HT2C and Histamine H1 receptors transiently expressed in HEK 293 cells.
FIG 1A. Binding of (-)-*trans*-CAT to wild type receptors of 5HT2A, 5HT2B, 5HT2C and Histamine H1
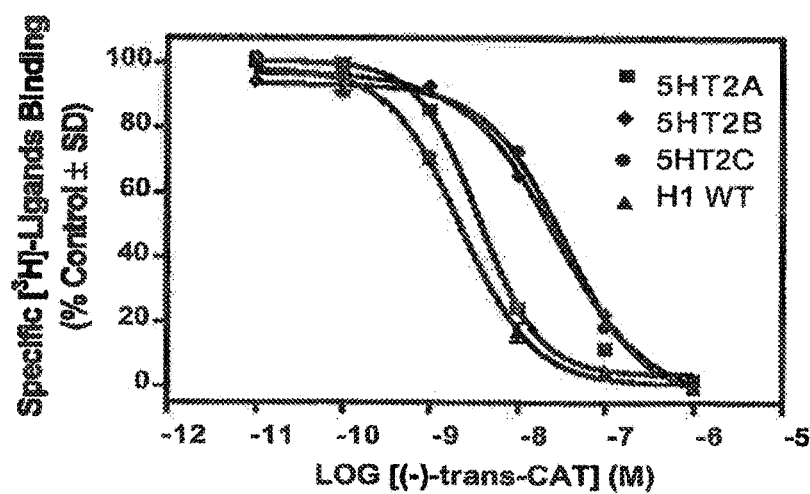

Binding of (-)-*trans*-CAT and (+)-*trans*-CAT to wild type receptors of 5HT2A

Binding of (-)-*trans*-CAT and (+)-*trans*-CAT to wild type receptors of 5HT2B

Binding of (-)-trans-CAT and (+)-trans-CAT to wild type receptors of Histamine H1

Representative curves of (-)-trans-CAT effect on activity of PLC activity/IP formation in HEK 293 cells transiently expressing wild type 5HT2A, 5HT2B, 5HT2C receptors. Data shows that (-)-trans-CAT is an inverse agonist of 5HT2A, 5HT2B and 5HT2C receptors.

Histamine activation of Histamine H1 receptor-mediated stimulation of PLC activity/[3H]-IP formation is competitively antagonized by (-)-*trans*-CAT.

trans-2-(4-Biphenyl)vinylboronic acid
526045
C₁₄H₁₃BO₂
MW: 224.06
[352530-23-5]

3-Bromo-2,6-difluorophenylboronic acid
557242
C₆H₄BBrF₂O₂
MW: 236.81
[352535-84-3]

5-Bromo-2,3-difluorophenylboronic acid
635774
C₆H₄BBrF₂O₂
MW: 236.81
[870778-10-8]

2-Bromo-4,5-difluorophenylboronic acid
645281
C₆H₄BBrF₂O₂
MW: 236.81
[849062-34-6]

trans-1-Octen-1-ylboronic acid
521027
C₈H₁₇BO₂
MW: 156.03
[42599-16-6]

2,3,4,6-Tetrafluorophenylboronic acid
680621
C₆H₃BF₄O₂
MW: 193.89
[511295-00-4]

6-Bromo-2-fluoro-3-iodophenyl boronic acid
666793
C₆H₄BBrFIO₂
MW: 344.71

4-Bromo-2,6-difluorophenylboronic acid
557218
C₆H₄BBrF₂O₂
MW: 236.81 trans-1-Heptenylboronic acid
579386
C₇H₁₅BO₂
MW: 142.00

Arylboronic acids

4-Bromo-2,3,5,6-tetrafluorophenylboronic acid
593966
C₆H₂BBrF₄O₂
MW: 272.79

Phenyl-d₅-boronic acid
517860
C₆H₂BD₅O₂
MW: 126.96
[215527-70-1]

Pentafluorophenylboronic acid
465097
C₆H₂BF₅O₂
MW: 211.88
[1582-24-7]

| phenylboronic acid 1,3-propanediol ester<br>341339<br>$C_9H_{11}BO_2$<br>MW: 161.99<br>[4406-77-3] | 4-Nitrophenylboronic acid pinacol ester<br>643890<br>$C_{12}H_{16}BNO_4$<br>MW: 249.07<br>[171364-83-3] | 4-Aminophenylboronic acid pinacol ester<br>518751<br>$C_{12}H_{18}BNO_2$<br>MW: 219.09<br>[214360-73-3] |
|---|---|---|
| 2-Cyanophenylboronic acid 1,3-propanediol ester<br>653934<br>$C_{10}H_{10}BNO_2$<br>MW: 187.00<br>[172732-52-4] | 4-Amino-3-nitrophenylboronic acid pinacol ester<br>651613<br>$C_{12}H_{17}BN_2O_4$<br>MW: 264.09<br>[893426-94-5] | 2,6-Difluoro-4-formylphenylboronic acid pinacol ester<br>663514<br>$C_{13}H_{15}BF_2O_3$<br>MW: 268.06<br>[870717-92-3] |
| 4-formylphenylboronic acid neopentyl glycol ester<br>632686<br>$C_{12}H_{15}BO_3$<br>MW: 208.04<br>[225916-39-2] | phenylboronic acid pinacol ester<br>647098<br>$C_{12}H_{17}BO_2$<br>MW: 204.07<br>[24388-23-6] | 3-Cyanophenylboronic acid pinacol ester<br>578401<br>$C_{13}H_{16}BNO_2$<br>MW: 229.08<br>[214360-46-0] |
| phenylboronic acid neopentyl glycol ester<br>632678<br>$C_{11}H_{15}BO_2$<br>MW: 190.05<br>[5123-13-7] | 2-Hydroxyphenylboronic acid pinacol ester<br>522554<br>$C_{12}H_{17}BO_3$<br>MW: 220.07<br>[269409-97-4] | 4-Cyanophenylboronic acid pinacol ester<br>527556<br>$C_{13}H_{16}BNO_2$<br>MW: 229.08<br>[171364-82-2] |

| | | | | |
|---|---|---|---|---|
| AAK1 | BRSK2 | | DAPK2 | | JAK2(JH1domain-catalytic) |
| ABL1(E255K)-phosphorylated | BTK | | DAPK3 | ERK8 | JAK3(JH1domain-catalytic) |
| ABL1(F317I)-nonphosphorylated | CAMK1 | | DCAMKL1 | ERN1 | JNK1 |
| ABL1(F317I)-phosphorylated | CAMK1D | | DCAMKL2 | FAK | JNK2 |
| ABL1(F317L)-nonphosphorylated | CAMK1G | | DCAMKL3 | FER | JNK3 |
| ABL1(F317L)-phosphorylated | CAMK2A | | DDR1 | FES | KIT |
| ABL1(H396P)-nonphosphorylated | CAMK2B | | DDR2 | FGFR1 | KIT(A829P) |
| ABL1(H396P)-phosphorylated | CAMK2D | | DLK | FGFR2 | KIT(D816H) |
| ABL1(M388P)-phosphorylated | CAMK2G | | DMPK | FGFR3 | KIT(D816V) |
| ABL1(M351T)-phosphorylated | CAMK4 | | DMPK2 | FGFR3(G697C) | KIT(L576P) |
| ABL1(Q252H)-nonphosphorylated | CAMKK1 | | DRAK1 | FGFR4 | KIT(V559D) |
| ABL1(Q252H)-phosphorylated | CAMKK2 | | DRAK2 | FGR | KIT(V559D,T670I) |
| ABL1(T315I)-nonphosphorylated | CASK | | DYRK1A | FLT1 | KIT(V559D,V654A) |
| ABL1(T315I)-phosphorylated | CDC2L1 | | DYRK1B | FLT3 | LATS1 |
| ABL1(T351)-phosphorylated | CDC2L2 | | DYRK2 | FLT3(D835H) | LATS2 |
| ABL1(Y253F)-phosphorylated | CDC2L5 | | EGFR | FLT3(D835Y) | LCK |
| ABL1-nonphosphorylated | CDK11 | | EGFR(E746-A750del) | FLT3(ITD) | LIMK1 |
| ABL1-phosphorylated | CDK2 | | EGFR(G719C) | FLT3(K663Q) | LIMK2 |
| ABL2 | CDK3 | | EGFR(G719S) | FLT3(N841I) | LKB1 |
| ACVR1 | CDK4-cyclinD1 | | EGFR(L747-E749del, A750P) | FLT3(R834Q) | LOK |
| ACVR1B | CDK4-cyclinD3 | | EGFR(L747-S752del, P753S) | FLT4 | LRRK2 |
| ACVR2A | CDK5 | | EGFR(L747-T751del, Sins) | FRK | LRRK2(G2019S) |
| ACVR2B | CDK7 | | EGFR(L858R) | PYN | LTK |
| ACVRL1 | CDK8 | | EGFR(L858R,T790M) | GAK | LYN |
| ADCK3 | CDK9 | | EGFR(L861Q) | GcNx2(Kin.Dom.2,S808G) | LZK |
| ADCK4 | | | EGFR(S752-I759del) | | |

| Column 1 | Column 2 | Column 3 | Column 4 |
|---|---|---|---|
| AKT1 | CDKL1 | EGFR(T790M) | GRK1 | MAK |
| AKT2 | CDKL2 | EIF2AK1 | GRK4 | MAP3K1 |
| AKT3 | CDKL3 | EPHA1 | GRK7 | MAP3K15 |
| ALK | CDKL5 | EPHA2 | GSK3A | MAP3K2 |
| AMPK-alpha1 | CHEK1 | EPHA3 | GSK3B | MAP3K3 |
| AMPK-alpha2 | CHEK2 | EPHA4 | HCK | MAP3K4 |
| ANKK1 | CIT | EPHA5 | HPK1 | MAP4K2 |
| ARK5 | CLK1 | EPHA6 | HPK2 | MAP4K3 |
| ASK1 | CLK2 | EPHA7 | HPK3 | MAP4K4 |
| ASK2 | CLK3 | EPHA8 | HPK4 | MAP4K5 |
| AURKA | CLK4 | EPHB1 | HPK1 | MAPKAPK2 |
| AURKB | CSF1R | EPHB2 | HUNK | MAPKAPK5 |
| AURKC | CSK | EPHB3 | ICK | MARK1 |
| AXL | CSNK1A1 | EPHB4 | IGF1R | MARK2 |
| BIKE | CSNK1A1L | EPHB6 | IKK-alpha | MARK3 |
| BLK | CSNK1D | ERBB2 | IKK-beta | MARK4 |
| BMPR1A | CSNK1E | ERBB3 | IKK-epsilon | MAST1 |
| BMPR1B | CSNK1G1 | ERBB4 | INSR | MEK1 |
| BMPR2 | CSNK1G2 | ERK1 | INSRR | MEK2 |
| BMX | CSNK1G3 | ERK2 | IRAK1 | MEK3 |
| BRAF | CSNK2A1 | ERK3 | IRAK3 | MEK4 |
| BRAF(V600E) | CSNK2A2 | ERK4 | IRAK4 | MEK5 |
| BRK | CTK | ERK5 | ITK | MEK6 |
| BRSK1 | DAPK1 | | JAK1(JH1domain-catalytic) | MELK |
| | | | JAK1(JH2domain-pseudokinase) | |

FIG. 5 (continued)

| Column 1 | Column 2 | Column 3 | Column 4 |
|---|---|---|---|
| MERTK | PAK7 | PRKD3 | SRPK1 |
| MET | PCTK1 | PRKCQ | SRPK2 |
| MET(M1250T) | PCTK2 | PRKD1 | SRPK3 |
| MET(Y1235D) | PCTK3 | PRKD2 | STK16 |
| MINK | PDGFRA | PRKD3 | STK33 |
| MKK7 | PDGFRB | PRKG1 | STK35 |
| MKNK1 | PDPK1 | PRKG2 | STK38 |
| MKNK2 | PFCDPK1(P.falciparum) | PRKR | STK39 |
| MLCK | PFPK5(P.falciparum) | PRKX | SYK |
| MLK1 | PFTAIRE2 | PRP4 | TAK1 |
| MLK2 | PFTK1 | PYK2 | TAOK1 |
| MLK3 | PHKG1 | QSK | TAOK2 |
| MRCKA | PHKG2 | RAF1 | TAOK3 |
| MRCKB | PIK3C2B | RET | TBK1 |
| MST1 | PIK3C2G | RET(M918T) | TEC |
| MST1R | PIK3CA | RET(V804L) | TESK1 |
| MST2 | PIK3CA(C420R) | RET(V804M) | TGFBR1 |
| MST3 | PIK3CA(E542K) | RIOK1 | TGFBR2 |
| MST4 | PIK3CA(E545A) | RIOK2 | TIE1 |
| MTOR | PIK3CA(E545K) | RIOK3 | TIE2 |
| MUSK | PIK3CA(H1047L) | RIPK1 | TLK1 |
| MYLK | PIK3CA(H1047Y) | RIPK2 | TLK2 |
| MYLK2 | PIK3CA(I800L) | RIPK4 | TNIK |
| MYLK4 | PIK3CA(M1043I) | | TNK1 |

| | | |
|---|---|---|
| MYO3A | PIK3CA(Q546K) | RIPK5 |
| MYO3B | PIK3CB | ROCK1 |
| NDR1 | PIK3CD | ROCK2 |
| NDR2 | PIK3CG | ROS1 |
| NEK1 | PIK4CB | RPS6KA4(Kin.Dom.1-N-terminal) |
| NEK11 | PIM1 | RPS6KA4(Kin.Dom.2-C-terminal) |
| NEK2 | PIM2 | RPS6KA5(Kin.Dom.1-N-terminal) |
| NEK3 | PIM3 | RPS6KA5(Kin.Dom.2-C-terminal) |
| NEK4 | PIP5K1A | RSK1(Kin.Dom.1-N-terminal) |
| NEK5 | PIP5K1C | RSK1(Kin.Dom.2-C-terminal) |
| NEK6 | PIP5K2B | RSK2(Kin.Dom.1-N-terminal) |
| NEK7 | PIP5K2C | RSK3(Kin.Dom.1-N-terminal) |
| NEK9 | PKAC-alpha | RSK3(Kin.Dom.2-C-terminal) |
| NIM1 | PKAC-beta | RSK4(Kin.Dom.1-N-terminal) |
| NLK | PKMYT1 | RSK4(Kin.Dom.2-C-terminal) |
| OSR1 | PKN1 | S6K1 |
| p38-alpha | PKN2 | SBK1 |
| p38-beta | PKNB(M.tuberculosis) | SgK110 |
| p38-delta | PLK1 | SGK3 |
| p38-gamma | PLK2 | SIK |
| PAK1 | PLK3 | SIK2 |
| PAK2 | PLK4 | SLK |
| PAK3 | PRKCD | SNARK |
| PAK4 | PRKCE | SNRK |
| PAK6 | PRKCH | SRC |
| | | SRMS |

| | |
|---|---|
| TNK2 | |
| TNNI3K | |
| TRKA | |
| TRKB | |
| TRKC | |
| TRPM6 | |
| TSSK1B | |
| TTK | |
| TXK | |
| TYK2(JH1domain-catalytic) | |
| TYK2(JH2domain-pseudokinase) | |
| TYRO3 | |
| ULK1 | |
| ULK2 | |
| ULK3 | |
| VEGFR2 | |
| VRK2 | |
| WEE1 | |
| WEE2 | |
| YANK1 | |
| YANK2 | |
| YANK3 | |
| YES | |
| YSK1 | |
| YSK4 | |

FIG. 5 (continued)

THERAPEUTIC TETRAHYDRONAPHTHALENE COMPOUNDS

PRIORITY CLAIM

This application is a Divisional Application of U.S. application Ser. No. 13/318,877, filed Nov. 4, 2011, which is a U.S. National stage Application of PCT International Application No. PCT/US2010/001333, filed on May 5, 2010, which claims the benefit of U.S. Provisional Application No. 61/215,504, filed on May 5, 2009, U.S. Provisional application 61/241,384, filed on Sep. 10, 2009, and U.S. Provisional application 61/277,408, filed on Sep. 24, 2009. The entire contents of each of the above applications are incorporated herein.

STATEMENT OF RIGHTS TO INVENTIONS MADE UNDER FEDERALLY SPONSORED RESEARCH

This invention was made with government support under Grant Nos. MH068655, DA023928 and MH081193 awarded by the National Institute of Health. The government has certain rights in the invention.

BACKGROUND OF THE INVENTION

Serotonin (5-hydroxytryptamine, 5HT) mediates a wide variety of central and peripheral psychological and physiological effects through 14 mammalian 5HT receptor subtypes that are grouped into the $5HT_1$-$5HT_7$ families (Sanders-Bush and Mayer, 2006). The $5HT_2$ family consists of the $5HT_{2A}$, $5HT_{2B}$, and $5HT_{2C}$ membrane-bound G protein-coupled receptors (GPCRs) that signal primarily through $G\alpha_g$ to activate phospholipase (PL) C and formation of inositol phosphates (IP) and diacylglycerol (DAG) second messengers (Raymond et al., 2001). The human $5HT_{2C}$ receptor (Saltzman et al., 1991) apparently is found exclusively in brain where it is widely expressed and putatively involved in several (patho-)physiological and psychological processes, including, ingestive behavior (Tecott et al., 1995), cocaine addiction (Fletcher et al., 2002; Rocha et al., 2002; Muller and Huston, 2006), sleep homeostasis (Frank et al., 2002), anxiety (Kennett et al., 1994; Sard et al., 2005; Heisler et al., 2007), depression (Tohda et al., 1989; Palvimaki et al., 1996), epilepsy (Heisler et al., 1998), Alzheimer's disease (Arjona et al., 2002; Stein et al., 2004), motor function (Heisler and Tecott, 2000; Segman et al., 2000), psychosis (Marquis et al., 2007; Siuciak et al., 2007) and response to antipsychotic drugs (Veenstra-VanderWeele et al., 2000; Reynolds et al., 2005). Thus, the importance of the $5HT_{2C}$ receptor as a pharmacotherapeutic target has been apparent for about 10 years, however, no $5HT_{2C}$-specific drugs have been developed.

One challenge regarding drug discovery targeting the $5HT_{2C}$ receptor is that this GPCR shares a transmembrane domain (TMD) sequence identity of about 80% with the $5HT_{2A}$ receptor and about 70% with the $5HT_{2B}$ receptor (Julius et al., 1988; 1990). The highly conserved TMDs and similar second messenger coupling has made development of agonist ligands selective for the $5HT_{2C}$ receptor especially difficult. Nevertheless, there is compelling evidence that activation of $5HT_{2C}$ receptors reduces food intake and leads to anti-obesity effects. For example, 5-$HT_{2C}$ knockout mice demonstrate increased feeding and obesity, and, they are resistant to the anorectic effects of d-fenfluramine (Tecott et al., 1995; Vickers et al., 1999; 2001; Heisler et al., 2002). Fenfluramine now is banned, because, although people using the drug showed weight loss due to activation of brain $5HT_{2C}$ receptors, fenfluramine also activates $5HT_{2A}$ receptors that may lead to adverse psychiatric (hallucinogenic) effects (Nichols, 2004) and $5HT_{2B}$ receptors which causes valvular heart disease (Connolly et al., 1997; Fitzgerald et al., 2000; Rothman et al., 2000; Roth, 2007) and pulmonary hypertension (Pouwels et al., 1990; Launay et al., 2002)—fatalities have resulted from the $5HT_{2B}$-mediated effects.

Although an agonist ligand truly selective for $5HT_{2C}$ vs. $5HT_{2A}$ and/or $5HT_{2B}$ receptors has not been reported until this paper, it has been possible to partially elucidate the role of brain $5HT_{2C}$ receptors to attenuate cocaine use and dependence using very selective (i.e., at least 100-fold) $5HT_{2A}$ and $5HT_{2C}$ antagonists in rat cocaine self-administration paradigms. For example, the selective $5HT_{2A}$ antagonist M100907 (Kehne et al., 1996) does not alter responding rate for cocaine self-administration but the selective $5HT_{2C}$ antagonist SB242084 (Bromidge et al., 1997) increases the rate of cocaine self-administration dose-dependently (Fletcher et al., 2002). The tremendous potential of $5HT_{2C}$ agonist pharmacotherapy for psychostimulant addiction now is widely recognized (Bubar and Cunningham, 2006).

The pharmacotherapeutic relevance of the $5HT_{2C}$ receptor in obesity and neuropsychiatric disorders such as psychostimulant addiction has stimulated intense interest by pharmaceutical companies to develop a selective $5HT_{2C}$ agonist, however, all $5HT_{2C}$ agonists reported so far also activate $5HT_{2A}$ and/or $5HT_{2B}$ receptors (Nilsson, 2006). Nevertheless, the $5HT_2$ agonist lorcaserin (APD356) recently went to Phase III clinical trials for obesity treatment even though it has only a modest 15-fold selectivity for activation of $5HT_2c$ receptors over $5HT_{2A}$ receptors (Jensen, 2006; Smith et al., 2006). Results reported here, however, are based on novel compounds synthesized in our laboratories, i.e., phenyl-3-dimethylamino-1,2,3,4-tetrahydronaphthalene (PAT) and cyclyl-3-dimethylamino-1,2,3,4-tetrahydronaphthalene (CAT) compounds, are full efficacy agonist at human $5HT_{2C}$ receptors, plus, it is an antagonist at $5HT_{2A}$ and $5HT_{2B}$ receptors.

G Protein-Coupled Receptors (GPCRs) can activate more than more type of G protein that results in multiple physiological/pharmacological effects, both pharmacotherapeutic and untoward side effects (Moniri et al., *Journal of Pharmacology and Experimental Therapeutics*, 311:274-281 (2004)). The phenomenon of multiple signaling pathways associated with a single GPCR can be described within the framework of the three-state model of GPCR activation, wherein, GPCRs isomerize between inactive and constitutively active states. GPCR activation causes dissociation of heterotrimeric $(\alpha,\beta,\gamma)$ G protein subunits—the G$\alpha$ subunit can then activate transducer protein (e.g., PLC, AC) to alter second messenger concentration. It is now realized the same GPCR can couple to different G$\alpha$ proteins to result in "multifunctional signaling". A critical assumption of the GPCR multifunctional signaling theory is that a heterogeneity of active receptor conformations exists and that agonist ligands differ in their ability to induce, stabilize, or select among receptor conformations, as described in the "stimulus trafficking" hypothesis. It follows that, upon binding, agonist ligand chemical structural parameters are among the most important determinants of GPCR conformation that influences type of G$\alpha$ protein and signaling pathway activated.

A survey of 105 articles on the activity of 380 antagonists on 73 biological G-protein-coupled receptor targets indicates that, in this sample dataset, 322 are inverse agonists and 58 (15%) are neutral antagonists. The predominance of inverse agonism agrees with theoretical predictions which indicate that neutral antagonists are the minority species in pharmacological space (Kenakin, Mol Pharmacol. (2004); 65:2-11).

The p90 ribosomal s6 kinases (RSKs) are a group of serine/threonine kinases that are constituents of the AGC subfamily in the human kinome (Nguyen, 2008). There are four RSK isoforms (RSK1-4) and each is a product of a separate gene. The RSK isoforms are characterized by 75%-80% sequence identity. Although the RSK isoforms are broadly distributed in human tissue, they exhibit variable tissue expression, which is an indication that they may be involved in different functions. The RSK isoforms are activated by extracellular signaling molecules that stimulate the Ras-ERK pathway. These molecules include a variety of different growth factors, cytokines, peptide hormones and neurotransmitters. It is noted that at this time, biological/pharmacological roles for each of the RSK isoforms is not established for most diseases, including, cancer.

RSKs phosphorylate a variety of proteins, including transcription factors, immediate-early gene products, translational regulators, enzymes, and structural proteins, that link RSKs as a family to many biological processes such as cell proliferation, cell differentiation, survival, and migration (Anjum and Blenis, 2008a).

RSK isoforms are overexpressed in 50% of human breast cancer tissue samples, indicating that regulation of RSK has been compromised—the link between RSK activity and tumor cell proliferation reveals RSKs as novel cancer drug targets (Gioeli et al., 1999; Smith et al., 2005).

There is compelling evidence for a link between RSKs and HIV infection. RSK2 was shown to have a reciprocal relationship with HIV-1 Tat. RSK2 is recruited and activated by HIV-1 Tat, and is itself also important to normal Tat function (Hetzer et al., 2005). Moreover, Kaposi sarcoma-associated herpesvirus interacts with RSKs and strongly stimulates their kinase activities (Kuang et al., 2009).

Structurally, the RSK isoforms are very similar (Nguyen, 2008). Each of the isoforms contains two functional catalytic domains that are separated by a large 100 amino acid linker region. The two kinase domains are distinct and contain nonidentical ATP-binding site. The NTKD is similar to p70 S6 kinase (p70 S6K1), and the CTKD is similar to the calcium/calmodulin protein kinases. Because of its molecular architecture, RSK offers two logical sites for inhibition: the ATP-binding site in the NTKD and the one in the CTKD. Site specific inhibitors for both ATP pockets have been identified.

Aberrant activation of the upstream activators of 90 kDa ribosomal S6 kinase (RSK) has been linked to many human diseases, including cancers. The RSK1 and RSK2 isoforms are amplified in breast and prostate tumours. The importance of RSK2 activation in haematopoietic transformation was recently shown in fibroblast growth factor receptor-3 (FGFR3)-expressing multiple myeloma cells. RSK3 was recently shown to function as a potential tumour suppressor in ovarian cancer. RSK4 was shown to participate in p53-dependent cell growth arrest, although aberrant expression of RSK4 has been observed in breast cancer. Mutations in the human RSK2 gene are associated with Coffin-Lowry syndrome (CLS), an X-linked disorder that is characterized by severe psychomotor retardation, digit and facial dysmorphisms, and progressive skeletal deformations. In fibroblasts from CLS patients, a drastic attenuation in induced Ser133 phosphorylation of the transcription factor CREB was detected in response to epidermal growth factor stimulation. Fibroblasts that were derived from patients with CLS have been useful in determining the function of RSK2 with respect to this human disease; however, differences found between these cells and RSK2-deficient mouse fibroblasts suggest that CLS might be a multivariable disease and mouse might not be the ideal system in which to study RSK2 function. Both the RSK2 and RSK4 genes are located on chromosome X, and recent data also implicate RSK4 in nonspecific X-linked mental retardation, but definitive evidence remains to be provided for RSK4 (Anjum and Blenis, 2008b).

SUMMARY OF THE INVENTION

In one aspect, the invention provides a method of treating a subject suffering from or susceptible to a neuropsychiatric disorder comprising administering to subject in need thereof a therapeutically effective amount of a compound (e.g., compounds delineated herein) capable of modulating 5-HT2 binding interactions. In one embodiment, the compound is capable of agonizing a 5-HT2c. In another embodiment, the compound is capable agonizing a 5-HT2c, while antagonizing 5-HT2a and/or 5-HT2b.

In one aspect, the invention provides a method of treating a subject suffering from or susceptible to a neuropsychiatric disorder. The method includes administering to a subject in need thereof a therapeutically effective amount of a 5-HT2c agonizing compound.

In another aspect, the invention provides a method of treating a subject suffering from or susceptible to a neuropsychiatric disorder. The method includes administering to a subject in need thereof a therapeutically effective amount of a compound capable of modulating 5-HT2 binding interactions by directly modulating 5-HT2c, preferably selectively relative to 5-HT2a and/or 5-HT2b.

In another embodiment, the invention provides a method of treating a subject suffering from or susceptible to a neuropsychiatric disorder. The method includes administering to a subject identified as in need thereof a therapeutically effective amount of a 5-HT2c agonizing compound or a 5-HT2c selective compound.

In another aspect, the invention provides a method of treating a subject suffering from or susceptible to a neuropsychiatric disorder, including obesity, addiction, cocaine addiction, amphetamine/methamphetamine addiction, psychosis, anxiety, sleep homeostasis. The method includes administering to a subject agonizing 5-HT2c.

In another aspect, the invention provides a method of treating a subject suffering from or susceptible to obesity, addiction, cocaine addiction, amphetamine/methamphetamine addiction, psychosis, anxiety comprising administering to the subject an effective amount of a compound capable of agonizing 5-HT2c (including selectively relative to 5-HT2a and/or 5-HT2b), such that the subject is treated.

In one aspect, the invention provides a method of treating a subject suffering from or susceptible to a GPCR disorder comprising administering to subject in need thereof a therapeutically effective amount of a compound capable of modulating GPCR binding interactions. In one embodiment, the compound is capable of agonizing a GPCR. In another embodiment, the compound is capable antagonizing a GPCR.

In another aspect, the compounds herein are functionally selective compounds that target serotonin histamine $H_1$, 5HT$_{2A, 2B, 2C}$, and acetylcholine muscarinic M$_1$-M$_5$ GPCRs. In aspects, the invention provides a method to selectively target serotonin histamine H$_1$, 5HT$_{2A, 2B, 2C}$, and acetylcholine muscarinic M$_1$-M$_5$ GPCRs in a subject comprising administering to the subject a compound herein.

In another aspect, the invention provides a method of treating or preventing a GPCR-mediated disorder in a subject comprising administering to the subject identified as in need thereof a compound delineated herein. In certain embodiments, the compound is a compound of Table 1 (infra). In certain embodiments, the compound is represented by the formula (I):

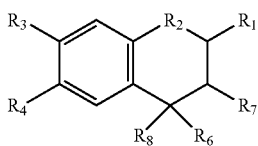

(I)

wherein,

R$_1$ is independently H, NH$_2$, NH(R'), N(R')$_2$;
or

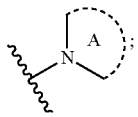

wherein ring A is a 3-8 membered heterocyclic or heteroaryl, containing 0-3 additional heteroatoms selected from O, N and S; wherein ring A is optionally substituted;

each R' is independently alkyl, alkenyl, or alkynyl, each of which may be optionally substituted;

R$_2$ is independently —(CH$_2$)n-;
each n is independently 1 or 2;
R$_3$ is independently H, OH, or halo;
R$_4$ is independently H, OH, or halo
each R$_5$ is independently alkyl, aryl, halo, nitro, amino, heteroaryl, cycloalkyl, heterocyclic, or alkoxy;
R$_6$ is independently H or alkyl;
R$_7$ independently H, or N(alkyl)$_2$; and
each R$_8$ is independently aryl, cycloalkyl, heteroaryl, or heterocyclic, optionally substituted with 1, 2, 3, or 4 independent R$_5$;
or salt, hydrate or solvate thereof.

In certain embodiments, the compound is that wherein each R$_1$ is —NMe$_2$.

In other embodiments, R$_1$ is

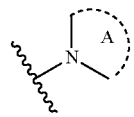

which is optionally substituted;

In certain embodiments, the compound is that wherein each R$_5$ is not H, alkyl, or halo.

In certain embodiments, the compound is that wherein R$_8$ is substituted with one R$_5$, R$_5$ is a substitutent not H, alkyl, or halo.

In certain embodiments, the compound is that wherein R$_8$ is optionally substituted (e.g., substituted, unsubstituted) cycloalkyl.

In certain embodiments, the compound is that wherein R$_8$ is optionally substituted (e.g., substituted, unsubstituted) aryl.

In certain embodiments, the compound is that wherein each R$_8$ is independently aryl or cycloalkyl, wherein each R$_8$ is substituted with 2, 3 or 4 independent R$_5$ wherein each R$_5$ is independently H, alkyl, halo, aryl, nitro, amino, heteroaryl, cycloalkyl.

In certain embodiments, the invention provides a method of treating a disease, disorder, or symptom thereof in a subject identified as in need of such treatment, comprising administering a compound delineated herein.

In certain embodiments, the disorder is a neuropsychiatric disorder (e.g., obesity, addiction, cocaine addiction, amphetamine/methamphetamine addiction, anxiety, depression, schizophrenia, and sleep disorders), a neurodegenerative disorder (e.g., Parkinson's Disease, Alzheimer's Disease), a neurological disorder (e.g., epilepsy), a cardiovascular disorder (e.g., hypertension), a gastrointestinal disorder (e.g., irritable bowel syndrome), or a genitor-urinary tract disorder (e.g., bladder control). In certain embodiments, the disorder is psychostimulant (e.g., cocaine, amphetamine, methamphetamine) drug addiction. In certain embodiments, the disorder is obesity. In certain embodiments, the disorder is cognitive dysfunction. In other embodiments, the disorder is allergy or inflammatory disorders.

In another aspect, the invention provides a method of inhibiting 5-HT2$_C$ in a subject identified as in need of such treatment, comprising administering a compound delineated herein.

In another aspect, the invention provides a method of treating obesity in a subject, comprising administering to the subject identified as in need thereof a compound capable of selectively inhibiting the 5-HT2c relative to 5-HT2a or 5-HT2b. In certain embodiments, the binding interaction the for inhibiting 5-HT2c is at least 5-fold (alternatively at least 10-fold, 15-fold, 20-fold, 50-fold, 100-fold, 500 fold) greater than for either 5-HT2a or 5-HT2b. In certain embodiments, the binding interaction for inhibiting 5-HT2c is at least 100-fold greater than for either 5-HT2a or 5-HT2b.

In another aspect, the invention provides a method for identifying a compound that is capable of modulating 5-HT2c activity, comprising; (i) producing a three-dimensional representation of a molecule or molecular complex, wherein said molecule or molecular complex comprises a binding pocket defined by structure coordinates of 5-HT2c; or b) a three-dimensional representation of a homologue of said molecule or molecular complex, wherein said homologue comprises a binding pocket that has a root mean square deviation from the backbone atoms of said amino acids of not more than about 2.0 angstroms; (ii) producing a three-dimensional representation of a test compound; (iii) assessing the binding interaction of the test compound with the target. In certain embodiments, the method further comprises contacting the test compound with a 5-HT2c and measuring the binding activity of the compound.

In one aspect, the invention provides a method of treating a subject suffering from or susceptible to a disease or disorder comprising administering to subject in need thereof a therapeutically effective amount of a compound (e.g., compounds of any of the formulae delineated herein) capable of modulating RSK binding interactions.

In one aspect, the invention provides a method of treating a subject suffering from or susceptible to a disease or disorder. The method includes administering to a subject in need thereof a therapeutically effective amount of a RSK inhibitor compound.

In another aspect, the invention provides a method of treating a subject suffering from or susceptible to a RSK-mediated disease or disorder. The method includes administering to a subject in need thereof a therapeutically effective amount of a compound of any of the formulae delineated herein (e.g., RSK modulating compound (direct or indirect), RSK inhibitor compound).

In another aspect, the invention provides a method of treating a subject suffering from or susceptible to a disease or disorder. The methods include administering to a subject identified as in need thereof a therapeutically effective amount of a compound selective for inhibiting RSK over one or more other kinases (e.g., a compound delineated herein). The methods include administering to a subject identified as in need thereof a therapeutically effective amount of a compound identified as selective for inhibiting RSK over one or more other kinases (e.g., a compound delineated herein). The methods include administering to a subject identified as in need thereof a therapeutically effective amount of a compound selective for inhibiting RSK-1, -3 or -4 over RSK-2 (e.g., a compound delineated herein). The methods include administering to a subject identified as in need thereof a therapeutically effective amount of a compound for modulating RSK-2 (e.g., a compound delineated herein) by modulation (e.g., inverse agonist activity) of 5-HT2 (e.g., 5-HT2a, 5-HT2b, 5-HT2c). The method can be that wherein the compound is identified as modulating RSK-2 (e.g., a compound delineated herein) by modulation (e.g., inverse agonist activity) of 5-HT2 (e.g., 5-HT2a, 5-HT2b, 5-HT2c).

In other aspects, the methods include those wherein the compounds are selective for RSK-1, -3 or -4 over other kinases. The selectivity is e.g., 2-fold, 3-fold, 10-fold, 100-fold, X-fold (wherein X is a number), etc. for one target (i.e., a kinase) relative to another target. In another embodiment, the invention provides a method as described herein wherein the compound demonstrates selectivity for an activity range against a target enzyme and an different activity range against an off-target enzyme.

In other aspects, the methods include those wherein the compounds preferentially, inhibit RSKs 1 and especially 3, and 4, over RSK2 or other kinases. In other aspects, the methods include those wherein the compounds preferentially, inhibiting RSKs 1 and especially 3, and 4 and no inhibition of RSK 2 at 1.0 micromolar concentration. As such, (−)-trans-CAT and derivatives are highly valuable as a molecular biochemical tools to distinguish physical and biological properties of RSKs 1, 3, and 4 from RSK 2, and, to distinguish the biology of RSKs 1,3,4 from 438 other kinases (see Table 4); and as as a molecular biochemical tools to distinguish physical and biological properties of RSKs 1, 3, and 4 from RSK 2, and, to distinguish the biology of RSKs 1,3,4 from 438 other kinases; and are useful to characterize the biology and pathology of cancer (especially hematopoietic, breast and prostate), HIV, and Coffin-Lowry syndrome regarding the involvement of one RSK isoform vs. another in these diseases, and vs. other kinases in these diseases. Additionally, (−)-Trans-CAT and the compounds herein, by virtue of their binding interactions with RSK 1, 3, and 4, are valuable biochemical probes to characterize the structure of these kinases.

In certain embodiments, the invention provides a method described above wherein the compound is represented by the formula (I):

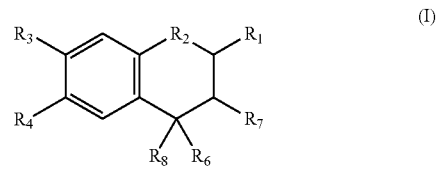

wherein,
$R_1$ is independently H, $NH_2$, $NH(R')$, $N(R')_2$;
or

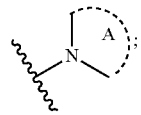

wherein ring A is a 3-8 membered heterocyclic or heteroaryl, containing 0-3 additional heteroatoms selected from O, N and S; wherein ring A is optionally substituted;
each R' is independently alkyl, alkenyl, or alkynyl, each of which may be optionally substituted;
$R_2$ is independently $-(CH_2)n-$;
each n is independently 1 or 2;
$R_3$ is independently H, OH, or halo;
$R_4$ is independently H, OH, or halo
each $R_5$ is independently alkyl, aryl, halo, nitro, amino, heteroaryl, cycloalkyl, heterocyclic, or alkoxy;
$R_6$ is independently H or alkyl;
$R_7$ independently H, or $N(alkyl)_2$; and
each $R_8$ is independently aryl, cycloalkyl, heteroaryl, or heterocyclic, optionally substituted with 1, 2, 3, or 4 independent $R_5$;
or salt, hydrate or solvate thereof.

In certain embodiments, the compound is that wherein each $R_1$ is $-NMe_2$.

In certain embodiments, $R_1$ is

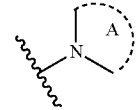

which is optionally substituted.

In certain embodiments, the compound is that wherein each $R_5$ is not H, alkyl, or halo.

In certain embodiments, the compound is that wherein $R_8$ is substituted with one $R_5$, $R_5$ is a substitutent not H, alkyl, or halo.

In certain embodiments, the compound is that wherein $R_8$ is optionally substituted (e.g., substituted, unsubstituted) cycloalkyl.

In certain embodiments, the compound is that wherein $R_8$ is optionally substituted (e.g., substituted, unsubstituted) aryl.

In certain embodiments, the compound is that wherein each $R_8$ is independently aryl or cycloalkyl, wherein each $R_8$ is substituted with 2, 3 or 4 independent $R_5$ wherein each $R_5$ is independently H, alkyl, halo, aryl, nitro, amino, heteroaryl, cycloalkyl.

In certain embodiments, the invention provides a method of treating a disease, disorder, or symptom thereof in a subject identified as in need of such treatment, comprising administering a compound delineated herein. In one aspect the compound is (−)-trans-CAT.

In certain embodiments, the disorder is cancer (especially hematopoietic, breast and prostate), HIV, or Coffin-Lowry syndrome. In certain embodiments, the disorder is breast cancer. In certain embodiments, the disorder is prostate cancer. In certain embodiments, the disorder is HIV.

In one aspect, the invention provides a compound that is represented by the formula (I):

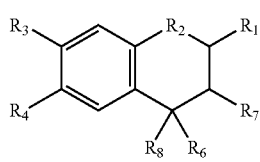
(I)

wherein,
$R_1$ is independently H, $NH_2$, NH(R'), $N(R')_2$;
or

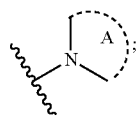

wherein ring A is a 3-8 membered heterocyclic or heteroaryl, containing 0-3 additional heteroatoms selected from O, N and S; wherein ring A is optionally substituted;
each R' is independently alkyl, alkenyl, or alkynyl, each of which may be optionally substituted;
$R_2$ is independently —$(CH_2)n$-;
each n is independently 1 or 2;
$R_3$ is independently H, OH, or halo;
$R_4$ is independently H, OH, or halo
each $R_5$ is independently alkyl, aryl, halo, nitro, amino, heteroaryl, cycloalkyl, heterocyclic, or alkoxy;
$R_6$ is independently H or alkyl;
$R_7$ independently H, or $N(alkyl)_2$; and
each $R_8$ is independently aryl, cycloalkyl, heteroaryl, or heterocyclic, optionally substituted with 1, 2, 3, or 4 independent $R_5$;
or salt, hydrate or solvate thereof.

In certain embodiments, the compound is that wherein each $R_1$ is —$NMe_2$.

In certain embodiments, $R_1$ is

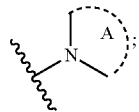

which is optionally substituted;
In certain embodiments, the compound is that wherein each $R_5$ is not H, alkyl, or halo.
In certain embodiments, the compound is that wherein $R_8$ is substituted with one $R_5$, $R_5$ is a substituent not H, alkyl, or halo.
In certain embodiments, the compound is that wherein $R_8$ is optionally substituted (e.g., substituted, unsubstituted) cycloalkyl.

In certain embodiments, the compound is that wherein $R_8$ is optionally substituted (e.g., substituted, unsubstituted) aryl.

In certain embodiments, the compound is that wherein each $R_8$ is independently aryl or cycloalkyl, wherein each $R_8$ is substituted with 2, 3 or 4 independent $R_5$ wherein each $R_5$ is independently H, alkyl, halo, aryl, nitro, amino, heteroaryl, cycloalkyl.

In certain embodiments, the compound substituents at the 1-position and the 3-position are in the trans-orientation to one another.

In certain embodiments, the compound is represented by the formula (II):

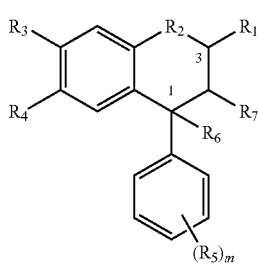
(II)

wherein,
$R_1$ is independently H, $NH_2$, NH(R'), $N(R')_2$;
or

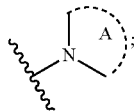

wherein ring A is a 3-8 membered heterocyclic or heteroaryl, containing 0-3 additional heteroatoms selected from O, N and S; wherein ring A is optionally substituted;
each R' is independently alkyl, alkenyl, or alkynyl, each of which may be optionally substituted;
$R_2$ is independently —$(CH_2)n$-;
each n is independently 1 or 2;
$R_3$ is independently H, OH, or halo;
$R_4$ is independently H, OH, or halo;
each $R_5$ is independently alkyl, aryl, halo, nitro, amino, heteroaryl, cycloalkyl, heterocyclic, or alkoxy;
$R_6$ is independently H or alkyl;
$R_7$ independently H, or $N(alkyl)_2$;
m is 1, 2 or 3,
or salt, hydrate or solvate thereof.

In certain embodiments, each R' is independently methyl, ethyl, propyl, iso-propyl, butyl, s-butyl, t-butyl, alkenyl, vinyl, or alkynyl.

In certain embodiments, the compound substituents at the 1-position and the 3-position are in the trans-orientation to one another In certain embodiments, the compound $R_1$ is —$NMe_2$. In certain embodiments, the PAT compound is (1R,3S)-(−)-Trans-1-phenyl-3-N,N-dimethylamino-1,2,3,4-tetrahydronaphthalene.

In a further embodiment, the compound is represented by the formula (II-a):

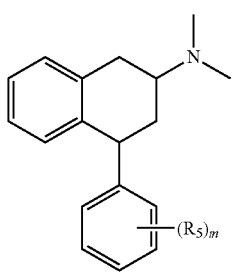

(II-a)

wherein,

R$_5$ is H, methyl, ethyl, propyl, iso-propyl, butyl, s-butyl, t-butyl, cyclopropyl, cyclobutyl, cyclopentyl, cyclohexyl, cycloheptyl, cyclooctyl, phenyl, F, Cl, or Br; and m is 1, 2, or 3;

or salt, hydrate or solvate thereof.

In certain embodiments, the compound is represented by the formula (III):

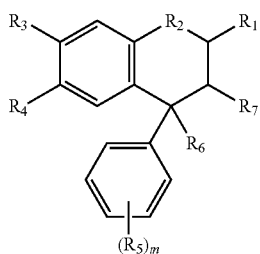

(III)

wherein,

R$_1$ is independently H, NH$_2$, NH(R'), N(R')$_2$;

or

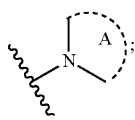

wherein ring A is a 3-8 membered heterocyclic or heteroaryl, containing 0-3 additional heteroatoms selected from O, N and S; wherein ring A is optionally substituted;

each R' is independently alkyl, alkenyl, or alkynyl, each of which may be optionally substituted;

R$_2$ is independently —(CH$_2$)n-;

n is 2;

R$_3$ is independently H, OH, or halo;

R$_4$ is independently H, OH, or halo

R$_5$ is H, alkyl, or halo;

R$_6$ is independently H or alkyl;

R$_7$ is H, or N(alkyl)$_2$; and m is 1, 2, or 3;

or salt, hydrate or solvate thereof.

In another aspect, the invention provides a compound that is represented by the formula (IV):

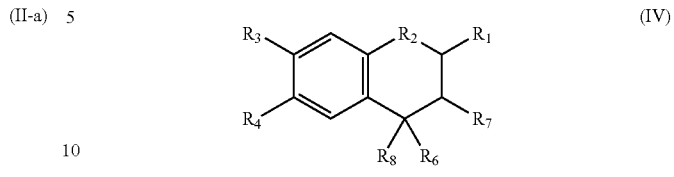

(IV)

wherein,

R$_1$ independently H, or N(alkyl)$_2$;

R$_2$ is independently —(CH$_2$)n-;

each n is independently 1 or 2;

R$_3$ is independently H, OH, or halo;

R$_4$ is independently H, OH, or halo each R$_5$ is independently alkyl, aryl, halo, nitro, amino, heteroaryl, cycloalkyl, heterocyclic, or alkoxy;

R$_6$ is independently H or alkyl;

R$_7$ is independently H, NH$_2$, NH(R'), N(R'1)$_2$;

or

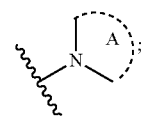

wherein ring A is a 3-8 membered heterocyclic or heteroaryl, containing 0-3 additional heteroatoms selected from O, N and S; wherein ring A is optionally substituted;

each R' is independently alkyl, alkenyl, or alkynyl, each of which may be optionally substituted; and each R$_8$ is independently aryl, cycloalkyl, heteroaryl, or heterocyclic, optionally substituted with 1, 2, 3, or 4 independent R$_5$;

or salt, hydrate or solvate thereof.

In certain embodiments of any of the formulae above, the compound substituents at the 1-position and the 3-position are in the trans-orientation to one another In certain embodiments, the compound R$_1$ is —NMe$_2$. In certain embodiments, the PAT compound is (1R,3S)-(−)-Trans-1-phenyl-3-N,N-dimethylamino-1,2,3,4-tetrahydronaphthalene.

In another aspect, the invention provides a compound that is represented by the formula (V):

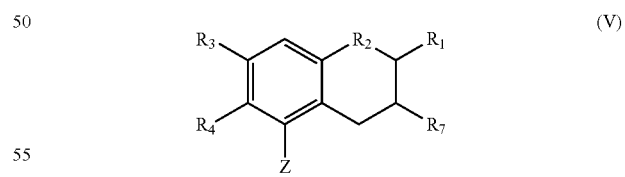

(V)

wherein,

R$_1$ is independently H, NH$_2$, NH(R'), N(R')$_2$;

or

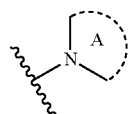

wherein ring A is a 3-8 membered heterocyclic or heteroaryl, containing 0-3 additional heteroatoms selected from O, N and S; wherein ring A is optionally substituted;

each R' is independently alkyl, alkenyl, or alkynyl, each of which may be optionally substituted;

$R_2$ is independently —$(CH_2)n$-;

each n is independently 1 or 2;

$R_3$ is H, OH, or halo;

$R_4$ is H, OH, aryl, heteroaryl, or halo;

each $R_5$ is independently alky, aryl, halo, nitro, amino, heteroaryl, cycloalkyl;

$R_7$ is H, or N(alkyl)$_2$; and

Z is aryl, nitro, amino, heteroaryl, cycloalkyl, each of which is optionally substituted with 1, 2, 3, or 4 independent $R_5$;

or salt, hydrate or solvate thereof.

In certain embodiments, $R_1$ is N(R')$_2$; and each R' is alkyl. In other embodiments, Z is phenyl which may be substituted with haloalky, alkoxy, or halo. In other embodiments, $R_4$ is phenyl which may be substituted with haloalky, alkoxy, or halo.

In another aspect, the invention provides a composition comprising a compound described herein (e.g., a compound of any of the formulae herein) and a pharmaceutically acceptable carrier.

In another aspect, the invention provides a method making a composition comprising combining a compound described herein (e.g., a compound of any of the formulae herein) and a pharmaceutically acceptable carrier.

Results of structure-activity relationship (SAR) studies indicate that affinity selectivity of the invention compounds for $H_1$ vs. $5HT_{2A}$ vs. $5HT_{2B}$ vs. $5HT_{2C}$, vs, $M_1$ vs. $M_2$ vs $M_3$ vs. $M_4$ vs. $M_5$ GPCRs is dependent on the stereochemistry of the substituents at the C1 (e.g., pendant phenyl or other aromatic, heteroaromatic, cyclyl, cycloalkyl) and C3 (amine) positions and, the chemical nature of the C1 and C3 substituents, as well as, the chemical substituents at the C6 and C7 positions of the tetrahydronapthalene ring system (carbon numbering as in Formula I, Table 1). Likewise, agonist vs. inverse agonist vs. antagonist activity at $H_1$ vs. $5HT_{2A}$ vs. $5HT_{2B}$ vs. $5HT_{2C}$, vs, $M_1$ vs. $M_2$ VS. $M_3$ vs. $M_4$ VS. $M_5$ GPCRs is determined by the chemical nature and stereochemistry of the substituents(s) at C1, C3, C6, and C7. See, e.g., Bucholtz, E. C., Wyrick, S. D., Owens, C. E., and Booth, R. G. 1-Phenyl-3-dimethylaminotetralins (PATs): Effect of stereochemistry on binding and function at brain histamine receptors. *Medicinal Chemistry Research* 8:322-332 (1998); Bucholtz, E. C., Brown., R. L., Tropsha, A., Booth, R. G, and Wyrick, S. D. Synthesis, Evaluation and Comparative Molecular Field Analysis of 1-Phenyl-3-amino-1,2,3,4-tetrahydronaphthalenes as Ligands for Histamine $H_1$ Receptors. *Journal of Medicinal Chemistry.* 42:3041-3054 (1999); Choksi, N.Y., Nix, William B., Wyrick, S. D., and Booth, R. G. A novel phenylaminotetralin recognizes histamine $H_1$ receptors and stimulates dopamine synthesis in vivo in rat brain. *Brain Research* 852:151-160 (2000); Booth R G, Moniri N H, Bakker R A, Choksi N Y, Timmerman H, and Leurs R. A novel phenylaminotetralin radioligand reveals a sub-population of histamine $H_1$ receptors. *Journal of Pharmacology and Experimental Therapeutics* 302:328-336 (2002); Moniri N H, Covington-Strachan D, Booth R G. Ligand-directed functional heterogeneity of histamine $H_1$ receptors: Novel dual-function ligands selectively activate and block $H_1$-meditated phospholipas C and adenylyl cyclase signaling. *Journal of Pharmacology and Experimental Therapeutics,* 311:274-281 (2004); Booth R G, Moniri N H. Ligand-directed multifunctional signaling of histamine $H_1$ receptors *Inflammation Research* 54: S44-45 (2005); Ghoneim O M, Legere J A, Glbraikh A, Tropsha A, Booth R G. Novel ligands for the human histamine $H_1$ receptor: Synthesis, pharmacology, and comparative molecular field analysis studies of 2-dimethylamino-5-(6)-phenyl-1,2,3,4-tetrahydronaphthalenes. *Bioorganic and Medicinal Chemistry,* 14:6640-6658 (2006); Booth R G, Moniri N H. Novel Ligands Stabilize Stereo-Selective Conformations of the Histamine H1 Receptor to Activate Catecholamine Synthesis. *Inflammation Research* 56:1-12 (2007).

In another embodiment, the compounds herein can distinguish and selectively activate brain $H_1$ receptors that couple to the adenylyl cyclase (AC)/cAMP vs. phospholipase C (PLC)/inositol phosphates (IP) intracellular signaling pathways to modulate brain catecholamine (dopamine, norepinephrine) neurotransmitter synthesis. In aspects, the invention provides a method of selectively activating brain $H_1$ receptors that couple to the adenylyl cyclase (AC)/cAMP vs. phospholipase C (PLC)/inositol phosphates (IP) intracellular signaling pathways to affect physiologically processes sensitive to $H_1$/AC/cAMP signaling, e.g., modulation brain catecholamine (dopamine, norepinephrine) neurotransmitter synthesis in a subject comprising administering to the subject a compound herein.

In another aspect, the compounds herein are compounds that selectively enhance $H_1$-mediated AC/cAMP signaling to treat a patient suffering from certain neuropsychiatric diseases involving altered catecholamine neurotransmission. In aspects, the invention provides a method of selectively enhancing $H_1$-mediated AC/cAMP signaling to treat a subject suffering from certain neuropsychiatric diseases involving altered catecholamine neurotransmission comprising administering to the subject a compound herein.

In another embodiment, the compounds herein are compounds that are antagonists and inverse agonists of untoward $H_1$-mediated effects that proceed via $H_1$/PLC/IP signaling, e.g., respiratory distress (bronchial constriction), diarrhea (GI contractions), and edema and hypotension (increased vascular permeability), especially associated with the peripheral allergic response. In aspects, the invention provides a method of antagonizing (e.g., blocking) untoward $H_1$-mediated effects that proceed via the PLC/IP pathway in a subject comprising administering to the subject a compound herein.

In another aspect, the compounds herein are antagonists as well as inverse agonists at serotonin $5HT_{2A}$ and $5HT_{2B}$ receptors.

In another embodiment, the compounds herein are antagonists as well as inverse agonists at histamine $H_1$ receptors linked to PLC/IP signaling.

In another aspect, the compounds herein are antagonists as well as inverse agonists at acetylcholine muscarinic $M_1$-$M_5$ receptors.

In another aspect, the compounds herein are antagonists as well as inverse agonists and agonists at acetylcholine muscarinic $M_1$-$M_5$ receptors. In another aspect, the compounds herein are simultaneously inverse agonists at serotonin $5HT_{2A}$ and $5HT_{2B}$ receptors and agonists at $5HT_{2C}$ receptors. In aspects, the invention provides a method of treating or preventing a disease or disorder (e.g., psychiatric disorder; obesity) in a subject comprising administering to the subject a compound that is simultaneously an inverse agonist at serotonin $5HT_{2A}$ and $5HT_{2B}$ receptors and agonist at $5HT_{2C}$ receptors. In another embodiment, the method is that wherein the subject is in need of treatment for both a psychiatric disorder and obesity.

In one embodiment, the compounds provide methods for pharmacologically treating a disease or disorder arising from disturbances in the acetylcholine muscarinic receptor system in a subject comprising administering to the subject a compound of any of the formulae herein. The compounds of any of the formulae herein have pharmacologically-relevant affinity for muscarinic $M_1$, $M_2$, $M_3$, $M_4$, and/or $M_5$ receptors and behave functionally as agonists, inverse agonists, and/or antagonists at one or more of the muscarinic receptors.

Typical diseases or disorders (Brown and Taylor, 2006, Muscarinic Agonists and Antagonists. In: Brunton L. L., Lazo, J. S., Parker, K. L. (Eds.), Goodman and Gilman's The Pharmacological Basis of Therapeutics $11^{th}$ Edition. McGranw-Hill, New York, N.Y., pp. 183-200) that respond to modulation of the pharmacology of muscarinic $M_1$, $M_2$, $M_3$, $M_4$, and/or $M_5$ receptors include but are not limited to: disorders of the gastrointestinal tract (constipation, diarrhea, excess acid, spasticity), urinary tract (frequency of urination, lack of urination, excess urination), glaucoma, asthma, Parkinson's disease, Alzheimer's disease, various disorders involving exocrine glands (problems with sweating, tear formation, saliva formation, mucous formation), and treatment of poisoning from certain mushrooms (e.g., those containing natural muscarine derivatives).

In another aspect, the invention provides a method for identifying a compound that modulates 5-HT2c, the method comprising obtaining a crystal structure of a 5-HT2c protein or obtaining information relating to the crystal structure of a 5-HT2c protein and modeling a test compound into or on the 5-HT2c protein structure to determine whether the compound modulates the interaction of a 5-HT2c protein. In certain embodiments, the step of modeling comprises modeling or determining the ability of the compound to bind to or associate with a binding pocket defined by structure coordinates of the one or more of transmembrane domains 1-7 of 5-HT2c.

Yet another aspect of the invention is a method for identifying a compound useful to treat or prevent obesity, addiction, cocaine addiction, amphetamine/methamphetamine addiction, psychosis, anxiety. The method includes contacting a 5-HT2c complex with a test compound, and evaluating the ability of the test compound to modulate (e.g., agonize or antagonize), 5-HT2c.

Yet another aspect of the invention is a method for identifying a compound that modulates the activity of 5-HT2c, the method comprising using the atomic coordinates of the one or more of transmembrane domains 1-7 of 5-HT2c, to generate a three-dimensional structure (e.g., in silico) of a molecule comprising a binding pocket, and employing the three-dimensional structure to identify a compound that modulates the activity of the one or more of transmembrane domains 1-7 of 5-HT2c.

In another aspect, the invention provides a packaged composition including a therapeutically effective amount of a 5-HT2c agonist compound and a pharmaceutically acceptable carrier or diluent. The composition may be formulated for treating a subject suffering from or susceptible to a neuropsychiatric disorder (e.g., obesity), and packaged with instructions to treat a subject suffering from or susceptible to a neuropsychiatric disorder.

In one aspect, the invention provides a kit for treating a neuropsychiatric disorder in a subject is provided and includes a compound herein, pharmaceutically acceptable esters, salts, and prodrugs thereof, and instructions for use. In further aspects, the invention provides kits for agonizing 5-HT2c, assessing the efficacy of an anti-obesity treatment in a subject, monitoring the progress of a subject being treated with a 5-HT2c agonist, selecting a subject with a neuropsychiatric disorder for treatment with 5-HT2c agonist, and/or treating a subject suffering from or susceptible to a neuropsychiatric disorder (e.g., obesity). In certain embodiments, the invention provides: a kit for treating a neuropsychiatric disorder in a subject, the kit comprising a compound capable of modulating (e.g., agonizing) 5-HT2c agonist activity. In other aspects the compound selectively agonizes 5-HT2c relative to 5-HT2a and/or 5-HT2b. In other aspects the compound selectively antagonizes 5-HT2a and/or 5-HT2b.

In another aspect, the invention relates to a three-dimensional structure of a one or more of transmembrane domains 1-7 of 5-HT2c, each alone or combinations thereof.

Thus, the present invention provides molecules or molecular complexes that comprise either one or both of these binding pockets or homologues of either binding pocket that have similar three-dimensional shapes.

The invention also provides a pharmaceutical composition of the compounds described herein, comprising a compound capable of agonizing 5-HT2c; a compound capable of agonizing 5-HT2c selectively relative to 5-HT2a and/or 5-HT2b; a compound capable of agonizing 5-HT2c and antagonizing 5-HT2a and/or 5-HT2b; or a pharmaceutically acceptable ester, salt, or prodrug thereof, together with a pharmaceutically acceptable carrier.

In another aspect, the invention provides a machine readable storage medium which comprises the structural coordinates of a binding pocket defining the one or more of transmembrane domains 1-7 of 5-HT2c.

In another aspect, the invention provides a computer for producing a three-dimensional representation of a molecule or molecular complex, wherein said molecule or molecular complex comprises a binding pocket defined by structure coordinates of the one or more of transmembrane domains 1-7 of 5-HT2c; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes: (i) a machine-readable data storage medium comprising a data storage material encoded with machine-readable data, wherein said data comprises the structure coordinates of the one or more of transmembrane domains 1-7 of 5-HT2c; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

In another aspect, the invention provides a packaged composition including a therapeutically effective amount of RSK inhibitor compound (e.g., a selective RSK-1, -3, or -4 inhibitor compound) and a pharmaceutically acceptable carrier or diluent. The composition may be formulated for treating a subject suffering from or susceptible to a disease or disorder (e.g., cancer, HIV, RSK-mediated disease), and packaged with instructions to treat a subject suffering from or susceptible to a disease or disorder.

In one aspect, the invention provides a kit for treating a disease or disorder in a subject and includes a compound herein, pharmaceutically acceptable esters, salts, and prodrugs thereof, and instructions for use. In further aspects, the invention provides kits for inhibiting RSK. In certain embodiments, the invention provides: a kit for treating a disease or disorder (i.e., a RSK-mediated disease or disorder) in a subject, the kit comprising a compound capable of modulating (e.g., inhibiting) RSK activity. In other aspects the compound selectively inhibits RSK relative to other kinases. In other aspects the compound selectively inhibits RSK-1, -3, or -4 relative to other kinases.

The invention also provides a pharmaceutical composition of the compounds described herein, comprising a compound capable of of modulating (e.g., inhibiting) RSK activity or pharmaceutically acceptable ester, salt, or prodrug thereof, together with a pharmaceutically acceptable carrier. In other aspects the compound selectively inhibits RSK relative to other kinases. In other aspects the compound selectively inhibits RSK-1, -3, or -4 relative to other kinases. In other aspects the compound modulates RSK-by modulation (e.g., inverse agonist activity) of 5-HT2 (e.g., one or more of 5-HT2a, b, or c).

The invention also provides methods for designing, evaluating and identifying compounds which bind to the aforementioned binding pockets. Other embodiments of the invention are disclosed infra.

BRIEF DESCRIPTION OF THE DRAWINGS

The present invention is further described below with reference to the following non-limiting examples and with reference to the following figures, in which:

FIGS. 1A-1E illustrate representative binding curves of (−)-trans-CAT and (+)-trans-CAT with wild type $5HT_{2A}$, $5HT_{2B}$, $5HT_{2C}$ and Histamine H1 receptors transiently expressed in HEK 293 cells.

FIG. 5 illustrates kinase targets.

DETAILED DESCRIPTION OF THE INVENTION

Figure 1B:
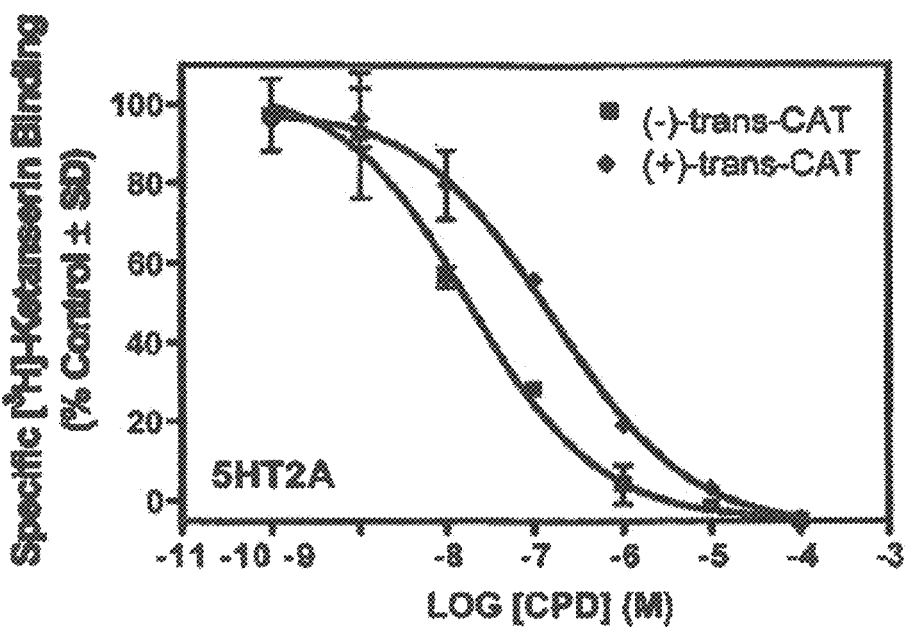
Figure 1C:
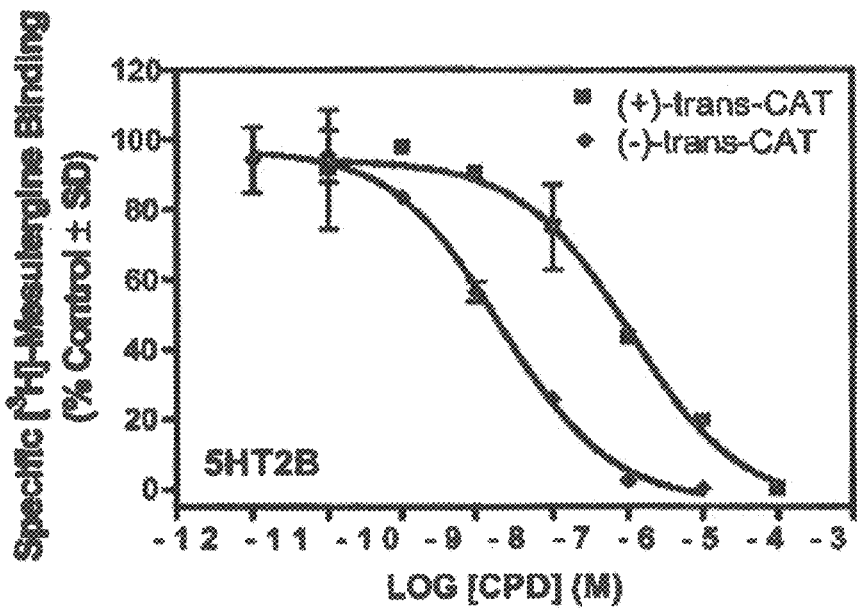
Figure 1D:
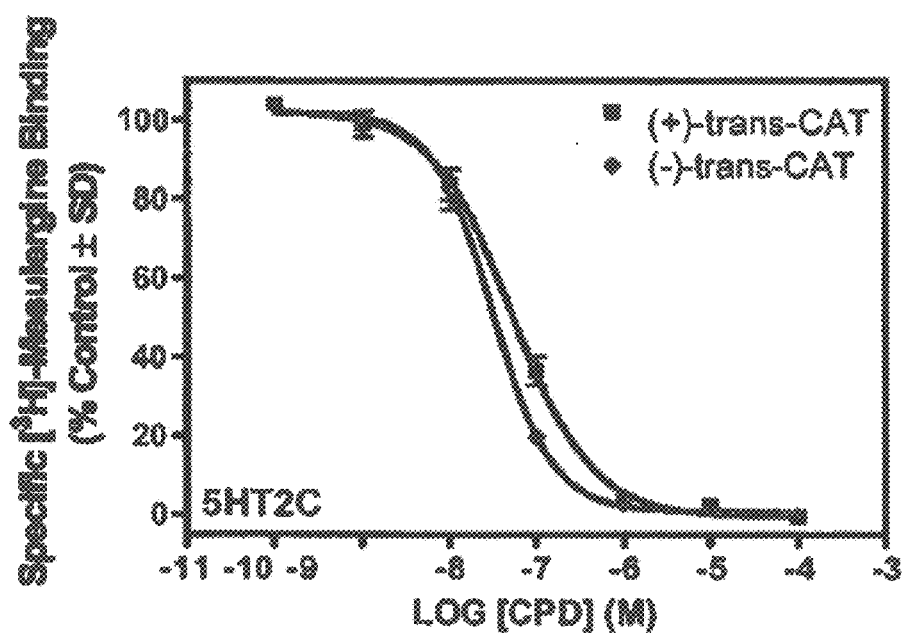
Figure 1E:
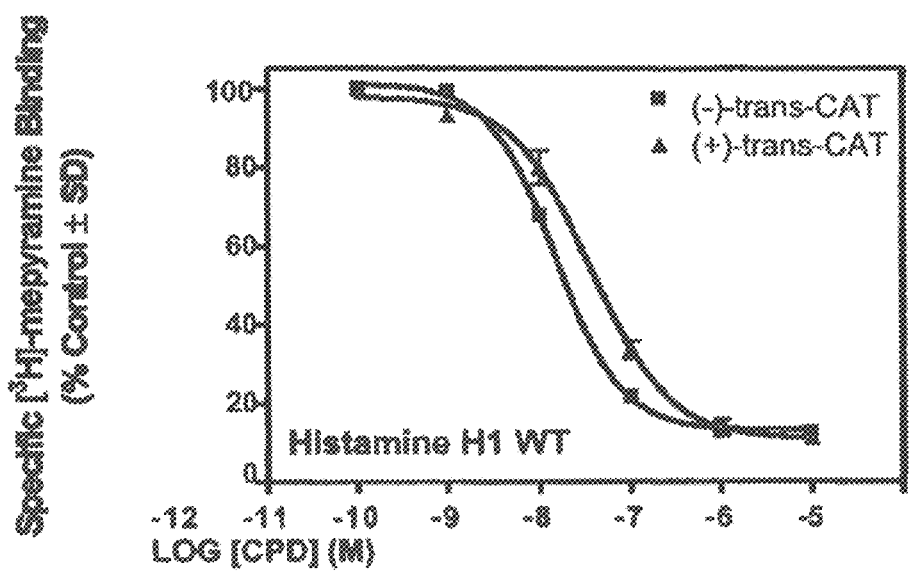

The present inventors have now discovered a therapeutic strategy that addresses selective disease treatment and prevention (i.e., having reduced or minimized adverse side effects) by selectively targeting 5-HT2c and/or RSK. Such interactions are relevant for modulation of 5-HT2c mediated disorders, particularly in certain neuropsychiatric disorder types where 5-HT2 mechanisms play a significant role.

The present invention relates, at least in part, to the discovery that the 5-HT2c interactions are useful as targets (e.g., selective) for neuropsychiatric disorder therapy.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a disorder delineated herein. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The terms "halogen" and "halo" designate —F, —Cl, —Br or —I.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The terms "heterocyclic" or "heterocyclo" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring, which typically contains from 3 to 14 ring atoms, from 3 to 8 ring atoms, from 3 to 6 ring atoms, or from 5 to 6 ring atoms. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "GPCR disorder" includes any disease, disorder or symptoms thereof that are mediated by a G protein-coupled receptor (e.g., 5-HT2a, 5-HT2b, 5-HT 2c, muscarinic M1-M5). Diseases and disorders mediated by such GPCRs include, for example, neuropsychiatric disorders (e.g., obesity, addiction, cocaine addiction, amphetamine/methamphetamine addiction, psychosis anxiety, depression, schizophrenia, psychosis, and sleep disorders), neurodegenerative disorders (e.g., Parkinson's Disease, Alzheimer's Disease), neurological disorders (e.g., epilepsy), cardiovascular disorders (e.g., hypertension), gastrointestinal disorders (e.g., irritable bowel syndrome), and genitor-urinary tract disorders (e.g., bladder control).

The language "M1-M5 GPCR" refers to the cholinergic muscarinic M1-M5 neurotransmitter G protein-coupled receptors (including those delineated herein) that.

The language "5-HT2" refers to the serotonin receptors (including those delineated herein) such as 5-HT2a, 5-HT2b and 5-HT2c sub-types.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —$CONH_2$, mono- or di-($C_1$-$C_8$alkyl)aminocarbonyl, —$SO_2NH_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a compound inhibit activity of a target in response to exposure to a compound of the invention, including for example in an subject (e.g., animal, human) such that a desired end result is achieved, e.g., a therapeutic result.

The term "obtaining" as in "obtaining a compound capable of modulating (agonizing, antagonizing) a target delineated herein and is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and infrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings.

Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a disorder herein.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a disorder herein or who could otherwise benefit from the administration of a compound of the invention of the invention, such as human and non-human animals. Preferred humans include human patients suffering from or prone to suffering from a neuropsychiatric disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a neuropsychiatric disorder" is meant to include subjects at risk of developing a neuropsychiatric disorder, e.g., including those delineated herein, i.e., subjects suffering from a neuropsychiatric disorder or symptom thereof, subjects having a family or medical history of neuropsychiatric disorder or symptom thereof, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, treating or preventing a neuropsychiatric disorder and/or symptoms of a neuropsychiatric disorder, or in prolonging the survivability of the patient with such a neuropsychiatric disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides compounds capable of modulating (e.g., inhibiting or stimulating) (directly or indirectly) 5-HT and/or RSK binding activity.

In one embodiment, the invention provides a compound capable of agonizing 5-HT2c and/or RSK; and pharmaceutically acceptable esters, salts, and prodrugs thereof. In certain embodiments, the compound is a compound of Formula (I). In certain embodiments, the compound is a compound of Formula (II), (II-a), (III), (IV), or (V).

Certain preferred compounds include compounds specifically delineated herein: Table 1: Compounds:

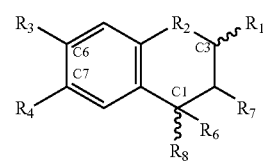

Formula I

Configuration is stereochemistry at C1 & C3

TABLE 1

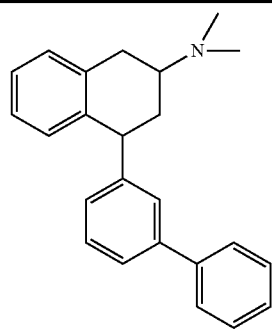

CLogP: 6.005

TABLE 1-continued
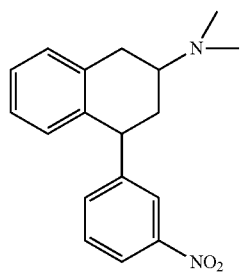 [SMILES: CN(C)C1Cc2ccccc2C(c2cccc([N+](=O)[O-])c2)C1]
CLogP: 3.86
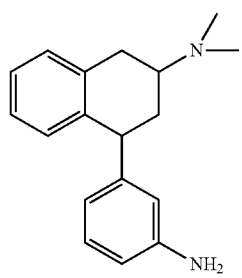 [SMILES: CN(C)C1Cc2ccccc2C(c2cccc(N)c2)C1]
CLogP: 2.89
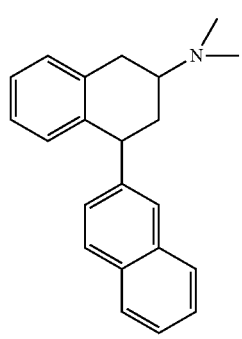 [SMILES: CN(C)C1Cc2ccccc2C(c2ccc3ccccc3c2)C1]
CLogP: 5.291
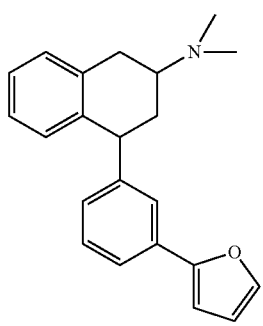 [SMILES: CN(C)C1Cc2ccccc2C(c2cccc(-c3ccco3)c2)C1]
CLogP: 5.391
TABLE 1-continued
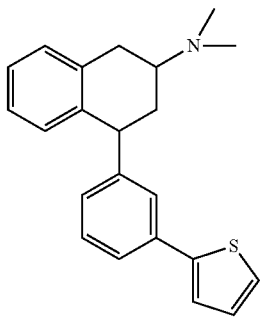 [SMILES: CN(C)C1Cc2ccccc2C(c2cccc(-c3cccs3)c2)C1]
CLogP: 5.861
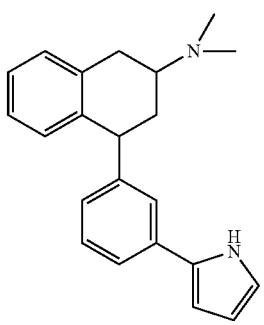 [SMILES: CN(C)C1Cc2ccccc2C(c2cccc(-c3ccc[nH]3)c2)C1]
CLogP: 4.821
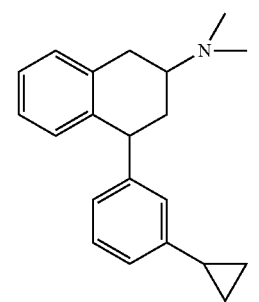 [SMILES: CN(C)C1Cc2ccccc2C(c2cccc(C3CC3)c2)C1]
CLogP: 5.06
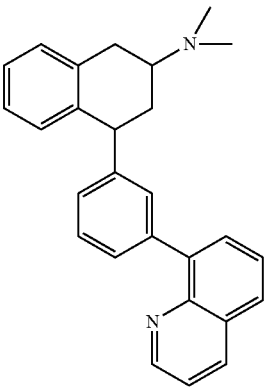 [SMILES: CN(C)C1Cc2ccccc2C(c2cccc(-c3cccc4cccnc34)c2)C1]
CLogP: 5.892

TABLE 1-continued
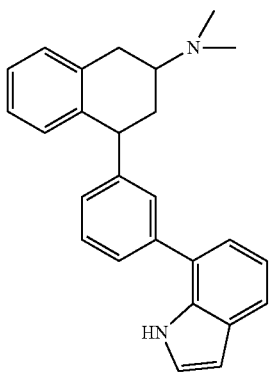 [SMILES: CN(C)C1Cc2ccccc2C(c2cccc(-c3cccc4cc[nH]c34)c2)C1]
CLogP: 5.995
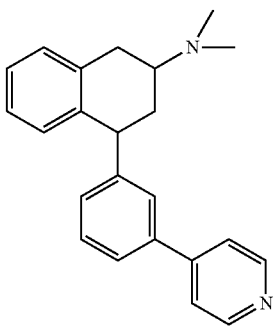 [SMILES: CN(C)C1Cc2ccccc2C(c2cccc(-c3ccncc3)c2)C1]
CLogP: 4.508
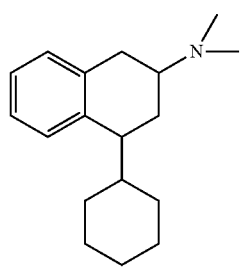 [SMILES: CN(C)C1Cc2ccccc2C(C2CCCCC2)C1]
CLogP: 5.1
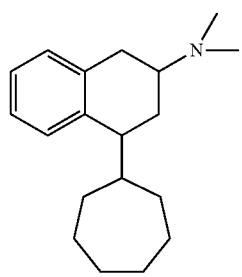 [SMILES: CN(C)C1Cc2ccccc2C(C2CCCCCC2)C1]
CLogP: 6.3
TABLE 1-continued
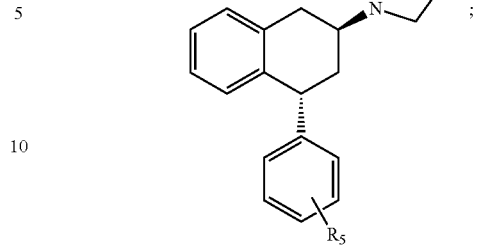
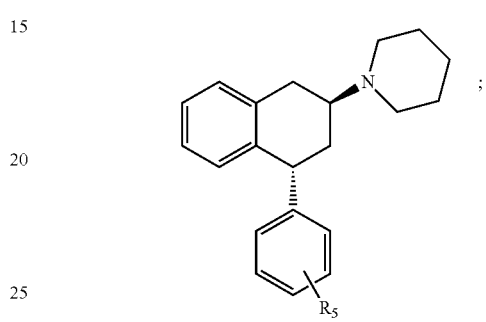
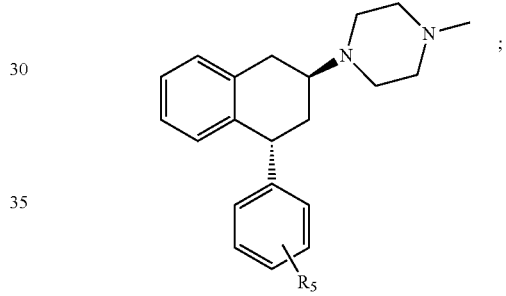
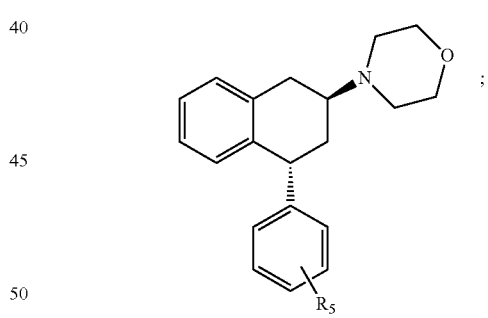
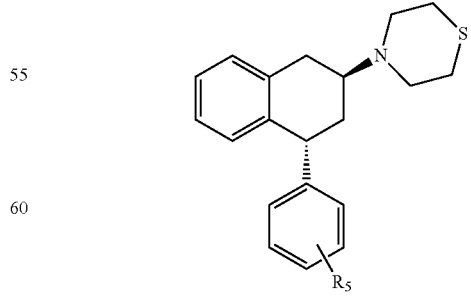
wherein each R5 is independently para or meta H, F, Cl, or Br TABLE 1-continued
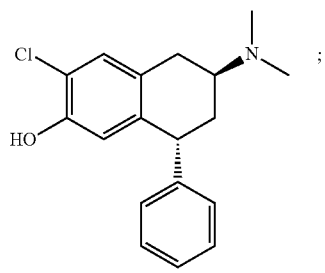 [SMILES: CN(C)[C@@H]1Cc2cc(Cl)c(O)cc2[C@@H](c2ccccc2)C1]
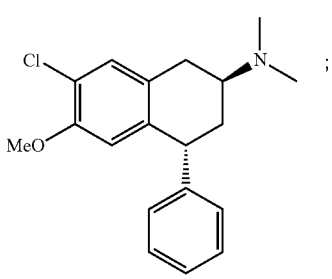 [SMILES: COc1cc2c(cc1Cl)C[C@@H](N(C)C)C[C@@H]2c1ccccc1]
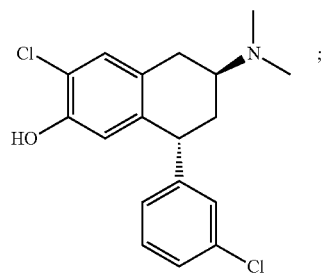 [SMILES: CN(C)[C@@H]1Cc2cc(Cl)c(O)cc2[C@@H](c2cccc(Cl)c2)C1]
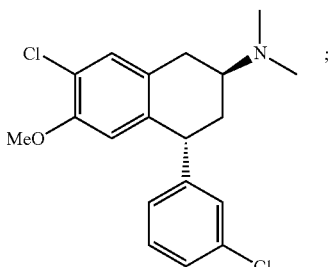
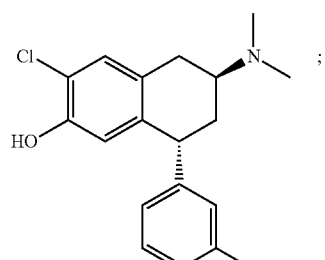
TABLE 1-continued
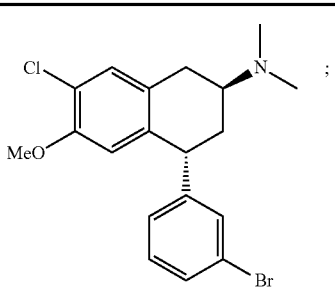
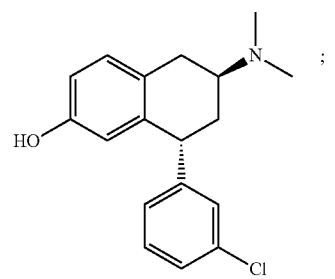 [SMILES: CN(C)[C@@H]1Cc2ccc(O)cc2[C@@H](c2cccc(Cl)c2)C1]
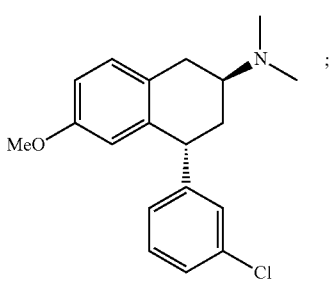 [SMILES: COc1ccc2c(c1)[C@@H](c1cccc(Cl)c1)C[C@H](N(C)C)C2]
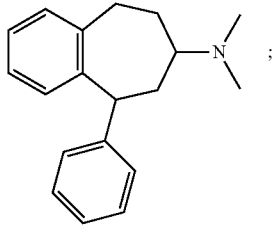 [SMILES: CN(C)C1CCc2ccccc2C(c2ccccc2)C1]
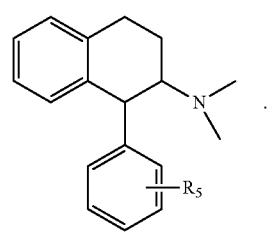

Certain preferred compounds include compounds specifically delineated herein: Table 2: Compounds:

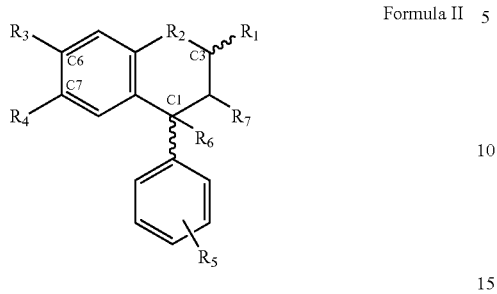

Formula II

Configuration is stereochemistry at C1 & C3

TABLE 3

| PAT# | Config | $R_1$ | $R_2$ | $R_3$ | $R_4$ | $R_5$ | $R_6$ | $R_7$ |
|---|---|---|---|---|---|---|---|---|
| 1 | (1R,3S)-(−)-trans | $N(CH_3)_2$ | $CH_2$ | H | H | H | H | H |
| 2 | (1S,3R)-(+)-trans | $N(CH_3)_2$ | $CH_2$ | H | H | H | H | H |
| 3 | (1R,3R)-(−)-cis | $N(CH_3)_2$ | $CH_2$ | H | H | H | H | H |
| 4 | (1S,3S)-(+)-cis | $N(CH_3)_2$ | $CH_2$ | H | H | H | H | H |
| 5 | (±)-trans(PAB) | $N(CH_3)_2$ | $(CH_2)_2$ | H | H | H | H | H |
| 6 | (±)-cis(PAB) | $N(CH_3)_2$ | $(CH_2)_2$ | H | H | H | H | H |
| 7 | (±)-trans | $N(CH_3)_2$ | $CH_2$ | Cl | OH | H | H | H |
| 8 | (±)-cis | $N(CH_3)_2$ | $CH_2$ | Cl | OH | H | H | H |
| 9 | (±)-trans | $N(CH_3)_2$ | $CH_2$ | OH | OH | H | H | H |
| 10 | (±)-cis | $N(CH_3)_2$ | $CH_2$ | OH | OH | H | H | H |
| 11 | (±)-trans | $N(CH_3)_2$ | $CH_2$ | H | H | H | $CH_3$ | H |
| 12 | (±)-cis | $N(CH_3)_2$ | $CH_2$ | H | H | H | $CH_3$ | H |
| 13 | (±)-trans | $N(CH_3)_2$ | $CH_2$ | H | H | p—Cl | H | H |
| 14 | (±)-trans | $N(CH_3)_2$ | $CH_2$ | H | H | p—F | H | H |
| 15 | (±)-trans | $N(CH_3)_2$ | $CH_2$ | H | H | $pCH_3$ | H | H |
| 16 | (±)-trans | $N(CH_3)_2$ | $CH_2$ | H | H | o—Cl | H | H |
| 17 | (±)-trans | $N(CH_3)_2$ | $CH_2$ | H | H | $oCH_3$ | H | H |
| 18 | (±)-trans | $N(CH_3)_3$ | $CH_2$ | H | H | H | H | H |
| 19 | (±)-cis | $N(CH_3)_3$ | $CH_2$ | H | H | H | H | H |
| 20 | (±)-trans | $NH(CH_3)$ | $CH_2$ | H | H | H | H | H |
| 21 | (±)-cis | $NH(CH_3)$ | $CH_2$ | H | H | H | H | H |
| 22 | (±)-trans | $NH_2$ | $CH_2$ | H | H | H | H | H |
| 23 | (±)-cis | $NH_2$ | $CH_2$ | H | H | H | H | H |
| 24 | (±)-trans | $NH_2$ | $CH_2$ | OH | OH | H | H | H |
| 25 | (±)-cis | $NH_2$ | $CH_2$ | OH | OH | H | H | H |
| 26 | (±)-trans | H | $CH_2$ | H | H | H | H | $N(CH_3)$ |
| 27 | (±)cis | H | $CH_2$ | H | H | H | H | $N(CH_3)$ |
| 28 | (±)-trans | $N(C_2H_5)_2$ | $CH_2$ | H | H | H | H | H |
| 29 | (±)-trans | $N(C_3H_5)_2$ | $CH_2$ | H | H | H | H | H |
| 30 | (±)-trans | $NCH_3(C_3H_5)$ | $CH_2$ | H | H | H | H | H |
| 31 | (±)-trans | $NH(C_3H_5)$ | $CH_2$ | H | H | H | H | H |
| 32 | (1R,3S)-(−)-trans | $N(CH_3)_2$ | $CH_2$ | H | H | m—F | H | H |
| 33 | (1S,3R)-(+)-trans | $N(CH_3)_2$ | $CH_2$ | H | H | m—F | H | H |
| 34 | (1R,3S)-(−)-trans | $N(CH_3)_2$ | $CH_2$ | H | H | m—Cl | H | H |
| 35 | (1S,3R)-(+)-trans | $N(CH_3)_2$ | $CH_2$ | H | H | m—Cl | H | H |
| 36 | (1R,3S)-(−)-trans | $N(CH_3)_2$ | $CH_2$ | H | H | m—Br | H | H |
| 37 | (1S,3R)-(+)-trans | $N(CH_3)_2$ | $CH_2$ | H | H | m—Br | H | H |
| 38 | (1R,3S)-(−)-trans | $N(CH_3)_2$ | $CH_2$ | H | H | p—Br | H | H |
| 39 | (1S,3R)-(+)-trans | $N(CH_3)_2$ | $CH_2$ | H | H | p—Br | H | H |
| 40 | (+/−)-trans | $NCH_3((CH_2)_2Ph)$ | $CH_2$ | H | H | H | H | H |
| 41 | (+/−)-trans | $NCH_3((CH_2)_4Ph)$ | $CH_2$ | H | H | H | H | H |
| 42 | (+/−)-trans | $NH((CH_2)_3Ph)$ | $CH_2$ | H | H | H | H | H |
| 43 | (+/−)-trans | $NH((CH_2)_4Ph)$ | $CH_2$ | H | H | H | H | H |

Figure 4:
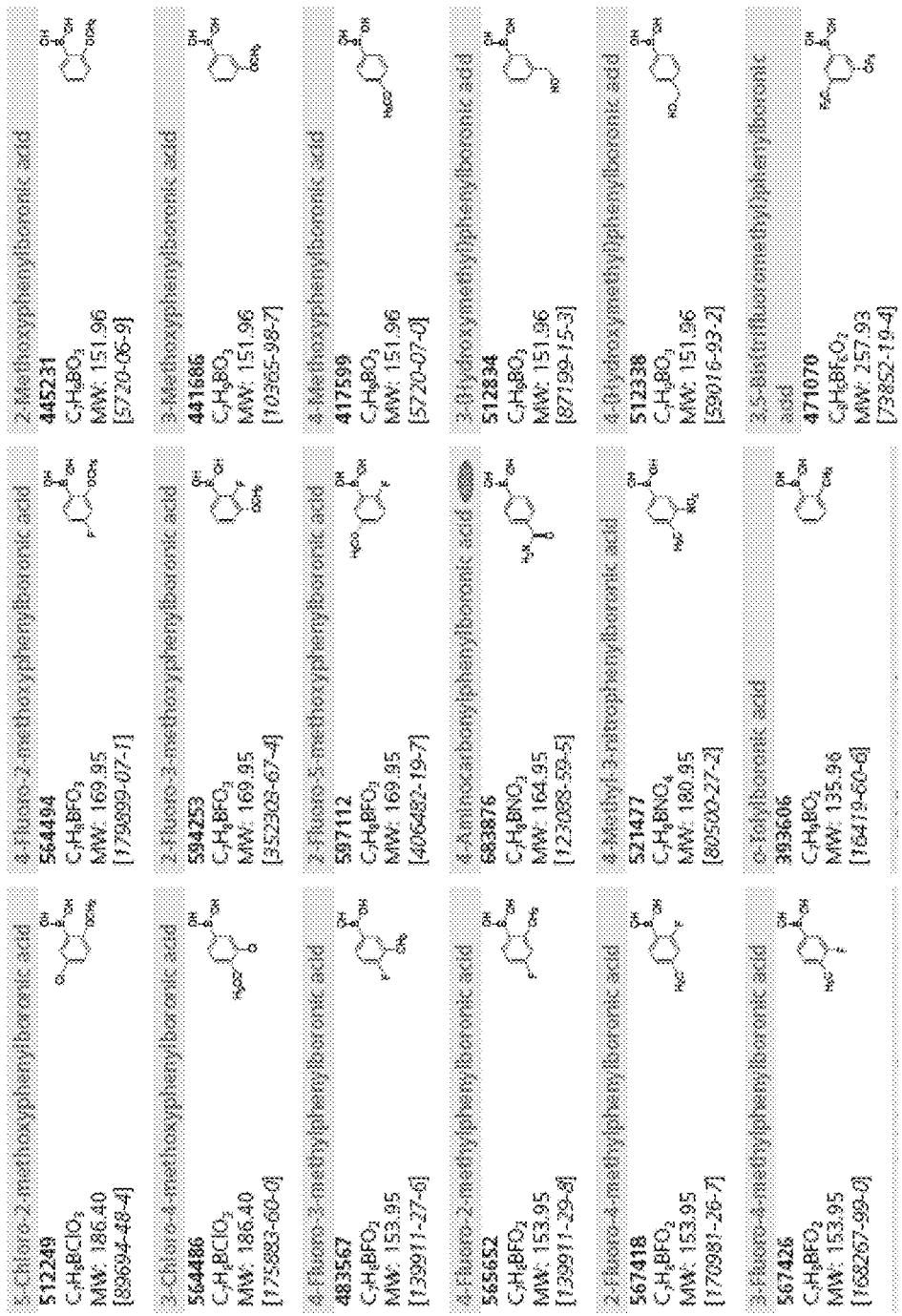
FIG. 4 illustrates Suzuki Coupling Reagents.
Figure 4:
Figure 4:
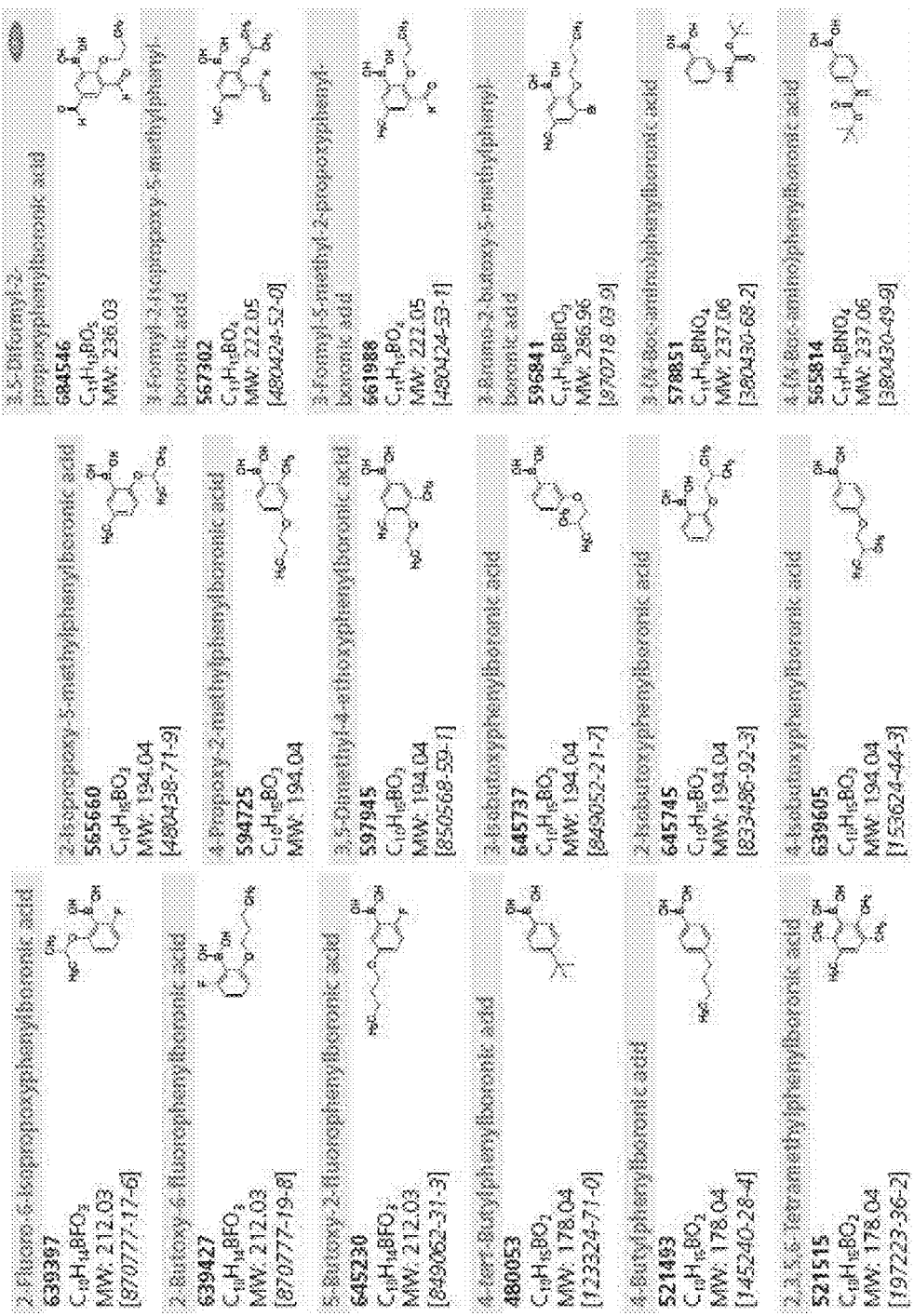
Figure 4:
Figure 4:
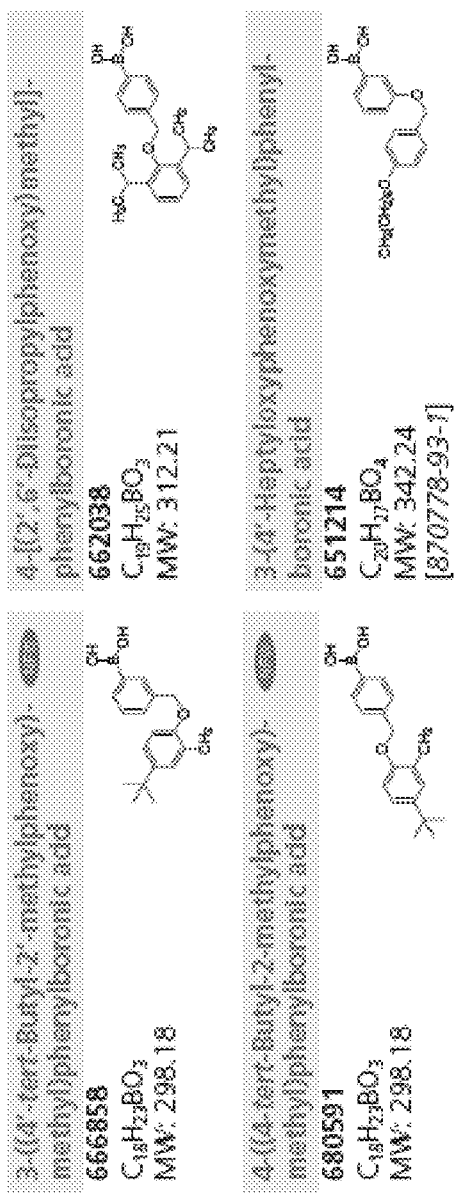
Figure 4:
Figure 4:

The compounds of the formulae herein include those wherein $R_6$ or $R_8$ are a substitutent (e.g., alkyl, aryl, cycloalkyl) that is a moiety attached to the boron atom in a boronic acid compound delineated in FIG. 4.

Chart of New C(1) Substituted PAT Analogs

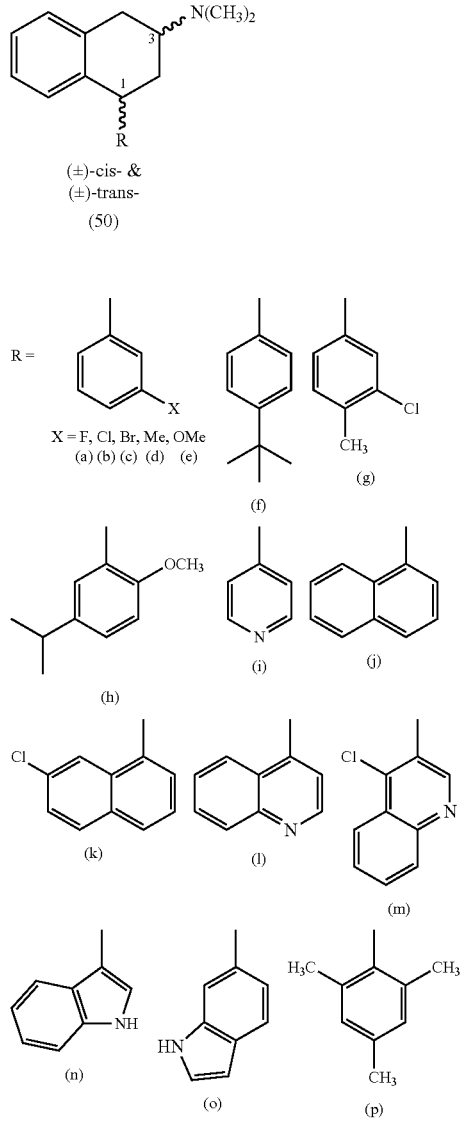

Additional compounds of the invention include the following compounds of formula (V):

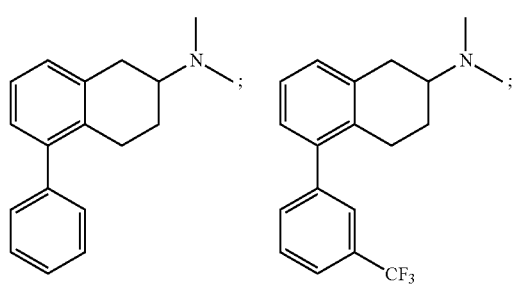

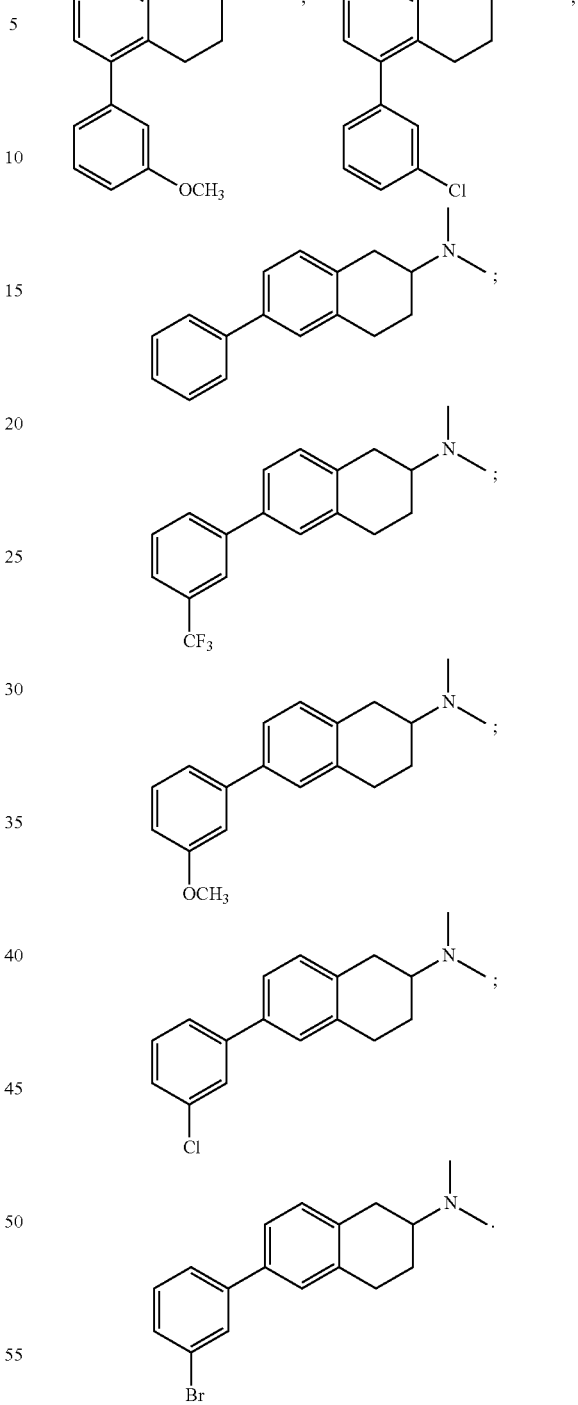

All enantiomers, diastereomers, racemates, racemic mixtures, enantioenriched mixtures, and diasteromeric mixtures of any of the compounds delineated above are contemplated by the invention.

From mutagenesis and modeling data, the PAT protonated (pH 7.4) amine forms an ionic bond with conserved 5HT2 residue D3.32 (Booth et al., 2009). Modeling results in Aim 3 also indicate the PAT amine orients close (~2 Å) to S3.36 & Y7.43, thus, amine substituents (R1, Chart 1) with additional heteroatoms are proposed to form hydrogen bonds with these residues. Also, Aim 3 modeling results show the PAT N-alkyl moiety binds in a sterically-generous receptor space, thus, sterically large R1 heterocyclic substituents proposed may form van der Waals interactions with nearby 5HT2 residues. Para-substituted PAT analogs potently modulate amphetamine behaviors (Aim 4), thus, para-halogenated PATs are synthesized first, followed by meta-halogenated, pending in vivo results for previously synthesized meta-substituted PATs.

Meta-halogenated PATs demonstrated highest 5HT2 affinity and potent functional selectivity. Molecular modeling indicates the 5HT2 family binding pocket is sterically generous regarding interactions with substituents at the meta-position of the PAT pendant phenyl ring (Booth et al., 2009; Aim 3 results). Thus, various analogs were designed to facilitate additional hydrogen bonding and aromatic interactions with conserved 5HT2 residues W6.48 F6.51 F6.52 and Y7.43 that are hypothesized and known (mutagenesis data) to interact with the PAT (C4) pendant phenyl moiety.

Based on modeling studies (Booth, 2009; Aim 3), additional analogs were designed to form additional hydrogen bonds with conserved 5HT2 residues V3.33, 53.36, 55.43 & F6.52, hypothesized and known (mutagenesis data) to interact with the aromatic part of PAT tetrahydronaphthyl ring.

The invention also relates to the pharmaceutically acceptable salts and esters of the above-mentioned compounds.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to GPCR or binding pocket thereof produced or identified by the methods described herein.

3. Uses of the Compounds of the Invention

In one embodiment, the invention provides methods for treating a subject for a GPCR-mediated disorder disorder, by administering to the subject an effective amount of a compound capable of modulating (agonizing, antagonizing) a GPCR target. A GPCR disorder includes diseases and disorders mediated by such GPCRs. The herein delineated compounds, compositions and methods are useful for treating or preventing disorder including, for example, neuropsychiatric disorders (e.g., obesity, addiction, cocaine addiction, amphetamine/methamphetamine addiction, anxiety, depression, schizophrenia, and sleep disorders), neurodegenerative disorders (e.g., Parkinson's Disease, Alzheimer's Disease), neurological disorders (e.g., epilepsy), cardiovascular disorders (e.g., 5-HT2b mediated disease, hypertension), gastrointestinal disorders (e.g., irritable bowel syndrome), and genitor-urinary tract disorders (e.g., bladder control). In certain embodiments, the subject is a mammal, e.g., a primate, e.g., a human.

In one embodiment, the invention provides compounds and methods for treating a subject for a histamine (e.g., H1, H2, H3, H4)-mediated disorder, by administering to the subject an effective amount of a compound capable of modulating (agonizing, antagonizing) a histamine target. A histamine disorder includes diseases and disorders mediated by such histamine (e.g., H1). The herein delineated compounds, compositions and methods are useful for treating or preventing disorder including, for example, respiratory distress (e.g., bronchial constriction), diarrhea (GI contractions), edema, and hypotension (e.g., increased vascular permeability), allergic response, and neuropsychiatric, neurodegenerative and neurological disorders herein.

In this embodiment, the compounds of the invention may either directly or indirectly modulate (e.g., agonize, stimulate) the activity of 5-HT2c or specific domains thereof. A cell can be contacted with a compound of the invention to agonize 5-HT2c and modulate 5-HT2c mediated activity. Contacting cells or administering the compounds of the invention to a subject is one method of treating a cell or a subject suffering from or susceptible to unwanted or undesired 5-HT2C mediated activity or a 5-HT2c mediated disorder.

In one embodiment, a method of treating a subject suffering from or susceptible to a 5-HT2c disorder includes administering to a subject in need thereof a therapeutically effective amount of a compound capable of directly or indirectly modulating the activity of 5-HT2c, to thereby treat the subject. Exemplary compounds include those compounds or formulae (formula I, II, II-a, III, IV or V) described herein).

Thus, in one embodiment, the invention provides methods for treating a subject for a 5-HT2C disorder, by administering to the subject an effective amount of a compound capable of agonizing 5-HT2c.

In another aspect, the invention provides a method of treating or preventing obesity in a subject comprising administering to the subject identified as in need thereof a combination of a compound of any of the formulae herein and an amphetamine compound. The compounds may be administered concurrently, simultaneously, or sequentially. In aspects, the amphetamine compound is phentermine.

In certain embodiments, the methods of the invention include administering to a subject a therapeutically effective amount of a compound of the invention in combination with another pharmaceutically active compound. Other pharmaceutically active compounds that may be used can be found in *Harrison's Principles of internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In one aspect, the invention provides a method of treating a subject suffering from or susceptible to obesity comprising administering to subject in need thereof a therapeutically effective amount of a compound capable of activating 5-HT2C receptors (e.g., a compound herein) in combination with an amphetamine compound. In one embodiment, the compound is capable of activating 5-HT2$_C$ receptors. In another embodiment, the compound is capable of activating 5-HT2$_C$, while antagonizing 5-HT2$_A$ and/or 5-HT2$_B$ receptors. In another embodiment, the compound is capable of activating 5-HT2$_C$, and/or antagonizing 5-HT2$_A$ and/or 5-HT2$_B$ receptors. In another embodiment, the compound is capable of antagonizing 5-HT2$_A$ and/or 5-HT2$_B$ receptors.

In another aspect, the invention provides a method of treating a subject suffering from or susceptible to obesity comprising administering to a subject in need thereof a therapeutically effective amount of a 5-HT2c activating compound in combination with an amphetamine compound.

In another aspect, the invention provides a method of treating a subject suffering from or susceptible to obesity comprising administering to a subject in need thereof a therapeutically effective amount of a compound capable of modulating 5-HT2 binding interactions by directly modulating 5-HT2c, preferably selectively relative to 5-HT2a and/or 5-HT2b, in combination with an amphetamine compound.

In another aspect, the invention provides a method of treating a subject suffering from or susceptible to obesity comprising administering to a subject identified as in need thereof (i.e., an obese subject) a therapeutically effective amount of a 5-HT2c agonizing compound or a 5-HT2c selective compound, in combination with an amphetamine compound.

In another aspect, the invention provides a method of treating a subject suffering from or susceptible to obesity comprising administering to a subject an agonizing 5-HT2c compound in combination with an amphetamine compound such that the obesity is prevented, ameliorated or treated (e.g., weight loss is observed, weight gain is prevented).

In another aspect, the invention provides a method of treating a subject suffering from or susceptible to obesity comprising administering to the subject an effective amount of a compound capable of activating 5-HT2c, selectively (alone or in combination with an amphetamine), relative to 5-HT2a and/or 5-HT2b activation, in combination with an amphetamine compound such that the subject is treated.

In another aspect, the invention provides a method of treating a subject suffering from or susceptible to obesity comprising administering to the subject an effective amount of a compound capable of agonizing 5-HT2c (including selectively relative to 5-HT2a and/or 5-HT2b) while not (or to a lesser extent) agonizing (and/or antagonizing) 5-HT2a or 5-HT2b receptors, in combination with an amphetamine compound such that the subject is treated.

In another aspect, the invention provides a method of treating a subject suffering from or susceptible to a disease, disorder or symptom thereof comprising administering to the subject an effective amount of a compound identified as a 5-HT2c agonist (e.g., a compound of the formulae herein). In another aspect, the compound is identified as a 5-HT2c agonist and a 5-HT2a inverse agonist (e.g., a compound of the formulae herein). In another aspect, the compound is identified as a 5-HT2c inverse agonist and a 5-HT2a inverse agonist (e.g., a compound of the formulae herein). In another aspect, the compound is identified as a selective 5-HT2c agonist while not (or to a lesser extent) agonizing 5-HT2a or 5-HT2b (e.g., a compound of the formulae herein).

In another aspect, the treatment method comprises that wherein the subject (e.g., patient) is identified as in need of such treatment. In another aspect, the treatment method comprises that wherein the subject (e.g., patient) is administered a compound or composition herein such that the subject is treated for a disease, disorder or symptom delineated herein.

In another aspect, the invention provides a packaged composition including a therapeutically effective amount of a compound of any of the formulae herein combination with an amphetamine compound and a pharmaceutically acceptable carrier or diluent. The composition may be formulated for treating a subject suffering from or susceptible to obesity, and packaged with instructions to treat a subject suffering from or susceptible to obesity.

In certain embodiments, the compound of the invention can be used in combination therapy with conventional anti-obesity, (e.g., fat absorption blockers). Certain 5-HT drugs (e.g., 5-HTa or 5-HTb antagonists) have an undesirable side effect profile that tend to make them less then optimal or unsuitable for certain patients, that is, they demonstrate cardiovascular (e.g., valvular heart disease, pulmonary hypertension, cardiotoxicity) or psychiatric undesirable and or life threatening side effect profiles.

In one embodiment, the compounds of the invention may either directly or indirectly modulate (e.g., inhibit) the activity of RSK or specific domains thereof. A cell can be contacted with a compound of the invention to inhibit RSK and modulate RSK-mediated activity. Contacting cells or administering the compounds of the invention to a subject is one method of treating a cell or a subject suffering from or susceptible to unwanted or undesired RSK-mediated activity or a RSK-mediated disorder.

In one embodiment, a method of treating a subject suffering from or susceptible to RSK-mediated disorder includes administering to a subject in need thereof a therapeutically effective amount of a compound capable of directly or indirectly modulating the activity of RSK, to thereby treat the subject. Exemplary compounds include those compounds or formulae (formula I, II, II-a, III, IV, or V) described herein.

Thus, in one embodiment, the invention provides methods for treating a subject for a RSK-mediated disorder, by administering to the subject an effective amount of a compound capable of inhibiting RSK-1, -3, or -4.

In another aspect, the invention provides a method of treating or preventing cancer (e.g., breast and prostate), HIV, or Coffin-Lowry syndrome in a subject comprising administering to the subject identified as in need thereof a combination of a compound of any of the formulae herein and an additional therapeutic compound (e.g., anticancer agent, anti-HIV agent, Coffin-Lowry syndrome agent). The compounds may be administered concurrently, simultaneously, or sequentially.

In certain embodiments, the methods of the invention include administering to a subject a therapeutically effective amount of a compound of the invention in combination with another pharmaceutically active compound. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In another aspect, the treatment method comprises that wherein the subject (e.g., patient) is identified as in need of such treatment. In another aspect, the treatment method comprises that wherein the subject (e.g., patient) is administered a compound or composition herein such that the subject is treated for a disease, disorder or symptom delineated herein.

Another object of the present invention is the use of a compound as described herein (e.g., of any formulae herein) in the manufacture of a medicament for use in the treatment of a RSK-mediated disorder. Another object of the present invention is the use of a compound as described herein (e.g., of any formulae herein) for use in the treatment of a RSK-mediated disorder.

Determination of a therapeutically effective amount or a prophylactically effective amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific 5-HT2c and/or RSK disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

Compounds determined to be effective for the prevention or treatment of 5-HT2c and/or RSK disorders in animals, e.g., dogs, chickens, and rodents, may also be useful in treatment of 5-HT2c and/or RSK disorders in humans. Those skilled in the art of treating 5-HT2c and/or RSK disease in humans will know, based upon the data obtained in animal studies, the dosage and route of administration of the compound to humans. In general, the dosage and route of administration in humans is expected to be similar to that in animals.

The identification of those patients who are in need of prophylactic treatment for 5-HT2C and/or RSK disorders is well within the ability and knowledge of one skilled in the art. Certain of the methods for identification of patients which are at risk of developing 5-HT2C and/or RSK disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a 5-HT2C and/or RSK disorder by methods well known in the art (e.g., determining level of markers for the 5-HT2C and/or RSK disorder) and then administering a therapeutically effective amount of a compound delineated herein according to the invention to the subject. After an appropriate period of time after the administration of the compound (e.g., 1 day, 1 week, 2 weeks, one month, six months), the extent of the 5-HT2C and/or RSK disorder is determined again. The modulation (e.g., decrease) of the extent or invasiveness of the 5-HT2C and/or RSK disorder indicates efficacy of the treatment. The extent or invasiveness of the 5-HT2C and/or RSK disorder may be determined periodically throughout treatment. For example, the extent or invasiveness of the 5-HT2C and/or RSK disorder may be checked every few hours, days or weeks to assess the further efficacy of the treatment. A decrease in extent or invasiveness of the 5-HT2C and/or RSK disorder indicates that the treatment is efficacious. The method described may be used to screen or select patients that may benefit from treatment with a modulating compound of a 5-HT2C and/or RSK disorder.

A method of assessing the efficacy of a treatment in a subject includes determining the pre-treatment extent of obesity (overweight) by methods well known in the art and then administering a therapeutically effective amount of a compound delineated herein alone or each in combination with an amphetamine compound according to the invention to the subject. After an appropriate period of time after the administration of the compound (e.g., 1 day, 1 week, 2 weeks, one month, six months), the extent of obesity (overweightness) is determined again. The modulation (e.g., decrease) of the extent of overweightness indicates efficacy of the treatment. The extent or invasiveness of obesity may be determined periodically throughout treatment. For example, the extent or invasiveness of overweightness may be checked every few hours, days or weeks to assess the further efficacy of the treatment. A decrease in extent or invasiveness of the overweightness indicates that the treatment is efficacious. The method described may be used to screen or select patients that may benefit from treatment with a modulating compound capable of activating selectively 5-HT2c (vs. 5-HT2a,b) receptors in combination with an amphetamine compound.

As used herein, "obtaining a biological sample from a subject," includes obtaining a sample for use in the methods described herein. A biological sample is described above.

Yet another aspect presents a method to identify a compound that modulates the interaction of 5-HT2C and/or RSK or specific domains thereof. The method may include obtaining the crystal structure of 5-HT2C and/or RSK or specific domains thereof (optionally apo form or complexed) or obtaining the information relating to the crystal structure of 5-HT2C and/or RSK or specific domains thereof (optionally apo form or complexed), in the presence and/or absence of the test compound. Compounds may then be computer modeled into or on the 5-HT2C and/or RSK structure, or specific domains thereof (e.g., a binding site of the crystal structure) to predict stabilization of the interaction between the 5-HT2C and/or RSK or specific domains thereof and the test compound. Once potential modulating compounds are identified, the compounds may be screened using cellular assays, such as the ones identified herein and competition assays known in the art. Compounds identified in this manner are useful as therapeutic agents.

In another aspect, a compound of the invention is packaged in a therapeutically effective amount with a pharmaceutically acceptable carrier or diluent. The composition may be formulated for treating a subject suffering from or susceptible to a 5-HT2C and/or RSK disorder, and packaged with instructions to treat a subject suffering from or susceptible to a 5-HT2C and/or RSK disorder.

In another aspect, the invention provides methods for modulating 5-HT2C and/or RSK disease. In one embodiment, a method of modulating 5-HT2C (or a 5-HT2C disorder) according to the invention includes contacting cells with a compound capable of modulating 5-HT2C (or a 5-HT2C disorder), or specific domains thereof. In one embodiment, a method of modulating RSK (or a RSK disorder) according to the invention includes contacting cells with a compound capable of modulating RSK (or a RSK disorder), or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a 5-HT2C and/or RSK disorder in a subject include administering an effective amount of a compound of the invention (i.e., a compound described herein) to the subject. The administration may be by any route of administering known in the pharmaceutical arts. The subject may have a 5-HT2C and/or RSK disorder, may be at risk of developing a 5-HT2C and/or RSK disorder, or may need prophylactic treatment prior to anticipated or unanticipated exposure to a conditions capable of increasing susceptibility to a 5-HT2C and/or RSK disorder.

In one aspect, a method of monitoring the progress of a subject being treated with a compound herein includes determining the pre-treatment status (e.g., progression, target profile, Marker profile) of the 5-HT2C and/or RSK disorder, administering a therapeutically effective amount of a compound herein to the subject, and determining the status (e.g., progression, target profile, Marker profile) of the 5-HT2C and/or RSK disorder after an initial period of treatment with the compound, wherein the modulation of the status indicates efficacy of the treatment.

The subject may be at risk of a 5-HT2C and/or RSK disorder, may be exhibiting symptoms of a 5-HT2C and/or RSK disorder, may be susceptible to a 5-HT2C and/or RSK disorder and/or may have been diagnosed with a 5-HT2C and/or RSK disorder.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting a 5-HT2C and/or RSK or specific domains thereof with a test compound (complex), and evaluating the binding interaction following contact, wherein a change in the stability of the complex relative to a reference value is an indication that the test compound modulates the stability of the complex.

The 5-HT2C and/or RSK or specific domains thereof complex may be modeled in silico, or may be a complex within a cell, isolated from a cell, recombinantly expressed, purified or isolated from a cell or recombinant expression system or partially purified or isolated from a cell or recombinant expression system.

Kits of the invention include kits for treating a 5-HT2C and/or RSK disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a 5-HT2C and/or RSK disorder may be packaged with a kit for monitoring the progress of a subject being treated for a 5-HT2C and/or RSK disorder according to the invention.

The present methods can be performed on cells in culture, e.g. in vitro or ex vivo, or on cells present in an animal subject, e.g., in vivo. Compounds of the inventions can be initially tested in vitro using primary cultures of cells, e.g., transformed cells, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179, 109-fetal rat tissue culture), or other mammalian (See e.g. U.S. Pat. No. 5,089,517-fetal mouse tissue culture) or non-mammalian animal models.

Alternatively, the effects of compound of the invention can be characterized in vivo using animals models.

4. Pharmaceutical Compositions

The invention also provides a pharmaceutical composition, comprising an effective amount of a compound of the and a pharmaceutically acceptable carrier. In a further embodiment, the effective amount is effective to treat a 5-HT2C and/or RSK disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres.

They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

Synthetic Schemes

The compounds of the invention can be made according to the following synthetic schemes.

Scheme A. Route to N-substituted PAT Analogs

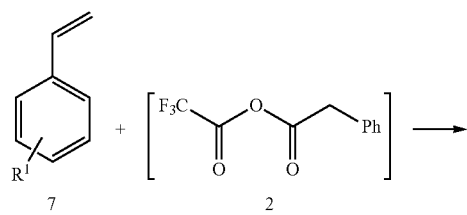

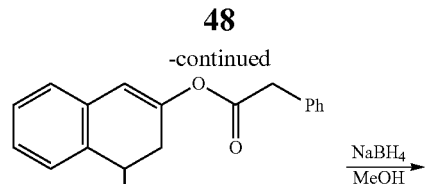

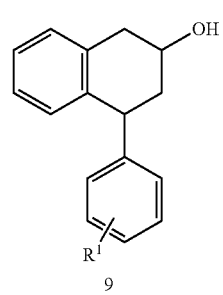

$R^1$ = H, F, Cl, Br (meta or para, as in Appendix 1)
$R^2$ = pyrrolidine, piperidine, N-methyl piperazine
morpholine, thiomorpholine
log P=3.75-5.71, depending on substitutions

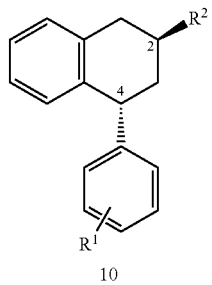

Scheme A: Synthesis of N-substituted PATs in Chart 1.

Reaction of styrene or halostyrene 7 with [2] provides the 4-substituted-tetralen-2-ol phenyl acetate 8. Reduction of 8 gives tetral-2-ol 9. Trans-(2S,4R)—N-substituted PATs 10 are prepared by tosylation of 9, followed by $S_N2$ inversion with cyclic amines (pyrrolidine, piperidine, etc) and enantiomer separation by chiral stationary phase (CSP)-HPLC (Vincek & Booth 2009).

Scheme B. Alternative Route

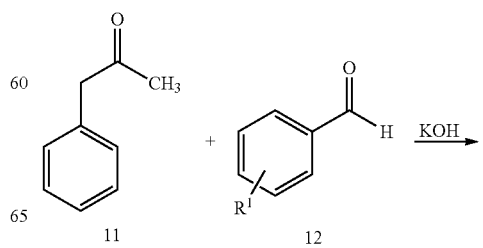

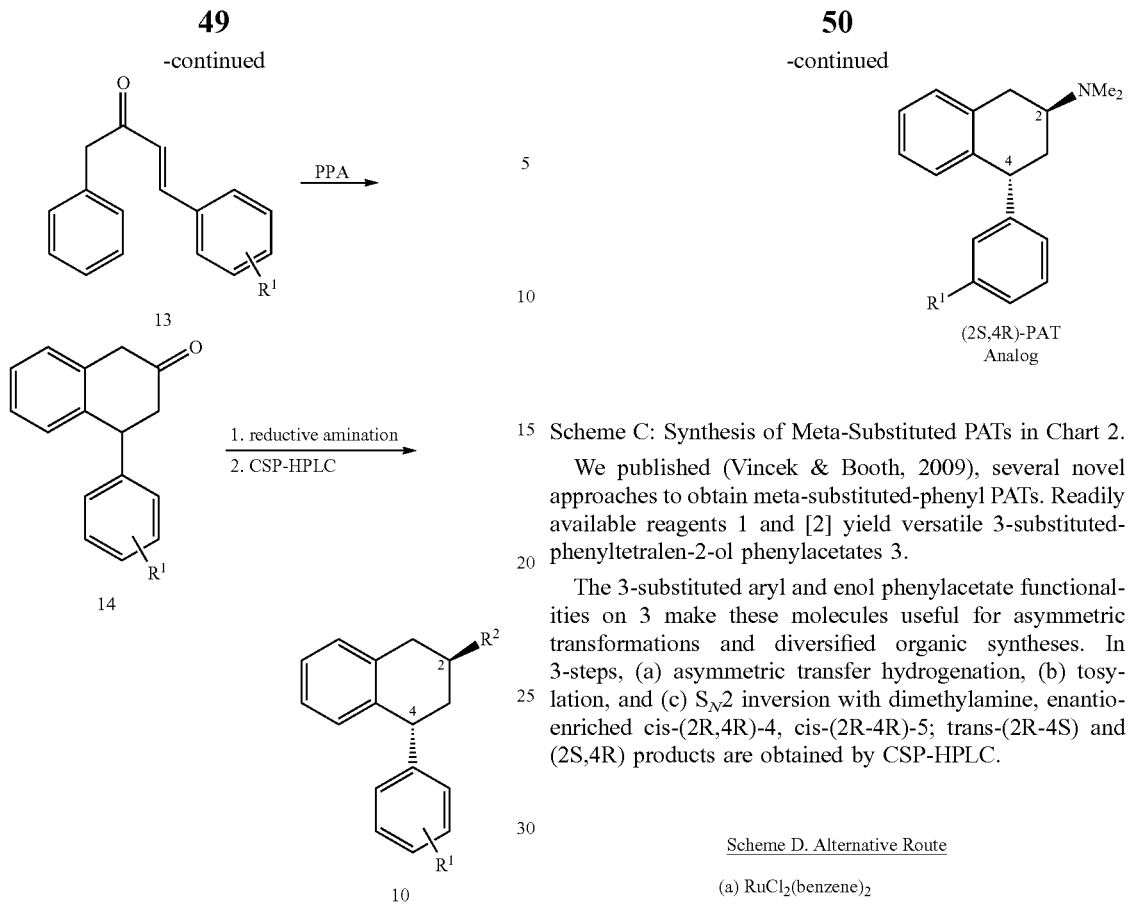

Scheme B: Alternative Approach.

Aldol condensation of phenyl acetone 11 with benzaldehyde or halobenzaldehydes 12 in presence of KOH affords enone derivatives 13. Tetralone intermediates 14 are obtained from treatment of 13 with polyphosphoric acid as we reported previously (Bucholtz 1999). Trans-(2S,4R)-PATs 10 are prepared from reductive amination of 14 (Abdel-Magid 1996), followed by CSP-HPLC.

Scheme C: Synthesis of Meta-Substituted PATs in Chart 2.

We published (Vincek & Booth, 2009), several novel approaches to obtain meta-substituted-phenyl PATs. Readily available reagents 1 and [2] yield versatile 3-substituted-phenyltetralen-2-ol phenylacetates 3.

The 3-substituted aryl and enol phenylacetate functionalities on 3 make these molecules useful for asymmetric transformations and diversified organic syntheses. In 3-steps, (a) asymmetric transfer hydrogenation, (b) tosylation, and (c) $S_N2$ inversion with dimethylamine, enantio-enriched cis-(2R,4R)-4, cis-(2R-4R)-5; trans-(2R-4S) and (2S,4R) products are obtained by CSP-HPLC.

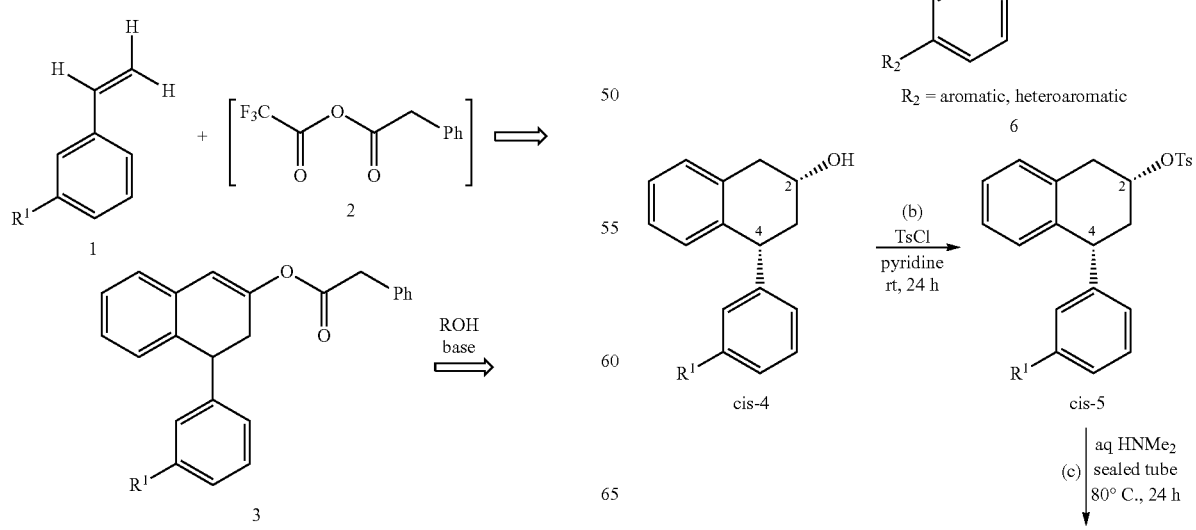

Scheme D: Alternative Approach.
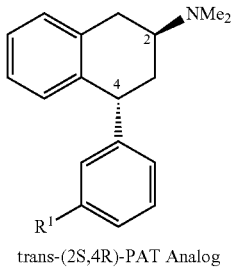
trans-(2S,4R)-PAT Analog
Suzuki coupling of 4-(3-bromophenyl)-tetralen-2-ol phenylacetate 3a (i.e., 3 in Scheme 1 where $R^1$=Br) with substituted-boronic acid in reaction (d) provides 4-(3-substituted-phenyl)-tetralen-2-ol phenylacetates 6 (Vincek & Booth, 2009). Many boronic acid Suzuki coupling reagents are available (Chemfiles, 2007).
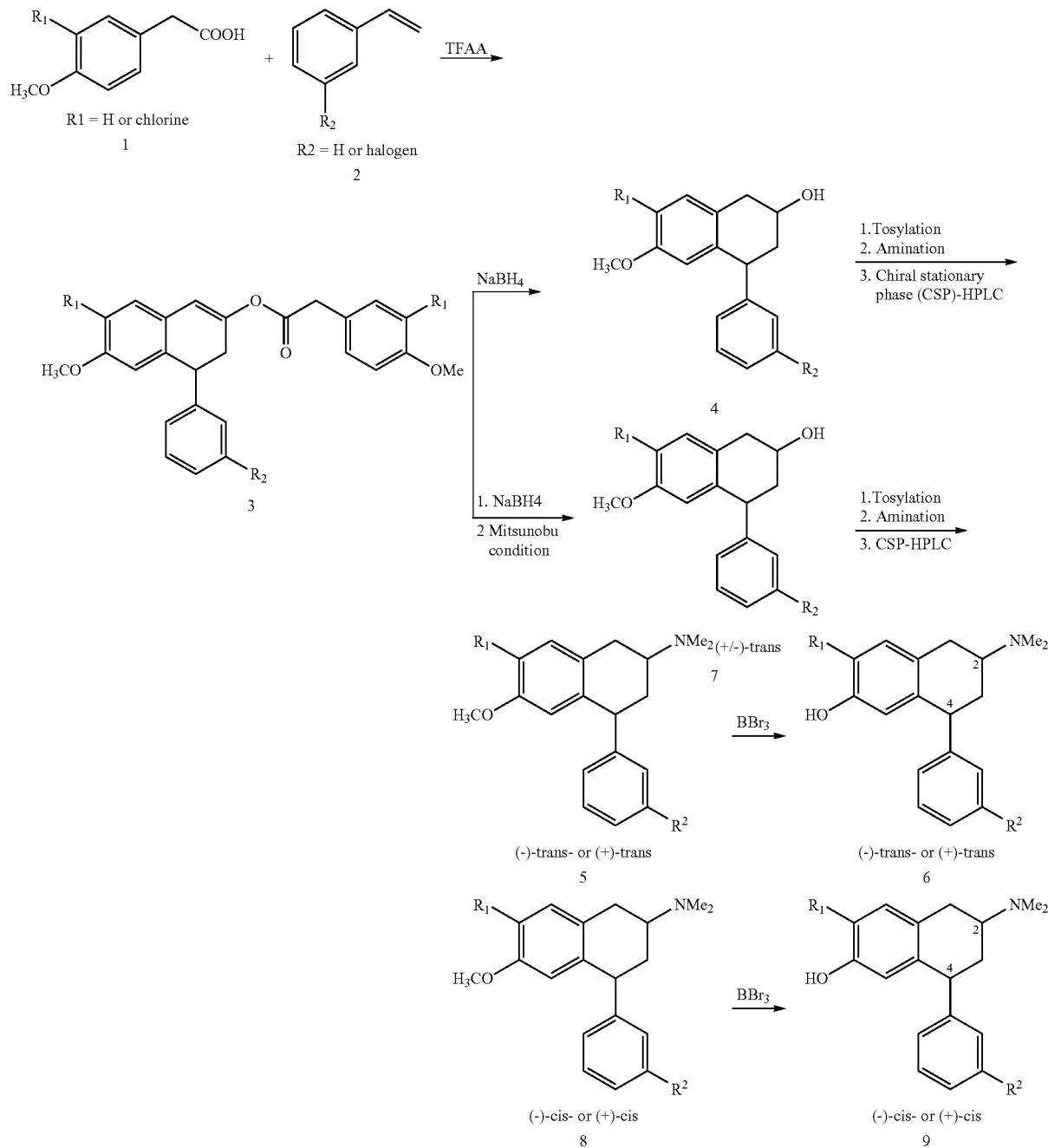

Scheme E: Synthesis of PAT with Tetrahydronapthyl Substituents in Chart 3.

Readily prepared 1 and commercially available 2 yield substituted phenyltetralen-2-ol phenylacetates 3 using trifluoro-acetic anhydride (TFAA) (Vincek & Booth, 2009). Compound 3 is reduced by sodium borohydride to afford racemic cis-ol 4 that is directly tosylated and converted to the trans-dimethylamine 5. CSP-HPLC is used to separate (+)-trans-(2R,4S)- and (−)-trans-(2S,4R)-5. These new PAT analogs could be reduced by boron tribromide to afford another series of new compounds 6. Conversion of 4 to 7 by the Mitsunobu reaction, followed by tosylation, amination and CSP-HPLC enantiomeric separation gives (+)- and (−)-cis-PATs 8 & 9.

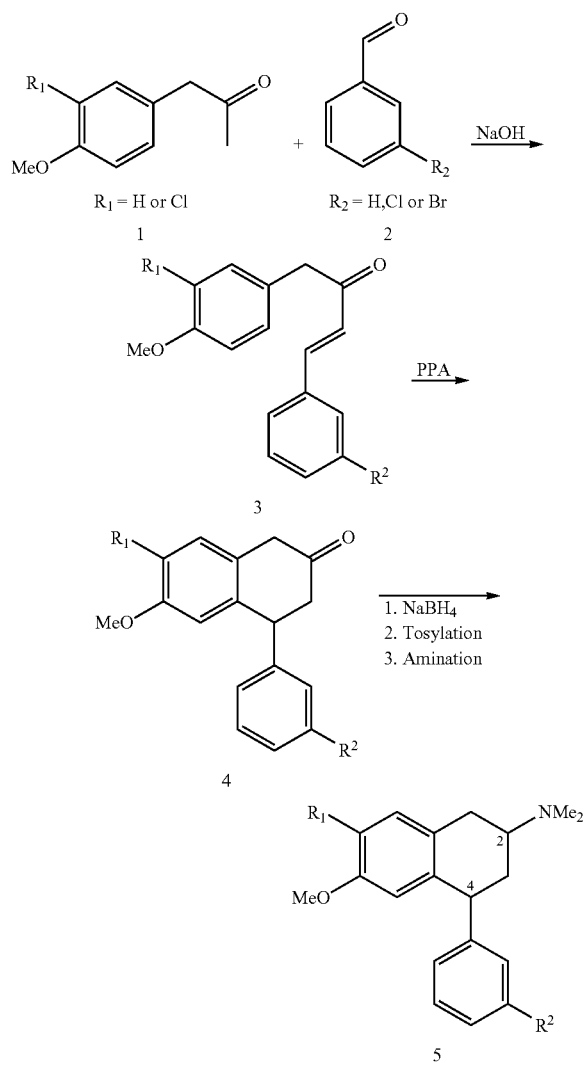

Scheme F: Alternative Approach:

We have previously used Scheme 6 (Bucholtz et al., 1999; Booth et al., 2009) wherein separation of racemic-cis and racemic-trans isomers by column chromatography is followed by diastereomeric recrystallization or CSP-HPLC to obtain single-enantiomer PAT analogs.

EXAMPLES

The invention is further illustrated by the following examples which are intended to illustrate but not limit the scope of the invention.

Example 1

Chemicals

All reagents were obtained from commercial suppliers and used without further purification. $^1$H and $^{13}$C NMR were collected at resonance frequencies 400 and 100 MHz correspondingly, in CDCl$_3$. The chemical shifts are reported in ppm from tetramethylsilane. Flash column chromatography was conducted using silica gel 60 (230-400 mesh). Melting points were determined on a Mel-Temp apparatus equipt with a mercury thermometer. HPLC chiral separations were determined by an HPLC instrument equipped with a Regis-Cell™ (5 μm, 25 cm×10 mm i.d.) column. Minor peaks (<5%) in some $^1$H & $^{13}$C NMR spectra were attributed to the formation of a regioisomer.

[$^3$H]-Ketanserin (specific activity 72.2 Ci/mmol) and myo-[2-$^3$H(N)]-Inositol (specific activity 18.5 Ci/mmol) were purchased from Perkin-Elmer Life Science (Boston, Mass.) and [N$^6$-methyl-$^3$H]-mesulergine (specific activity 72.0 Ci/mmol) from Amersham Biosciences (GE healthcare, Piscataway, N.J.). Other compounds were obtained in highest purity from Sigma-Aldrich (St. Louis, Mo.).

Clonal Cell Culture and Transfection

All cell lines are maintained by following ATCC suggestion, Chinese Hamster Ovary cells (CHO-K1, ATCC CCL-61) in Ham's F-12 medium supplemented with 10% fetal bovine serum, 1% sodium bicarbonate (Mediatech 25-035-CI), 10 IU/ml Penicillin and 10 ug/ml Streptomycin, and human embryonic kidney (HEK) 293 in minimum essential medium (Eagle) (MEM) with 2 mM L-glutamine adjusted to contain 1.5 g/L sodium bicarbonate, 0.1 mM non-essential amino acids, and 1.0 mM sodium pyruvate (90%) with 10% fetal bovine serum, 10 IU/ml Penicillin and 10 ug/ml Streptomycin. Cells are grown at 37° C. in a humidified incubator with 5% CO$_2$. The cDNAs encoding the human 5-HT$_{2A}$, 5-HT$_{2B}$, and 5-HT$_{2C}$ receptors (wild type) are purchased from UMR (Rolla, Mo.) for transient transfection of the clonal cells. For radioreceptor binding assays, 5-HT$_{2A}$, 5-HT$_{2B}$, and 5-HT$_{2C}$ receptor membranes are prepared from transfected CHO-K1 cells. For functional assays measuring activity of PLC/IP formation, transfected CHO-K1 cells are used for 5-HT$_{2A}$ and 5-HT$_{2C}$ receptors. For 5HT$_{2B}$ receptors, however, more robust and consistent results for the PLC/IP assay are obtained using transfected HEK cells (Setola et al., 2005). Twenty-four hours before transfection, cells are seeded at 40% confluence in 100 mm dishes for radioreceptor binding assays or at 10$^5$ cells per well in 12-well plates for functional assays. CHO-K1 cells are transiently transfected with 12 μg of plasmid and 32 μl of lipofectamine (Invitrogen) per 100 mm dish for radioreceptor binding assays, or, 0.8 μs plasmid and 4.0 μl of lipofectamine per well for functional assays. For 5-HT$_{2B}$ functional assays using HEK cells, 24 μg plasmid DNA is mixed with 60 μl of Lipofectamine 2000 (Invitrogen) to transfect 1-2×10$^6$ cells in a 10-cm plate. Cells are allowed to express transfected receptors for another 24 hrs (Herrick, 1997).

Radioreceptor Assays

Radioreceptor saturation and competition binding assays are performed using membrane homogenates, similar to our methods reported previously for the phylogenetically closely related histamine H$_1$ GPCR (Booth, 2002; Moniri et al., 2004). [$^3$H]-Ketanserin is used to radiolabel 5-HT$_{2A}$ receptors and [$^3$H]-mesulergine for 5-HT$_{2B}$ and 5-HT$_{2C}$ receptors. Briefly, forty-eight hours following CHO cell transfection, cells are harvested and homogenized in 50 mM Tris-HCl containing 0.1% ascorbic acid and 4.0 mM CaCl$_2$ at pH 7.4 (assay buffer). The homogenate is centrifuged at 35,000 g for 25 min and the resulting membrane pellet is re-suspended in assay buffer. Protein concentration is determined by the method of Lowry et al. (Lowry, 1951). For saturation binding assays, membrane suspension containing 100 μg protein is incubated with 0.1-5.0 nM [$^3$H]-ketanserin (5-HT$_{2A}$ receptors) or 0.1-20 nM [$^3$H]-mesulergine (5-HT$_{2B}$ and 5-HT$_{2C}$ receptors) in a total assay buffer volume of 250 μl. Non-specific binding is determined in the presence of 10 μM methysergide (5-HT$_{2A}$ receptors) or 1.0 μM mianserin (5-HT$_{2B}$ and 5-HT$_{2C}$ receptors). Competition binding assays are conducted similarly with 1.0 nM [$^3$H]-ketanserin or [$^3$H]-mesulergine. Incubation of radioreceptor binding assay mixtures is for 1.0 h at 37° C., with termination by rapid filtration through Whatman GF/B filters using a 96-well cell harvester (Tomtec, Hamden, Conn.). The membrane-bound [$^3$H]-radioligand retained on the filter discs is quantified by liquid scintillation spectrometry. Data are analyzed by non-linear regression using the sigmoidal curve-fitting algorithms in Prism 4.03 (GraphPad Software Inc., San Diego, Calif.). Ligand affinity is expressed as an approximation of K$_i$ values by conversion of the IC$_{50}$ data to K$_{0.5}$ values using the equation K$_{0.5}$=/C$_{50}$/1+L/K$_D$, where L is the concentration of radioligand having affinity K$_D$ (Cheng, 1973).

Assay for Activation of PLC and [$^3$H]-IP Formation

Functional activation of PLC is measured as [$^3$H]-IP formation in CHO cells transiently expressing serotonin 5-HT$_{2C}$ receptors or HEK cells transiently expressing serotonin 5-HT$_{2A}$ or 5-HT$_{2B}$ receptors, as previously reported (Moniri et al., 2004). Briefly, thirty-two hours following transfection, cells in inositol-free Dulbecco's modified Eagles medium (DMEM) are incubated for twelve hours with 1.0 μCi/ml myo-[2-$^3$H]-inositol, the radiolabeled precursor of the PLC-β substrate phosphatidylinositol. Cells then are washed and incubated in DMEM containing 10 mM lithium chloride, 10 μM pargyline (with addition of 5% dialyzed fetal bovine serum for HEK cells), and, various concentrations of test ligand for 45-60 min at 37° C. After aspiration of media, wells are lysed by incubation with 50 mM formic acid (15-60 min). Formic acid is neutralized with ammonium hydroxide and contents from each well are added to individual AG1-X8 200-400 formate resin anion exchange columns. Ammonium formate/formic acid (1.2 M/0.1 M) is used to elute [$^3$H]-IP directly into scintillation vials for counting of tritium by liquid scintillation spectrometry. Resulting data are analyzed using the nonlinear regression algorithms in Prism 4.03 and are expressed as mean percentage of control [$^3$H]-IP formation, with potency expressed as concentration required to stimulate (EC$_{50}$) or inhibit (IC$_{50}$) maximal basal (constitutive) [$^3$H]-IP formation by 50%±S.E.M. (n≥3).

Measurement of [$^3$H]-IP Formation in CHO-K1 and HEK Cells

Functional activation of PLC is measured as [$^3$H]-IP formation in CHO cells transiently expressing 5-HT$_{2A}$ or 5-HT$_{2C}$ receptors and HEK cells transiently expressing 5HT$_{2B}$ receptors, as previously reported by our lab (Booth, 2002; Moniri et al., 2004). Briefly, thirty-two hours following transfection, cells in inositol-free Dulbecco's modified Eagle's medium (DMEM) are labeled with 1 μCi/ml myo-[2-$^3$H]-inositol, a precursor of the PLC-β substrate phosphatidylinositol. Cells then are washed and incubated in DMEM containing 25 mM Hepes (pH 7.4), 10 mM LiCl, 10 μM pargyline (with addition of 5% dialyzed FBS for HEK cells), and various concentrations of test ligand for 45-60 min at 37° C. After aspiration of media, wells are placed on ice and lysed by incubation with 50 mM formic acid (15-60 min). Formic acid is neutralized with ammonium hydroxide and all contents from each well are added to individual AG1-X8 200-400 formate resin anion exchange columns. Ammonium formate/formic acid (1.2 M/0.1 M) is used to elute [$^3$H]-IP directly into scintillation vials for counting of tritium by liquid scintillation spectrometry. Resulting data are analyzed using the nonlinear regression algorithms in Prism 4.03 and are expressed as mean percentage of control [$^3$H]-IP formation, with potency expressed as concentration required to produce 50% maximal [$^3$H]-IP formation (EC$_{50}$) ±S.E.M (n≥3).

Example 2

Radioligand Saturation Binding Analysis of 5HT-Subtype Receptors:

There is no measurable specific radioligand binding using membranes prepared from null-transfected CHO and HEK cells. Using membranes prepared from CHO cells transiently transfected with 5-HT$_{2A}$, 5-HT$_{2B}$, or 5-HT$_{2C}$ cDNA, however, saturable specific radioligand binding occurs. [$^3$H]-Ketanserin binds to an apparent single population of 5HT$_{2A}$ receptors (B$_{max}$=1.73±0.11 pmol/mg protein) with high affinity (K$_D$=0.80±0.03 nM). Similarly, [$^3$H]-mesulergine labels a single population of 5HT$_{2B}$ receptors with B$_{max}$=1.13±0.39 pmol/mg protein and K$_D$=5.19±0.36 nM. [$^3$H]-mesulergine also labels an apparent single population of 5HT$_{2C}$ receptors (B$_{max}$=8.37±0.15 pmol/mg prot) with high affinity (K$_D$=0.88±0.03 nM).

Example 3

Kinase inhibition activity of RSKs and other kinases are known in the art. Assays for RSK activity are performed essentially as described in Jeffrey A. Smith, Celeste E. Poteet-Smith, Yarning Xu, Timothy M. Errington, Sidney M. Hecht, and Deborah A. Lannigan Cancer Res 2005; 65: (3), pp. 1027-1034. Feb. 1, 2005.

Example 4

Synthesis of Meta-Substituted Compounds and Separation of Enantiomers

General Synthetic Methods:

Relevant methodologies useful; in synthesizing compounds of the invention are known in the art and described in our synthetic medicinal chemistry publications (including e.g., Ghoneim, O. M.; Legere, J. A.; Golbraikh, A.; Tropsha, A.; Booth, R. G. Bioorg. Med. Chem. 2006, 14, 6640; Bucholtz, E. C.; Brown, R. L.; Tropsha, A.; Booth, R. G.; Wyrick, S. D. J. Med. Chem. 1999, 42, 3041; Wyrick S D, Booth R G, Myers A M, Owens C E, Kula N S, Baldessarini R J, McPhail A T, and Mailman R B (1993) Synthesis and pharmacological evaluation of 1-phenyl-3-amino1,2,3,4-tetrahydronaphthalenes as ligands for a novel receptor with sigma-like neuromodulatory activity. J Med Chem 36:2542-2551). In vitro pharmacological studies initially will use racemic cis and trans products. Racemic compounds can be resolved to (+)- and (−)-enantiomers by derivatization to the diastereomeric salt followed by differential crystallization or synthesized de novo using a chiral reduction step. Absolute configuration is assigned by single crystal X-ray crystallography or spectrophotometric methods (NMR, optical rotation) by comparison to pure enantiomers already synthesized. Products (as HCl salts) characterized for purity using NMR, elemental analysis, mass spectrometry, melting point and thin layer chromatography.

Scheme 1: Meta-Substituted Compounds:

Methods were modified from methodologies cited above and others known in the art. The Claisen-Schmidt reaction using meta-substituted aldehyde 2 gave the α,β-unsaturated ketone 3, which was cyclized to the ketone 4 and reduced using NaBH$_4$. The (±)-cis and (±)-trans free base 7 was converted to the (1R)-(−)- or (1S)-(+)-camphor-10-sulfonic acid diastereomeric salt, which underwent differential recrystallization to afford (+)- or (−)-enantiomer, that was alkylated to product 8.

Scheme 1

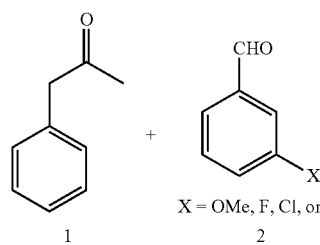

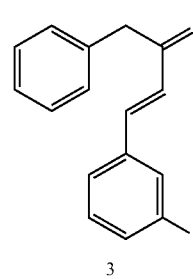

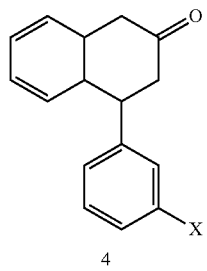

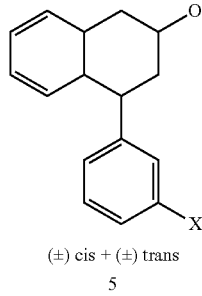

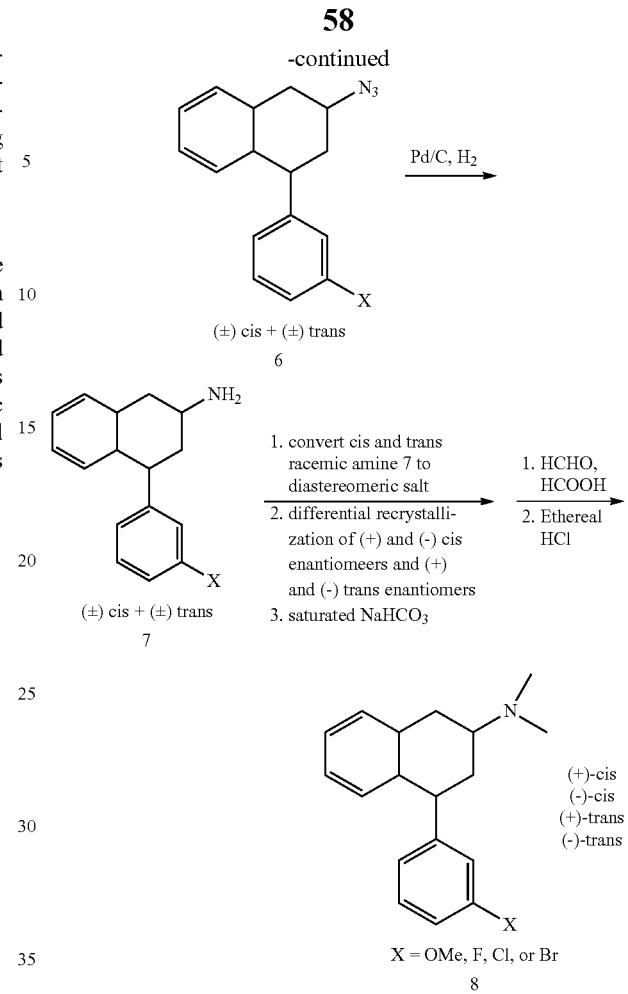

Scheme 2: Use of Chiral Reducing Agent to Obtain PAT Analog Stereoisomers:

Di-isopinocamphenyl-borane (DIP) analogs recently were reported as stereoselective reducing agents for ketones with structures similar to the ketone 4 in Scheme 2 (see, e.g., Cha et al., 2005).

Synthesis of New PAT Analogs with Changes to the C(1) Pendant Phenyl Substituent It was indicated based on binding, function, 3D QSAR, and molecular modeling results, that the (−)-trans-substituted phenyl aminotetralin (PAT) C(1) pendant phenyl moiety is critical to providing full-efficacy 5HT$_{2C}$ agonist activity without activation of 5HT$_{2A}$ and 5HT$_{2B}$ receptors.

Scheme 2

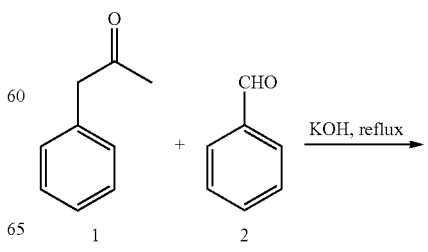

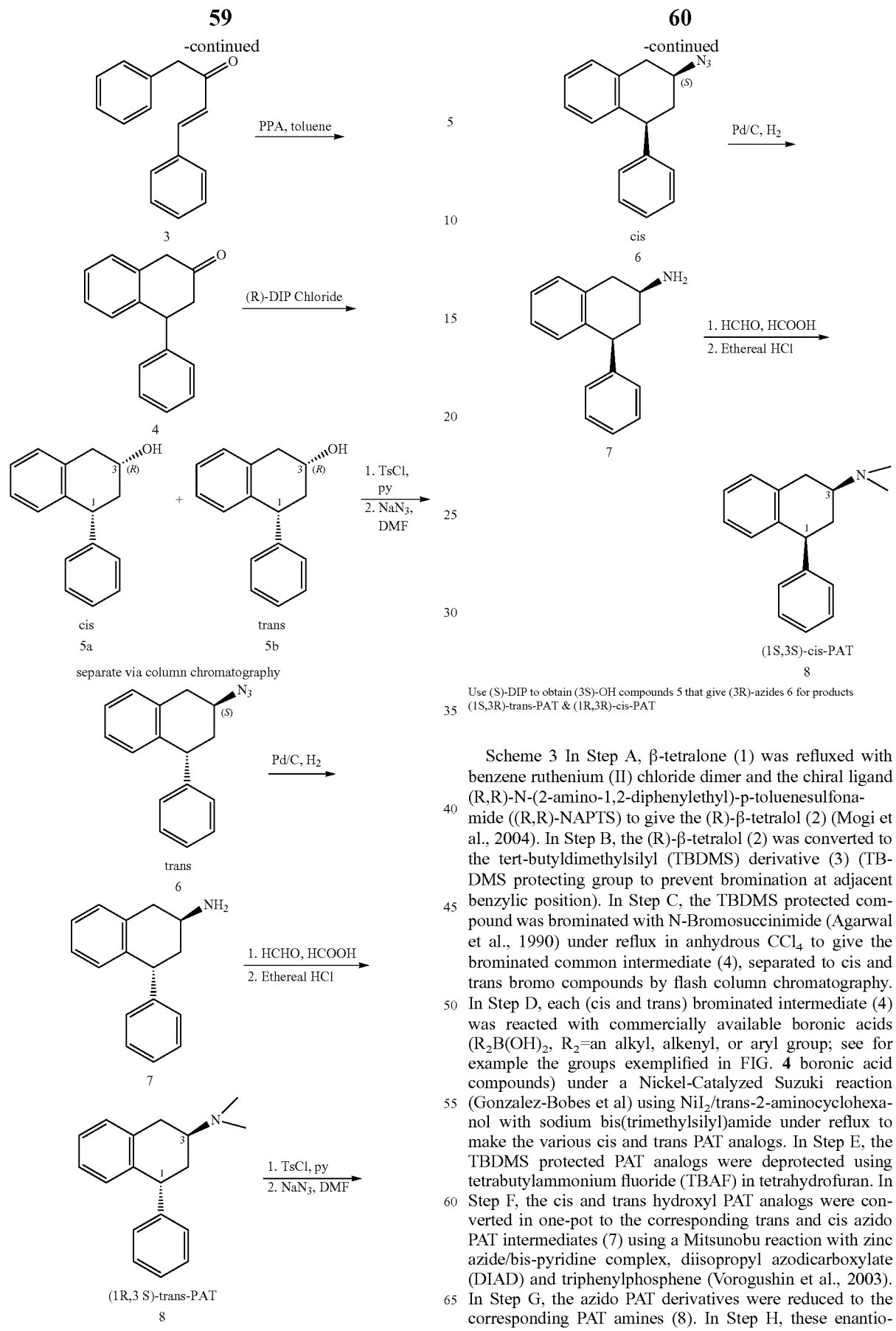

Scheme 3 In Step A, β-tetralone (1) was refluxed with benzene ruthenium (II) chloride dimer and the chiral ligand (R,R)-N-(2-amino-1,2-diphenylethyl)-p-toluenesulfonamide ((R,R)-NAPTS) to give the (R)-β-tetralol (2) (Mogi et al., 2004). In Step B, the (R)-β-tetralol (2) was converted to the tert-butyldimethylsilyl (TBDMS) derivative (3) (TBDMS protecting group to prevent bromination at adjacent benzylic position). In Step C, the TBDMS protected compound was brominated with N-Bromosuccinimide (Agarwal et al., 1990) under reflux in anhydrous $CCl_4$ to give the brominated common intermediate (4), separated to cis and trans bromo compounds by flash column chromatography. In Step D, each (cis and trans) brominated intermediate (4) was reacted with commercially available boronic acids ($R_2B(OH)_2$, $R_2$=an alkyl, alkenyl, or aryl group; see for example the groups exemplified in FIG. 4 boronic acid compounds) under a Nickel-Catalyzed Suzuki reaction (Gonzalez-Bobes et al) using $NiI_2$/trans-2-aminocyclohexanol with sodium bis(trimethylsilyl)amide under reflux to make the various cis and trans PAT analogs. In Step E, the TBDMS protected PAT analogs were deprotected using tetrabutylammonium fluoride (TBAF) in tetrahydrofuran. In Step F, the cis and trans hydroxyl PAT analogs were converted in one-pot to the corresponding trans and cis azido PAT intermediates (7) using a Mitsunobu reaction with zinc azide/bis-pyridine complex, diisopropyl azodicarboxylate (DIAD) and triphenylphosphene (Vorogushin et al., 2003). In Step G, the azido PAT derivatives were reduced to the corresponding PAT amines (8). In Step H, these enantiomeric cis and trans amines were converted to the dimethylated PAT analogs (9) using Eschweiler-Clarke methylation with formic acid/formaldehyde under reflux.

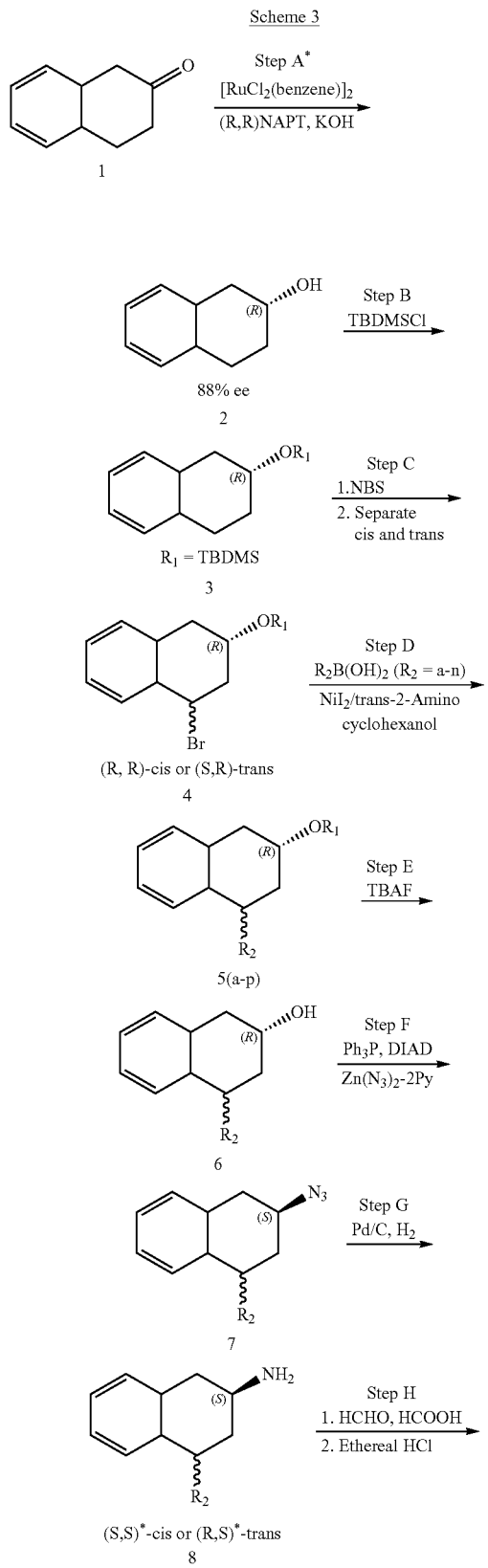

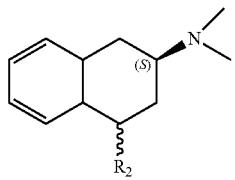

(S,S)-cis or (R,S)-trans
9

Compounds were resolved to (+)- and (−)-enantiomers by derivatization of the un-methylated free amine to the diastereomeric salt followed by differential crystallization or synthesized de novo using a chiral reduction step. Absolute configuration was assigned by single crystal X-ray crystallography or spectrophotometric methods (NMR, optical rotation) by comparison to pure enantiomers already synthesized. Products (as HCl salts) were characterized for purity using NMR, elemental analysis, mass spectrometry, melting point and thin layer chromatography. Compounds specifically delineated herein include those wherein $R_2$ is a chemical group or moiety (e.g., substituted or unsubstituted alkyl, alkenyl, or aryl group) attached to the boron atom in the boronic acid compounds of FIG. 4. Additional procedures for preparation of compounds herein are also described in PCT International Publication No. WO 2008/156707 (application no. PCT/US2008/007458).

Synthesis of Analogs

Trifluoroacetyl mixed anhydride and 3-halostyrenes (fluoro, chloro, and bromo) underwent cascade Friedel-Crafts cycli-acylalkylation, enolization, and O-acylation for 4-(3-halophenyl)-3,4-dihydronaphthalen-2-yl phenylacetates (bromo, 50%), without additional solvent. Base alcoholysis of masked 4-phenyltetral-2-one revealed the keto group for in situ asymmetric transfer hydrogenation. The bromo-derivative underwent Suzuki coupling with phenylboronic acid for 4-(biphen-3-yl)-3,4-dihydronaphthalen-2-yl phenylacetate, and provided a short efficient route to trans-4-phenyl-2-aminotetralins.

Cascade FC-CAA, enolization, and O-acylation was investigated with TFAA activated phenylacetic acid, styrene or 3-halostyrenes. Mild heating of reactive styrene 12a with [9] accelerated the inherently slow enolization (see, a) Nevy, J. B.; Hawkinson, D. C.; Blotny, G.; Yao, X.; Pollack, R. M. J. Am. Chem. Soc. 1997, 119, 12722. b) Yao, X.; Gold, M. A.; Pollack, R. M. J. Am. Chem. Soc. 1999, 121, 6220) of 3a to provide 4a (15%). In the absence of heating, complex mixtures resulted in loss of reactive 3a. Moderately reactive 3-halostyrenes with equimolar or up to 3-equiv of [9] provided halogenated 3 and 4. Fluorostyrene 12b with equimolar [9] gave major 3b (42%) and minor 4b (8%). Chlorostyrene 12c with 3-equiv of [9] gave 3c (70%). Further treatment of 3c with equimolar [9] gave 4c (38%). Warming to rt over 24 h bromostyrene 12c with 3-equiv of [9] gave 4d (50%), a 3-fold increase in yield from non-halogenated 4a.

TABLE 4

Cascade Conditions and Yields

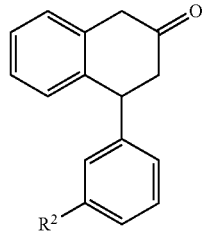

3a-d

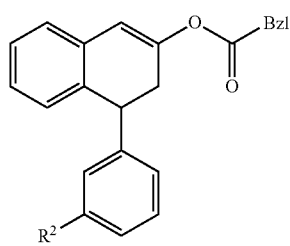

4a-d

9

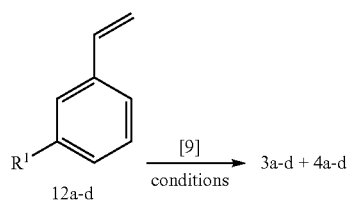

| R[1] | 12 | 3 (%)[a] | 4 (%)[a] | [9]:12[c] (mmol)[d] | temp (° C.) | t (h) |
|---|---|---|---|---|---|---|
| H | a | 0 | 15 | 3:1(20) | 0-60 | 0.5 |
| F | b | 42 | 8 | 1:1(10) | 0 | 0.5 |
| Cl | c | 70 | 0[b] | 3:1(10) | 0 | 0.5 |
| Br | d | 0 | 50 | 3:1(25) | 0-rt | 24[e] |

[a] isolated yield;
[b] 38% from 3c;
[c] mole ratio;
[d] mmols of 12;
[e] reaction time not minimized Scheme 4:

Suzuki coupling (see, a) Wolfe, J. P.; Singer, R, A.; Yang, B. H.; Buchwald, S. L. *J. Am. Chem. Soc.* 1999, 121, 9550. b) Wolfe, J. P.; Buchwald, S. L. *Angew. Chem. Int. Ed.* 1999, 38, 2413) of 4d with a phenylboronic acid (e.g., from Table 5) smoothly provided 4-(biphenyl-3-yl)-3,4-dihydro-naphthalen-2-yl phenyl-acetate 14, which were converted to the desired substituted phenyl aminotetralin according to protocols as in Scheme 3.

Scheme 4:

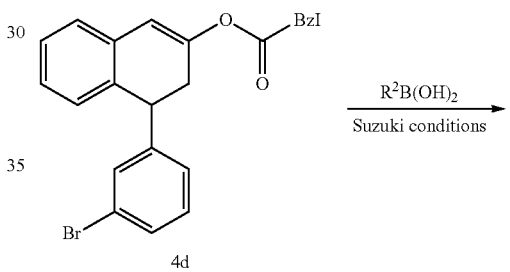

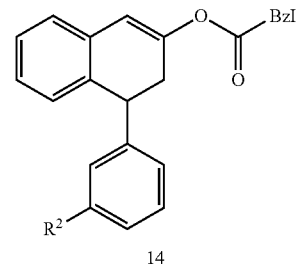

14

Example 5

Synthesis of CAT Compounds

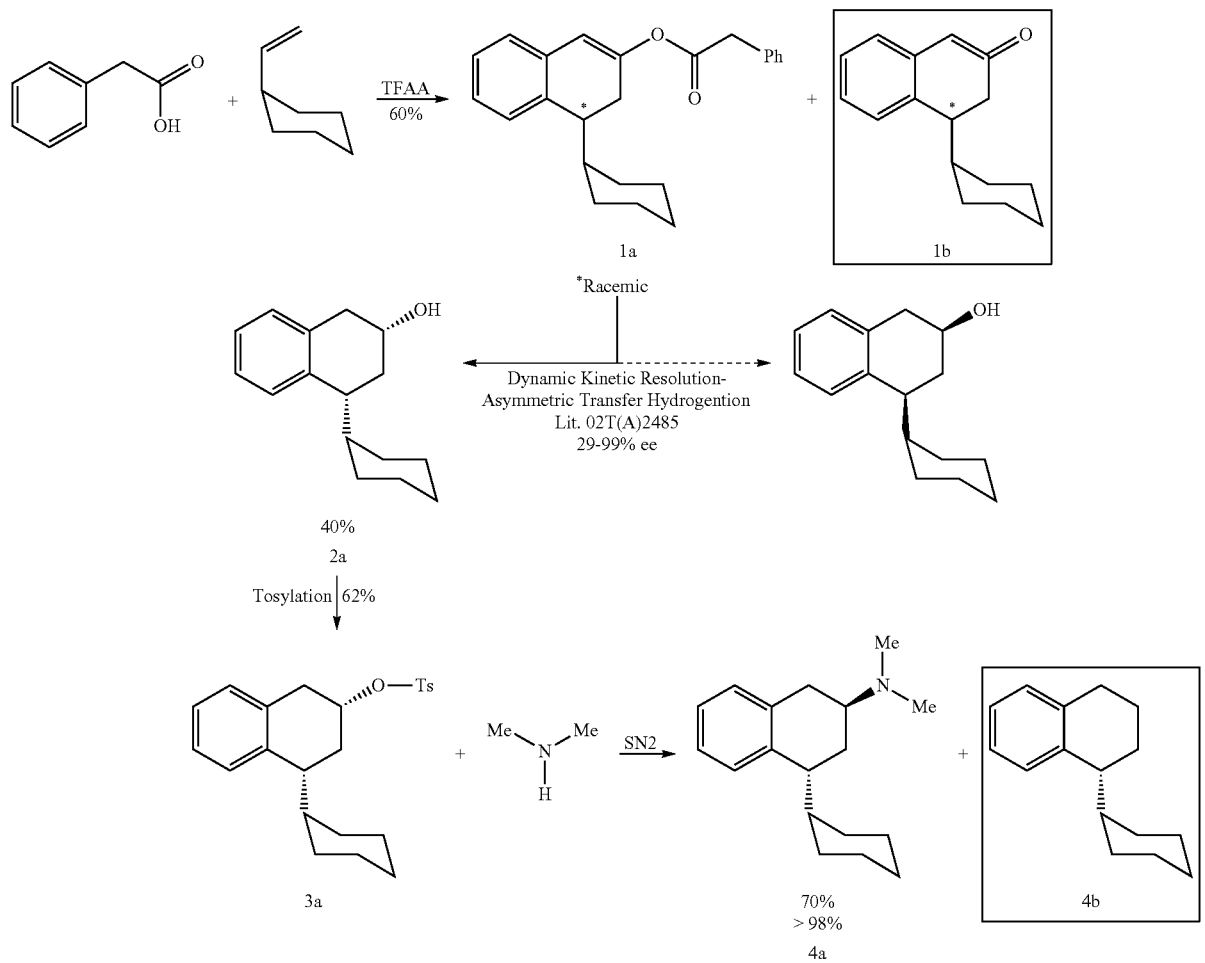

Scheme 5

4-Cyclohexyl-3,4-dihydronaphthalen-2-yl phenylacetate (1a)

(Gray A D, and Smyth T P (2001) Clean-chemistry synthesis of 2-tetralones in a single-stage acylation-cycloalkylation process. J Org Chem 66:7113-7117) Phenylacetic acid (10.9 g, 0.08 mol) was dissolved in trifluoroacetic anhydride TFAA (11 mL, 0.08 mol) at rt, to generate a mixed anhydride in situ. Nitrogen gas was used to push the mixed anhydride through a double ended needle to a separate flask containing vinylcyclohexane (0.04 mol), stirring at 60° C. After 30 min, the reaction was quenched with water (100 mL) and extracted with ethylacetate (100 mL, 3×). The organic layer was dried over sodium sulfate, filtered, and concentrated. The crude material was purified by column chromatography (Si-gel) to give racemic 1a (30%, oil) and 1b (~30%, 4-cyclohexyl-3,4-dihydronaphthalen-2(1H)-one). $^1$H NMR (CDCl3) j 0.92-1.26 (m, 5H), 1.40-1.44 (m, 1H), 1.57-1.76 (m, 5H), 2.36 (dd J=3.0, 17.1 Hz, 1H), 2.61 (dt, J=2.9, 7.0 Hz, 1H), 2.76 (ddd, J=2.5, 7.6, 17.0 Hz, 1H), 3.73 (s, 2H), 6.15 (d, J=2.3 Hz, 1H), 6.95 (dd, J=2.2, 7.2 Hz, 1H), 7.02-7.19 (m, 3H), 7.26-7.36 (m, 5H). $^{13}$C NMR (D$^6$-DMSO) j 25.9, 26.0, 26.1, 28.2, 29.2, 30.5, 40.2, 40.6, 43.5, 113.8, 126.1, 126.2, 126.5, 127.0, 128.4, 129.4, 132.5, 133.9, 135.3, 149.9, 169.6. Anal. Calcd for C24H26O2; C, 83.20; H, 7.56. Found: C, 83.02; H, 7.91. HRMS m/z Calcd for C24H26O2 346.1933 [M]$^+$, Found 346.1921.

(2R,4R)-4-Cyclohexyl-1,2,3,4-tetrahydronaphthalen-2-ol (2a)

(Peach, P, Cross D J, Kenny J A, Mann I, Houson I, Campbell L, Walsgrove T, and Wills M (2006) Asymmetric transfer hydrogenation of a,3-unsaturated, a-tosyloxy and a-substituted ketones. Tetrahedron 62:1864-1876), (Alcock N J, Mann I, Peach P, and Wills M (2002) Dynamic kinetic resolution-asymmetric transfer hydrogenation of 1-aryl-substituted cyclic ketones. Tetrahedron: Asymmetry 13:2485-2490), (Mogi M, Fuji K, and Node M (2004) Asymmetric reduction of methoxy substituted 3-tetralones using transfer hydrogenation. Tetrahedron: Asymmetry 15:3715-3717) Benzeneruthenium(II) chloride dimer (55 mg, 0.11 mmol) and (1R,2R)-(−)-N-(4-toluenesulfonyl)-1,2-diphenylethylenediamine (80 mg, 11 mmol) were mixed in iso-propanol (25 mL) and heated at 80° C. for 30 min, to generate the catalyst mixture. Separately, 4-cyclohexyl-3,4-dihydronaphthalen-2-yl phenylacetate 1a (950 mg, 2.8 mmol) was heated to 50° C. in iso-propanol (25 mL). Nitrogen gas was used to push the catalyst mixture through a double ended needle to the flask containing 1a, directly followed by a mixture of KOH (0.5 g) in iso-propanol (50 mL). After 3 hours, the reaction was filtered through a pad of silica gel on Celite and then concentrated under reduced pressure. The crude material was purified by column chromatography (Si-gel) to give 2a in a 40% yield.

(2R,4R)-4-Cyclohexyl-1,2,3,4-tetrahydronaphthalen-2-yl 4-methylbenzenesulfonate (3a)

(Wyrick S D, Booth R G, Myers A M, Owens C E, Kula N S, Baldessarini R J, McPhail A T, and Mailman R B (1993) Synthesis and pharmacological evaluation of 1-phenyl-3-amino1,2,3,4-tetrahydronaphthalenes as ligands for a novel receptor with sigma-like neuromodulatory activity. J Med Chem 36:2542-2551) (2R,4R)-4-Cyclohexyl-1,2,3,4-tetrahydronaphthalen-2-ol 2a (0.23 g, 0.1 mol), p-toluenesulfonyl chloride (0.20 g, 0.11 mol), and pyridine (1.5 mL) was stirred in solution for 24 hours at rt, under inert atmosphere ($N_2$). The solvent was removed and the crude material was purified by column chromatography (Si-gel) to give 3a in a 62% yield. HRMS m/z Calcd for C23H28O3S 407.1651 [M+Na]$^+$, Found 407.1631.

(2S,4R)-4-Cyclohexyl-N,N-dimethyl-1,2,3,4-tetrahydronaphthalen-2-amine (4a)

(Bosse K, Marineau J, Nason D M, Fliri A J, Segelstein B E, Desai K, and Volkmann R A (2006) Expanding the medicinal chemistry toolbox: stereospecific generation of methyl group-containing propylene linkers. Tetrahedron Letters 47:7285-7287) Dimethylamine (40% in $H_2O$, 6 mL) and (2R,4R)-4-cyclohexyl1,2,3,4-tetrahydronaphthalen-2-yl 4-methylbenzenesulfonate 3a (0.19 g, 0.5 mmol) were placed in a tube, sealed, and heated at 83° C. for 24 hours. The solvent was removed and the crude material was purified by column chromatography (Si-gel) to give 4a in a 70% yield and 5a, (30%, (R)-1-cyclohexyl-1,2-dihydronaphthalene). After bench chromatography, 4a was examined using chiral (RegisCell™, EtOH(15):hexanes (85)) HPLC technology to indicate ee above 98% by UV trace. $^1$H NMR (CDCl3) i 1.00-1.31 (m, 5H), 1.39-1.47 (m, 1H), 1.57-1.85 (m, 6H), 2.48-2.52 (m, 1H), 2.72-2.77 (m, 1H), 2.80 (s, 6H), 3.03 (dd, J=9.0, 16.6 Hz, 1H), 3.34 (dd, J=6.8, 16.0 Hz, 1H), 3.72-3.75 (m, 1H), 7.09-7.29 (m, 4H). $^{13}$C NMR (CDCl3) 26.5, 26.8, 27.3, 30.2, 31.8, 32.3, 41.6, 41.9, 43.5, 56.8, 124.9, 125.7, 129.1, 129.2, 136.0, 139.7. HRMS Calcd for C18H27N, 258.2216 [M+H]$^+$, Found 258.2220. For pharmacological studies, the free base was converted to the HCl salt; MP: 174-176° C. Anal. Calcd for C18H27N+HCl+$H_2O$: C, 69.32; H, 9.70; N, 4.49. Found: C, 69.48; H, 9.98, N, 4.34.

Example 6

Pharmacological activity of CAT at serotonin 5HT2A, 5HT2B, 5HT2C, and histamine H1 G protein-coupled receptors.

Figure 2:
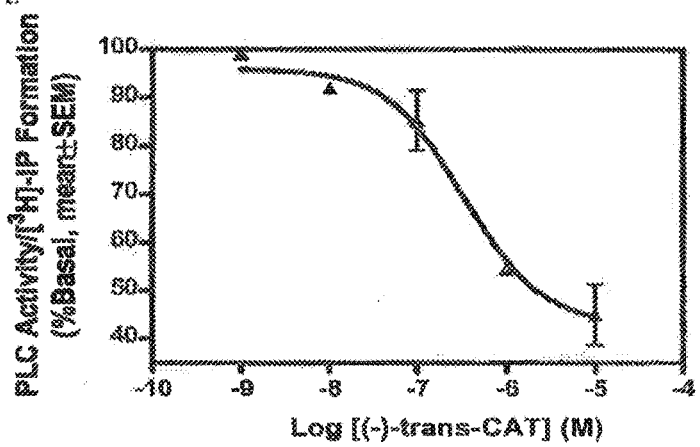
FIGS. 2A-C illustrate representative curves of (−)-trans-CAT effect on activity of PLC activity/IP formation in HEK 293 cells transiently expressing wild type $5HT_{2A}$, $5HT_{2B}$, $5HT_{2C}$ receptors. Data shows that (−)-trans-CAT is an inverse agonist of $5HT_{2A}$, $5HT_{2B}$ and $5HT_{2C}$ receptors.
Figure 2:
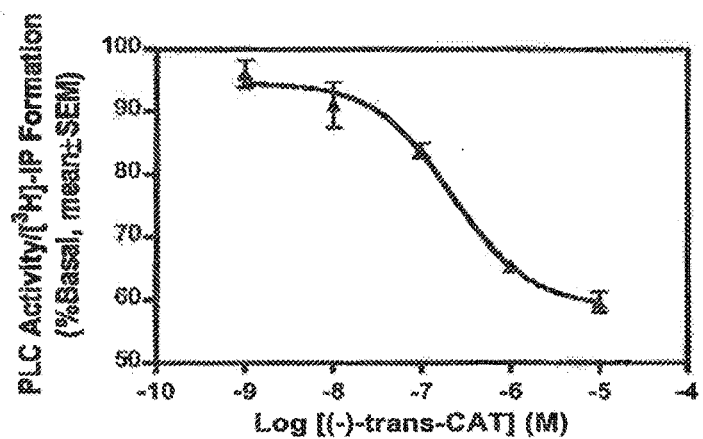
Figure 2C:
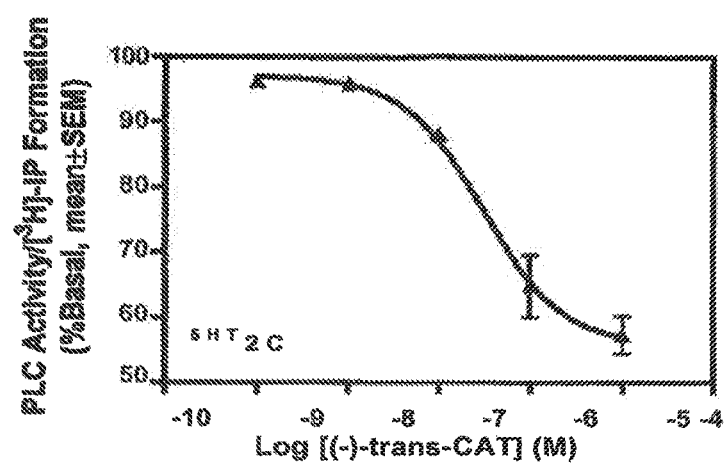
Figure 3:
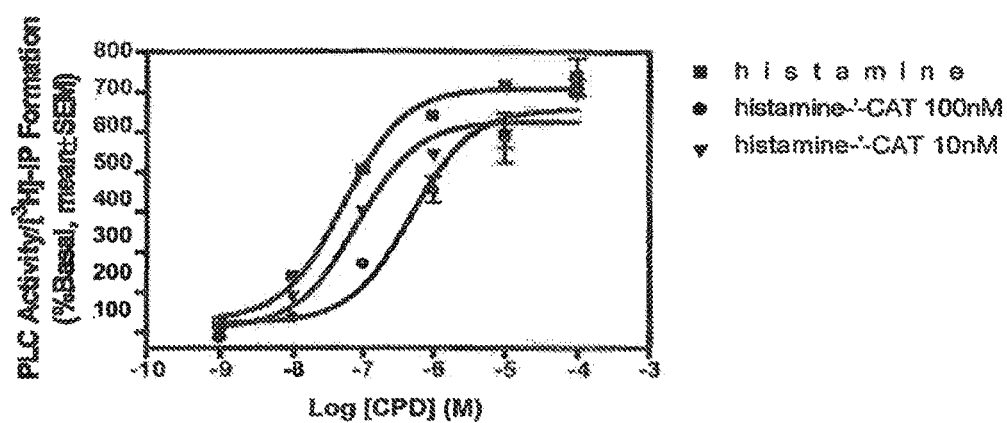
FIG. 3 illustrates that histamine activation of Histamine H1 receptor-mediated stimulation of PLC activity/[3H]-IP formation is competitively antagonized by (−)-trans-CAT.

The activity of (−)-trans-CAT and (+)-trans-CAT was assessed using protocols essentially as known in the art and described herein. The results are delineated in the tables below and figures herein (e.g., FIGS. 1-3).

Molecular structures of (+)-(2R,4S)- and (−)-(2S,4R)-4-cyclohexyl-N,Ndimethyl-1,2,3,4-tetrahydronaphthalen-2-amine (alternatively, 4-cyclohexyl-2-dimethylaminotetralin, CAT):

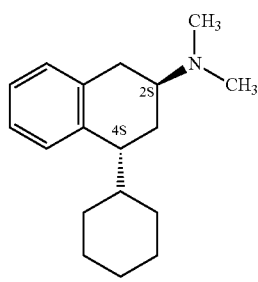

(−)-trans-CAT

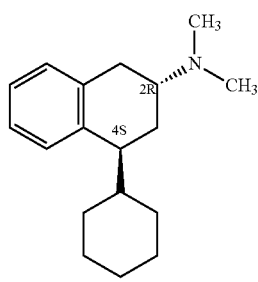

(+)-trans-CAT

TABLE 5

Summary of competitive binding and activity of PLC/IP formation of (−)-trans-CAT

| Receptors | Ki (nM) | nH | PLC/IP formation | |
|---|---|---|---|---|
| | | | IC$_{50}$ (μM) | I$_{MAX}$ (% Basal) |
| 5HT$_{2A}$ | 1.61 ± 0.05 | 1.26 ± 0.01 | 0.13 ± 0.02 | 48.45 ± 5.50 |
| 5HT$_{2B}$ | 23.70 ± 0.79 | 0.81 ± 0.02 | 0.25 ± 0.03 | 56.80 ± 2.13 |
| 5HT$_{2C}$ | 13.75 ± 2.17 | 1.13 ± 0.18 | 0.19 ± 0.04 | 60.65 ± 2.94 |
| Histamine H1 WT | 1.58 ± 0.50 | 1.01 ± 0.05 | Competitive antagonist | |

TABLE 6

Summary of competitive binding of (+)-trans-CAT

| Receptors | Ki (nM) | nH | PLC/IP formation | |
|---|---|---|---|---|
| | | | IC$_{50}$ (μM) | I$_{MAX}$ (% Basal) |
| 5HT$_{2A}$ | 78.18 ± 4.0 | 0.77 ± 0.20 | — | — |
| 5HT$_{2B}$ | 1006.56 ± 140 | 0.75 ± 0.12 | — | — |
| 5HT$_{2C}$ | 28.95 ± 4.40 | 1.20 ± 0.26 | — | — |
| Histamine H1 WT | 1.70 ± 0.00 | 1.02 ± 0.00 | — | — |

Summary of Pharmacological Data of (−)-Trans-CAT Regarding Affinity for 442 Different Kinases.

Molecular structure of (−)-(2S,4R)-4-cyclohexyl-N,N-dimethyl-1,2,3,4-tetrahydmnaphthalen-2-amine (alternatively, 4-cyclohexyl-2-dimethylaminotetralin, CAT)

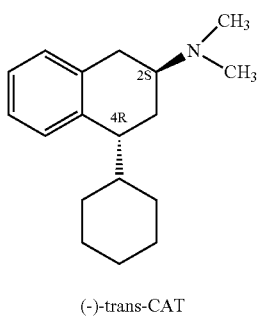 [SMILES: CN(C)[C@@H]1Cc2ccccc2[C@@H](C2CCCCC2)C1]

(−)-trans-CAT (−)-trans-CAT binds very potently to RSK 3 (80% inhibition of labeled tag binding at 1.0 uM CAT)

(−)-trans-CAT binds very potently to RSK 4 (80% inhibition of labeled tag binding at 1.0 uM CAT)

(−)-trans-CAT has modest affinity to RSK 1 (20% inhibition of tag binding at 1.0 uM CAT).

At concentrations up to 1.0 uM, (−)-trans-CAT did not exhibit similarly significant binding to RSK 2 relative to those kinases delineated above, indicating significant selectivity.

At concentrations up to 1.0 uM, (−)-trans-CAT did not exhibit as significant binding to 438 other kinases (see Table 4) tested relative to those kinases delineated above, indicating significant selectivity.

There is currently no molecule reported with the extremely high specificity of (−)-trans-CAT for inhibition of RSKs 3 and 4 over RSKs 1(minor binding) and 2 (no binding). There is currently no molecule reported with the extremely high specificity of (−)-trans-CAT for inhibition of RSKs (1, 3 and 4) from RSK 2 and 438 other kinases.

Example 7

The 5-HT2 functional activity of compounds can be assessed by methods known in the art, including those delineated in PCT International Publication No.

REFERENCES

Arjona A A, Pooler A M, Lee R K, Wurtman R J. Effect of a 5-$HT_{2C}$ serotonin agonist, dexnorfenfluramine, on amyloid precursor protein metabolism in guinea pigs. Brain Res. 2002 951:135-140.

Baldessarini R J, Tarazi F I. Pharmacotherapy of Psychosis and mania. In: Brunton L L, Laxo J S, Parker K L, eds. The Pharmacological Basis of Therapeutics. 11th ed. New York: McGraw-Hill, 2006:461-500.

Bubar M J, Cunningham K A. Distribution of serotonin 5-HT(2C) receptors in the ventral tegmental area. Neuroscience. 2007 (doi: 10.1016/j.neuroscience.2006.12.071).

Bubar M J, Cunningham K A. Serotonin 5-HT2A and 5-HT2C receptors as potential targets for modulation of psychostimulant use and dependence. Current Topics and Medicinal Chemistry 2006; 6:1971-1985.

Connolly H M, Crary J L, McGoon M D, Hensrud D D, Edwards B S, Edwards W D, Schaff H V. Valvular heart disease associated with fenfluramine-phentermine N Engl J Med. 1997; 337:581-5888. Erratum in: N Engl J Med 1997; 337:1783.

Fitzgerald L W, Burn T C, Brown B S, Patterson J P, Corjay M H, Valentine P A, Sun J H, Link J R, Abbaszade I, Hollis J M, et al. Possible role of valvular serotonin 5-HT(2B) receptors in the cardiopathy associated with fenfluramine. Mol Pharmacol 2000 57: 75-81.

Fletcher P J, Grottick A J, Higgins G A. Differential effects of the 5-HT(2A) receptor antagonist M100907 and the 5-HT(2C) receptor antagonist SB242084 on cocaine-induced locomotor activity, cocaine self-administration and cocaine-induced reinstatement of responding. Neuropsychopharmacology 2002 27:576-586.

Frank M G, Stryker M P, Tecott L H. Sleep and sleep homeostasis in mice lacking the 5-HT2c receptor. Neuropsychopharmacology. 2002 27:869-873.

Ghoneim et al., Bioorg. Med. Chem., 14, 6640-6658 (2006).

Giorgetti M, Tecott L H. Contributions of 5-HT(2C) receptors to multiple actions of central serotonin systems. Eur J Pharmacol. 2004 488:1-9.

Heisler L K, Chu H M, Tecott L H. Epilepsy and obesity in serotonin 5-HT2C receptor mutant mice. Ann N Y Acad Sci. 1998 861:74-78.

Heisler L K, Cowley M A, Tecott L H, Fan W, Low M J, Smart J L, Rubinstein M, Tatro J B, Marcus J N, Holstege H, et al. Activation of central melanocortin pathways by fenfluramine. Science (Wash DC) 2002 297: 609-611.

Heisler L K, Tecott L H. A paradoxical locomotor response in serotonin 5-HT(2C) receptor mutant mice. J Neurosci. 2000 20:RC71.

Heisler L K, Zhou L, Bajwa P, Hsu J, Tecott L H Serotonin 5-HT(2C) receptors regulate anxiety-like behavior. Genes Brain Behay. 2007 (DOI 10.1111/j.1601-183X.2007.00316.x)

Jensen M D. Potential role of new therapies in modifying cardiovascular risk in overweight patients with metabolic risk factors. Obesity. 2006 14:1435-149S.

Julius D, Huang K N, Livelli T J, Axel R, Jessel T M. The 5HT2 receptor defines a family of structurally distinct but functionally conserved serotonin receptors. Proc. Natl. Acad. Sci. 1990 87:928-932.

Julius D, MacDermott A B, Axel R, Jessell T M. Molecular Characterization of a functional cDNA encoding the serotonin 1c receptor. Science 1988 241:558-564.

Kennett G A, Pittaway K, Blackburn T P: Evidence that 5-HT2C receptor antagonists are anxiolytic in the rat Geller-Seifter model of anxiety. Psychopharmacology (Berl.) (1994) 114:90-96.

Launay J M, Herve P, Peoc'h K, Tournois C, Callebert J, Nebigil C G, Etienne N, Drouet L, Humbert M, Simonneau G, et al. Function of the serotonin 5-hydroxytryptamine 2B receptor in pulmonary hypertension. Nat Med 2002 8: 1129-1135.

Marquis K L, Sabb A L, Logue S F, Brennan J A, Piesla M J, Comery T A, Grauer S M, Ashby C R Jr, Nguyen H Q, Dawson L A, Barrett J E, Stack G, Meltzer H Y, Harrison B L, Rosenzweig-Lipson S. WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. J Pharmacol Exp Ther. 2007 320:486-496.

Muller C P, Huston J P. Determining the region-specific contributions of 5-HT receptors to the psychostimulant effects of cocaine. Trends Pharmacol Sci. 2006 27:105-112.

Nichols D E. Hallucinogens, Pharmacol. Ther. 2004 101: 131-181.

Nilsson B M. 5-Hydroxytryptamine 2C (5-HT2C) receptor agonists as potential antiobesity agents. J Med Chem. 2006 49:4023-4034.

Palvimaki E P, Roth B L, Majasuo H, Laakso A, Kuoppamaki M, Syvalahti E, Hietala J. Interactions of selective serotonin reuptake inhibitors with the serotonin 5-HT2c receptor. sychopharmacology (Berl). 1996 126:234-240.

Pouwels H M, Smeets J L, Cheriex E C, Wouters E F. Pulmonary hypertension and fenfluramine. Eur Respir J. 1990 May; 3(5):606-7.

Raymond J R. Mukhin Y V. Gelasco A. Turner J. Collinsworth G. Gettys T W. Grewal J S. Garnovskaya M N. Multiplicity of mechanisms of serotonin receptor signal transduction. Pharmacol Ther. 2001 92:179-212.

Reynolds G P, Yao Z, Zhang X, Sun J, Zhang Z. Pharmacogenetics of treatment in first-episode schizophrenia: D3 and 5-HT2C receptor polymorphisms separately associate with positive and negative symptom response. Eur Neuropsychopharmacol. 2005 March; 15(2):143-51.

Rocha B A, Goulding E H, O'Dell L E, Mead A N, Coufal N G, Parsons L H, Tecott L H. Enhanced locomotor, reinforcing, and neurochemical effects of cocaine in serotonin 5-hydroxytryptamine 2C receptor mutant mice. J Neurosci. 2002; 22:10039-10045.

Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis K L. Antidepressantlike effects of the novel, selective, 5-HT(2C) receptor agonist WAY-163909 in rodents. Psychopharmacology (Berl). 2007 192:159-170.

Roth B L. Drugs and valvular heart disease. N Engl J Med. 2007; 356:6-9.

Rothman R B, Baumann M H, Savage J E, Rauser L, McBride A, Hufeisen S J, and Roth B L. Evidence for possible involvement of 5-HT(2B) receptors in the cardiac valvulopathy associated with fenfluramine and other serotonergic medications. Circulation 2000 102: 2836-2841.

Saltzman A G, Morse B, Whitman M M, Ivanshchenko Y, Jaye M, Felder S. Cloning of the human serotonin 5-HT2 and 5-HT1C receptor subtypes. Biochem Biophys Res Commun. 1991 181:1469-7148.

Sanders-Bush E, Mayer S E. Serotonin Receptor Agonists and Antagonists. Chapter 11, in Goodman and Gilman's The Pharmacological Basis of Therapeutics 11$^{th}$ Edition. Brunton L L, Lazo J S, Parker K L, Editors, McGranw-Hill, New York, 297-315, 2006.

Sard H, Kumaran G, Morency C, Roth B L, Toth B A, He P, Shuster L. SAR of psilocybin analogs: discovery of a selective 5-HT 2C agonist. Bioorg Med Chem Lett. 2005 15:4555-4559.

Segman R H, Heresco-levy U, Finkel B, Inbar R, Neeman T, Schlafman M, Dorevitch A, Yakir A, Lerner A, Goltser T, Shelevoy A, Lerer B. Association between the serotonin 2C receptor gene and tardive dyskinesia in chronic schizophrenia: additive contribution of 5-HT2CSer and DRD3Gly alleles to susceptibility, Psychopharmacology 2000 152:408-413.

Setola V, Dukat M, Glennon R A, Roth B L. Molecular determinants for the interaction of the valvulopathic anorexigen norfenfluramine with the 5-HT$_{2B}$ receptor. Mol Pharmacol 2005 68:20-33.

Simansky K J. NIH symposium series: ingestive mechanisms in obesity, substance abuse and mental disorders. Physiology & Behavior 2005; 86: 1-4.

Siuciak J A, Chapin D S, McCarthy S A, Guanowsky V, Brown J, Chiang P, Marala R, Patterson T, Seymour P A, Swick A, Iredale P A. CP-809,101, a selective 5-HT2C agonist, shows activity in animal models of antipsychotic activity. Neuropharmacology. 2007 52:279-290.

Smith S R, Prosser W, Donahue D, Anderson C, Shanahan W. Lorcaserin Phase 2b Clinical Study. American Diabetes Association, 2006.

Stein T D, Anders N J, DeCarli C, Chan S L, Mattson M P, Johnson J A. Neutralization of transthyretin reverses the neuroprotective effects of secreted amyloid precursor protein (APP) in APP$_{Sw}$ mice resulting in tau phosphorylation and loss of hippocampal neurons: support for the amyloid hypothesis. J. Neurosci. 2004 24:7707-7717.

Tecott L H, Sun L M, Akana S F, Strack A M, Lowenstein D H, Dallman M F, Julius D. Eating disorder and epilepsy in mice lacking 5-HT2c serotonin receptors. Nature. 1995 374:542-546

Tohda M, Takasu T, Nomura Y. Effects of antidepressants on serotonin-evoked current in Xenopus oocytes injected with rat brain mRNA. Eur J Pharmacol. 1989166:57-63.

Veenstra-VanderWeele J, G. M. Anderson G M, Cook E H. Pharmacogenetics and the serotonin system: initial studies and furure directions. Eur. J. Pharmacol. 2000 410: 65-181.

Vickers S P, Dourish C T, and Kennett G A. Evidence that hypophagia induced by D-fenfluramine and D-norfenfluramine in the rat is mediated by 5-HT2C receptors. Neuropharmacology 2001 41: 200-209.

Vickers, S. P., Clifton, P. G., Dourish, C. T. and Tecott, L. H., 1999. Reduced satiating effect of d-fenfluramine in serotonin 5-HT2C receptor mutant mice. Psychopharmacology 1999 143:309-314.

Agarwal R, Boyd D R, McMordie RAS, O'Kane G A, Porter P, Sharma N D, Dalton H, Gray D J. J. Chiral arene hydrates of naphthalene: Enzymatic and chemical syntheses. Chem Soc Chem Commun. 1990 1711-1713.

Mogi M, Fugi K, Node M. Asymmetric reduction of methoxy substituted β-tetralones using hydrogenation. Tetrahedron: Asymmetry. 2004 15:3715-3717.

Vorogushin A V, Predeus A, Wuff W D, Hansen H. Diels-Alder reaction-aromatization approach toward functionalized ring C allocolchicinoids. Enantioselective total synthesis of (-)-7S-Allocolchicine. J Org Chem.

The recitation of a listing of elements in any definition of a variable herein includes definitions of that variable as any single element or combination of listed elements. The recitation of an element, or an embodiment herein includes that element or embodiment as any single element or embodiment or in combination with any other element, embodiments or portions thereof.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A method of treating a GPCR-mediated disorder in a subject comprising administering to the subject identified as in need thereof a compound of formula (I), or salt thereof, wherein the GPCR-mediated disorder is a neuropsychiatric disorder, a neurodegenerative disorder, a neurological disorder, a cardiovascular disorder, a gastrointestinal disorder, or a genito-urinary tract disorder:

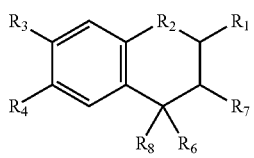
(I)

wherein,
R¹ is independently H, NH$_2$, NH(R'), N(R')$_2$; or

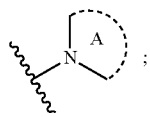

wherein ring A is a 3-8 membered heterocyclic or heteroaryl, containing 0-3 additional heteroatoms selected from O, N and S; wherein ring A is optionally substituted;
each R' is independently alkyl, alkenyl, or alkynyl, each of which may be optionally substituted;
R$_2$ is independently —(CH$_2$)n-;
each n is independently 1 or 2;
R$_3$ is independently H, OH, or halo;
R$_4$ is independently H, OH, or halo
each R$_5$ is independently alkyl, aryl, halo, nitro, amino, heteroaryl, cycloalkyl, heterocyclic, or alkoxy;
R$_6$ is independently H or alkyl;
R$_7$ independently H, or N(alkyl)$_2$; and
each R$_8$ is independently cycloalkyl, heteroaryl, or heterocyclic, each optionally substituted with 1, 2, 3, or 4 independent R$_5$;
or salt, hydrate or solvate thereof;
wherein the neuropsychiatric disorder is obesity, addiction, cocaine addiction, amphetamine/methamphetamine addiction, anxiety, depression, schizophrenia, or sleep disorders, the neurodegenerative disorder is Parkinson's Disease or Alzheimer's Disease, the neurological disorder is epilepsy, the cardiovascular disorder is hypertension, the gastrointestinal disorder is irritable bowel syndrome, and the genito-urinary tract disorder is bladder control.

2. The method of claim 1, wherein the compound of formula (I) is

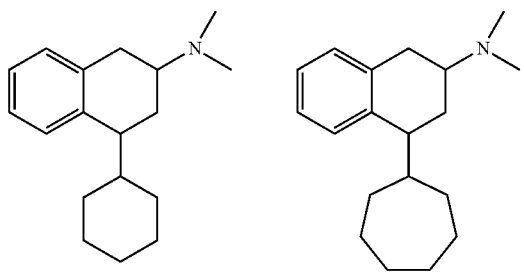 [SMILES: CN(C)C1Cc2ccccc2C(C2CCCCC2)C1 ; CN(C)C1Cc2ccccc2C(C2CCCCCC2)C1]

or salt thereof.

3. The method of claim 1, wherein in the compound of formula (I), R$_1$ is —NMe$_2$, or

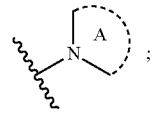

wherein ring A is a 3-8 membered heterocyclic or heteroaryl, containing 0-3 additional heteroatoms selected from O, N and S; wherein ring A is optionally substituted.

4. The method of claim 1, wherein in the compound of formula (I), R$_8$ is cycloalkyl optionally substituted with 1, 2, 3, or 4 independent R$_5$.

5. The method of claim 1, wherein the disorder is cocaine addiction or amphetamine or methamphetamine addiction.

6. The method of claim 1, wherein the disorder is obesity.

7. A method of treating a GPCR-mediated disorder in a subject comprising administering to the subject identified as in need thereof a compound of formula (I), or salt thereof, wherein the GPCR-mediated disorder is a neuropsychiatric disorder, a neurodegenerative disorder, a neurological disorder, a cardiovascular disorder, a gastrointestinal disorder, or a genito-urinary tract disorder:

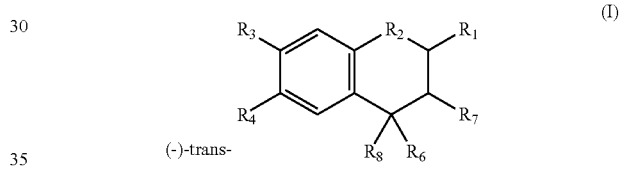
(I)

wherein,
R$_1$ is independently H, NH$_2$, NH(R'), N(R')$_2$; or

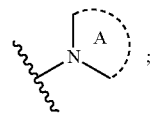

wherein ring A is a 3-8 membered heterocyclic or heteroaryl, containing 0-3 additional heteroatoms selected from O, N and S; wherein ring A is optionally substituted;
each R' is independently alkyl, alkenyl, or alkynyl, each of which may be optionally substituted;
R$_2$ is independently —(CH$_2$)n-;
each n is independently 1 or 2;
R$_3$ is independently H, OH, or halo;
R$_4$ is independently H, OH, or halo
R$_6$ is independently H or alkyl;
R$_7$ independently H, or N(alkyl)$_2$; and
R$_8$ is aryl substituted with 1, 2, 3, or 4 independent aryl, nitro, amino, heteroaryl, cycloalkyl, heterocyclic, or alkoxy;
or salt, hydrate or solvate thereof;
wherein the neuropsychiatric disorder is obesity, addiction, cocaine addiction, amphetamine/methamphetamine addiction, anxiety, depression, schizophrenia, or sleep disorders, the neurodegenerative disorder is Parkinson's Disease or Alzheimer's Disease, the neurological disorder is epilepsy, the cardiovascular disorder is hypertension, the gastrointestinal disorder is irritable bowel syndrome, and the genito-urinary tract disorder is bladder control.

8. The method of claim 7, wherein in the compound of formula (I), $R_1$ is —NMe$_2$, or

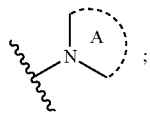

wherein ring A is a 3-8 membered heterocyclic or heteroaryl, containing 0-3 additional heteroatoms selected from O, N and S; wherein ring A is optionally substituted.

9. The method of claim 7, wherein the disorder is cocaine addiction or amphetamine or methamphetamine addiction.

10. The method of claim 7, wherein the disorder is obesity.

11. A method of treating a GPCR-mediated disorder in a subject comprising administering to the subject identified as in need thereof a compound or salt thereof, wherein the GPCR-mediated disorder is a neuropsychiatric disorder, a neurodegenerative disorder, a neurological disorder, a cardiovascular disorder, a gastrointestinal disorder, or a genito-urinary tract disorder, wherein the compound is:

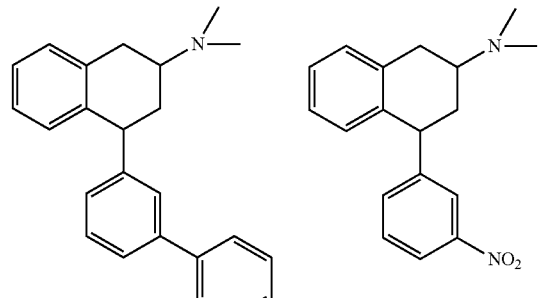

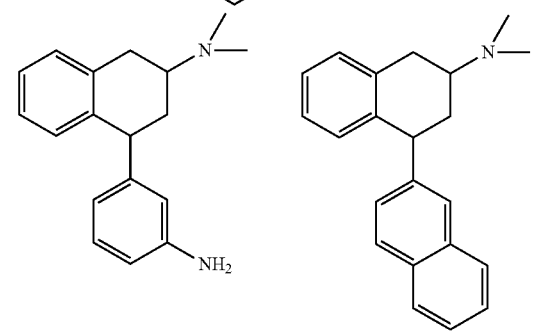

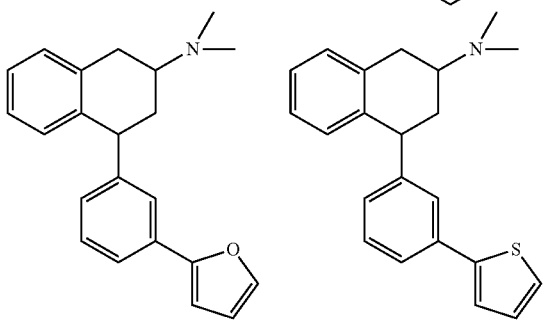

-continued

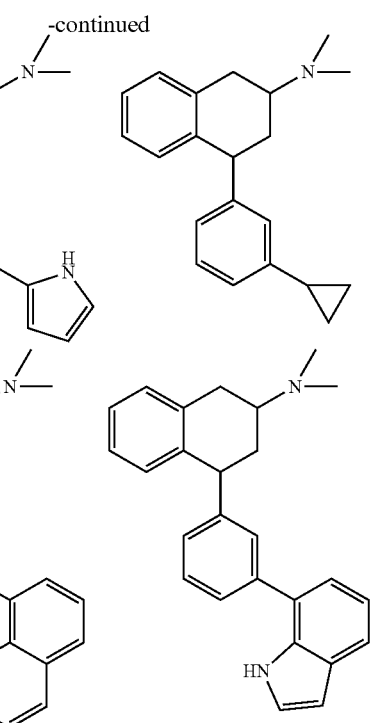

or salt thereof, wherein the neuropsychiatric disorder is obesity, addiction, cocaine addiction, amphetamine/methamphetamine addiction, anxiety, depression, schizophrenia, or sleep disorders, the neurodegenerative disorder is Parkinson's Disease or Alzheimer's Disease, the neurological disorder is epilepsy, the cardiovascular disorder is hypertension, the gastrointestinal disorder is irritable bowel syndrome, and the genito-urinary tract disorder is bladder control.

12. A method of treating a GPCR-mediated disorder in a subject comprising administering to the subject identified as in need thereof a compound of formula (I), or salt thereof, wherein the GPCR-mediated disorder is a neuropsychiatric disorder, a neurodegenerative disorder, a neurological disorder, a cardiovascular disorder, a gastrointestinal disorder, or a genito-urinary tract disorder:

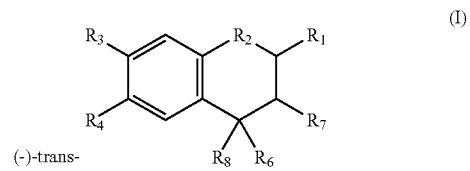

(I)

wherein,
R₁ is

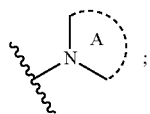

wherein ring A is a 3-8 membered heterocyclic or heteroaryl, containing 0-3 additional heteroatoms selected from O, N and S; wherein ring A is optionally substituted;
R₂ is independently —(CH₂)n-;
each n is independently 1 or 2;
R₃ is independently H, OH, or halo;
R₄ is independently H, OH, or halo
R₆ is independently H or alkyl;
R₇ is independently H, or N(alkyl)₂; and
R₈ is aryl substituted with 1, 2, 3, or 4 independent alkyl or halo;
or salt, hydrate or solvate thereof;
wherein the neuropsychiatric disorder is obesity, addiction, cocaine addiction, amphetamine/methamphetamine addiction, anxiety, depression, schizophrenia, or sleep disorders, the neurodegenerative disorder is Parkinson's Disease or Alzheimer's Disease, the neurological disorder is epilepsy, the cardiovascular disorder is hypertension, the gastrointestinal disorder is irritable bowel syndrome, and the genito-urinary tract disorder is bladder control.

13. The method of claim 12, wherein the compound of formula (I) is:

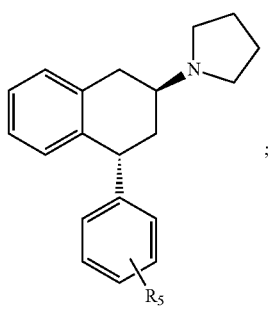

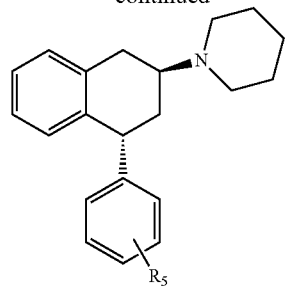

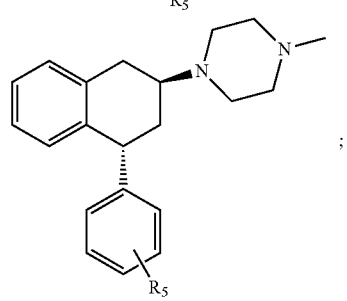

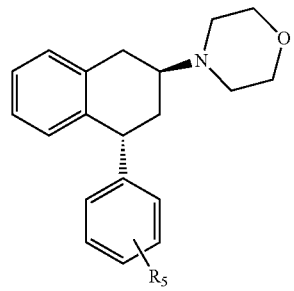

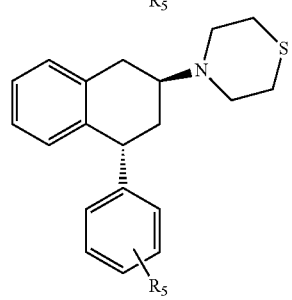

or salt, hydrate or solvate thereof.

* * * * *